(12) United States Patent
Price et al.

(10) Patent No.: US 12,169,198 B2
(45) Date of Patent: Dec. 17, 2024

(54) SYSTEMS AND METHODS FOR SAMPLE ANALYSIS

(71) Applicant: 10X GENOMICS, INC., Pleasanton, CA (US)

(72) Inventors: Andrew D. Price, Hayward, CA (US); Christopher Hindson, Livermore, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 0 days.

(21) Appl. No.: 18/235,616

(22) Filed: Aug. 18, 2023

(65) Prior Publication Data

US 2024/0044877 A1 Feb. 8, 2024

Related U.S. Application Data

(63) Continuation of application No. 16/737,762, filed on Jan. 8, 2020, now abandoned.

(60) Provisional application No. 62/789,893, filed on Jan. 8, 2019.

(51) Int. Cl.
| | | |
|---|---|---|
| *G01N 33/532* | (2006.01) | |
| *C07K 14/74* | (2006.01) | |
| *C12N 15/10* | (2006.01) | |
| *C12N 15/11* | (2006.01) | |
| *C12N 15/85* | (2006.01) | |
| *C12Q 1/6804* | (2018.01) | |
| *C12Q 1/6806* | (2018.01) | |
| *C12Q 1/6818* | (2018.01) | |
| *C12Q 1/6827* | (2018.01) | |
| *C12Q 1/6881* | (2018.01) | |
| *C40B 50/06* | (2006.01) | |
| *G01N 33/50* | (2006.01) | |
| *G01N 33/53* | (2006.01) | |
| *G01N 33/543* | (2006.01) | |
| *G01N 33/548* | (2006.01) | |
| *G01N 33/569* | (2006.01) | |
| *G01N 33/58* | (2006.01) | |
| *C40B 30/04* | (2006.01) | |
| *C40B 70/00* | (2006.01) | |

(52) U.S. Cl.
CPC ..... *G01N 33/532* (2013.01); *C07K 14/70539* (2013.01); *C12N 15/1037* (2013.01); *C12N 15/1055* (2013.01); *C12N 15/1065* (2013.01); *C12N 15/1075* (2013.01); *C12N 15/11* (2013.01); *C12N 15/85* (2013.01); *C12Q 1/6804* (2013.01); *C12Q 1/6806* (2013.01); *C12Q 1/6818* (2013.01); *C12Q 1/6827* (2013.01); *C12Q 1/6881* (2013.01); *G01N 33/5032* (2013.01); *G01N 33/505* (2013.01); *G01N 33/5304* (2013.01); *G01N 33/5306* (2013.01); *G01N 33/5308* (2013.01); *G01N 33/54306* (2013.01); *G01N 33/54366* (2013.01); *G01N 33/548* (2013.01); *G01N 33/56977* (2013.01); *G01N 33/58* (2013.01); *C12N 2310/20* (2017.05); *C12N 2320/10* (2013.01); *C12Q 2537/164* (2013.01); *C12Q 2563/179* (2013.01); *C12Q 2563/185* (2013.01); *C12Q 2565/1015* (2013.01); *C40B 30/04* (2013.01); *C40B 50/06* (2013.01); *C40B 70/00* (2013.01)

(58) Field of Classification Search
None
See application file for complete search history.

(56) References Cited

U.S. PATENT DOCUMENTS

| | | | |
|---|---|---|---|
| 4,124,638 | A | 11/1978 | Hansen |
| 5,185,099 | A | 2/1993 | Delpuech et al. |
| 5,270,183 | A | 12/1993 | Corbett et al. |
| 5,478,893 | A | 12/1995 | Ghosh et al. |
| 5,736,330 | A | 4/1998 | Fulton |
| 5,756,334 | A | 5/1998 | Perler et al. |
| 5,846,719 | A | 12/1998 | Brenner et al. |
| 5,900,481 | A | 5/1999 | Lough et al. |
| 5,942,609 | A | 8/1999 | Hunkapiller et al. |
| 5,994,056 | A | 11/1999 | Higuchi |
| 6,033,880 | A | 3/2000 | Haff et al. |
| 6,057,149 | A | 5/2000 | Burns et al. |
| 6,123,798 | A | 9/2000 | Gandhi et al. |
| 6,171,850 | B1 | 1/2001 | Nagle et al. |
| 6,172,218 | B1 | 1/2001 | Brenner |
| 6,176,962 | B1 | 1/2001 | Soane et al. |
| 6,306,590 | B1 | 10/2001 | Mehta et al. |

(Continued)

FOREIGN PATENT DOCUMENTS

| | | |
|---|---|---|
| EP | 1019496 B1 | 9/2004 |
| EP | 1841879 A2 | 10/2007 |

(Continued)

OTHER PUBLICATIONS

10X Genomics, Inc. CG000153 Rev A. Chromium Single Cell DNA Reagent Kits User Guide. 2018. 62 pages.

(Continued)

*Primary Examiner* — Kaijiang Zhang
(74) *Attorney, Agent, or Firm* — Wilson Sonsini Goodrich & Rosati

(57) ABSTRACT

The present disclosure provides systems and methods for processing or analyzing a sample. Methods may include generating supports (e.g., beads) comprising barcode molecules coupled thereto. A support comprising barcode molecules may be useful for analyzing or processing one or more analytes such as nucleic acid molecules, proteins, and/or perturbation agents.

22 Claims, 11 Drawing Sheets

Specification includes a Sequence Listing.

(56) References Cited

U.S. PATENT DOCUMENTS

| | | |
|---|---|---|
| 6,327,410 B1 | 12/2001 | Walt et al. |
| 6,379,929 B1 | 4/2002 | Burns et al. |
| 6,406,848 B1 | 6/2002 | Bridgham et al. |
| 6,409,832 B2 | 6/2002 | Weigl et al. |
| 6,492,118 B1 | 12/2002 | Abrams et al. |
| 6,524,456 B1 | 2/2003 | Ramsey et al. |
| 6,586,176 B1 | 7/2003 | Trnovsky et al. |
| 6,632,655 B1 | 10/2003 | Mehta et al. |
| 6,915,679 B2 | 7/2005 | Chien et al. |
| 7,041,481 B2 | 5/2006 | Anderson et al. |
| 7,115,400 B1 | 10/2006 | Adessi et al. |
| 7,129,091 B2 | 10/2006 | Ismagilov et al. |
| 7,268,167 B2 | 9/2007 | Higuchi et al. |
| 7,282,370 B2 | 10/2007 | Bridgham et al. |
| 7,294,503 B2 | 11/2007 | Quake et al. |
| 7,323,305 B2 | 1/2008 | Leamon et al. |
| 7,544,473 B2 | 6/2009 | Brenner |
| 7,622,076 B2 | 11/2009 | Davies et al. |
| 7,622,280 B2 | 11/2009 | Holliger et al. |
| 7,645,596 B2 | 1/2010 | Williams et al. |
| 7,708,949 B2 | 5/2010 | Stone et al. |
| 7,772,287 B2 | 8/2010 | Higuchi et al. |
| 7,776,927 B2 | 8/2010 | Chu et al. |
| 7,842,457 B2 | 11/2010 | Berka et al. |
| 7,910,354 B2 | 3/2011 | Drmanac et al. |
| 7,927,797 B2 | 4/2011 | Nobile et al. |
| 7,960,104 B2 | 6/2011 | Drmanac et al. |
| 7,968,287 B2 | 6/2011 | Griffiths et al. |
| 8,053,192 B2 | 11/2011 | Bignell et al. |
| 8,133,719 B2 | 3/2012 | Drmanac et al. |
| 8,168,385 B2 | 5/2012 | Brenner |
| 8,268,564 B2 | 9/2012 | Roth et al. |
| 8,273,573 B2 | 9/2012 | Ismagilov et al. |
| 8,298,767 B2 | 10/2012 | Brenner et al. |
| 8,304,193 B2 | 11/2012 | Ismagilov et al. |
| 8,318,433 B2 | 11/2012 | Brenner |
| 8,329,407 B2 | 12/2012 | Ismagilov et al. |
| 8,592,150 B2 | 11/2013 | Drmanac et al. |
| 8,658,430 B2 | 2/2014 | Miller et al. |
| 8,822,148 B2 | 9/2014 | Ismagliov et al. |
| 8,835,358 B2 | 9/2014 | Fodor et al. |
| 8,871,444 B2 | 10/2014 | Griffiths et al. |
| 8,889,083 B2 | 11/2014 | Ismagilov et al. |
| 8,975,302 B2 | 3/2015 | Light et al. |
| 9,012,390 B2 | 4/2015 | Holtze et al. |
| 9,029,083 B2 | 5/2015 | Griffiths et al. |
| 9,029,085 B2 | 5/2015 | Agresti et al. |
| 9,085,798 B2 | 7/2015 | Chee |
| 9,089,844 B2 | 7/2015 | Hiddessen et al. |
| 9,126,160 B2 | 9/2015 | Ness et al. |
| 9,156,010 B2 | 10/2015 | Colston et al. |
| 9,194,861 B2 | 11/2015 | Hindson et al. |
| 9,216,392 B2 | 12/2015 | Hindson et al. |
| 9,238,206 B2 | 1/2016 | Rotem et al. |
| 9,266,104 B2 | 2/2016 | Link |
| 9,290,808 B2 | 3/2016 | Fodor et al. |
| 9,328,382 B2 | 5/2016 | Drmanac et al. |
| 9,347,059 B2 | 5/2016 | Saxonov |
| 9,371,598 B2 | 6/2016 | Chee |
| 9,388,465 B2 | 7/2016 | Hindson et al. |
| 9,417,190 B2 | 8/2016 | Hindson et al. |
| 9,486,757 B2 | 11/2016 | Romanowsky et al. |
| 9,498,761 B2 | 11/2016 | Holtze et al. |
| 9,500,664 B2 | 11/2016 | Ness et al. |
| 9,567,631 B2 | 2/2017 | Hindson et al. |
| 9,593,365 B2 | 3/2017 | Frisen et al. |
| 9,623,384 B2 | 4/2017 | Hindson et al. |
| 9,637,799 B2 | 5/2017 | Fan et al. |
| 9,644,204 B2 | 5/2017 | Hindson et al. |
| 9,689,024 B2 | 6/2017 | Hindson et al. |
| 9,694,361 B2 | 7/2017 | Bharadwaj et al. |
| 9,701,998 B2 | 7/2017 | Hindson et al. |
| 9,764,322 B2 | 9/2017 | Hiddessen et al. |
| 9,824,068 B2 | 11/2017 | Wong |
| 9,868,979 B2 | 1/2018 | Chee et al. |
| 9,879,313 B2 | 1/2018 | Chee et al. |
| 9,946,577 B1 | 4/2018 | Stafford et al. |
| 9,951,386 B2 | 4/2018 | Hindson et al. |
| 9,957,558 B2 | 5/2018 | Leamon et al. |
| 9,975,122 B2 | 5/2018 | Masquelier et al. |
| 10,011,872 B1 | 7/2018 | Belgrader et al. |
| 10,017,759 B2 | 7/2018 | Kaper et al. |
| 10,030,261 B2 | 7/2018 | Frisen et al. |
| 10,059,989 B2 | 8/2018 | Giresi et al. |
| 10,221,436 B2 | 3/2019 | Hardenbol et al. |
| 10,221,442 B2 | 3/2019 | Hindson et al. |
| 10,253,364 B2 | 4/2019 | Hindson et al. |
| 10,273,541 B2 | 4/2019 | Hindson et al. |
| 10,323,279 B2 | 6/2019 | Hindson et al. |
| 10,347,365 B2 | 7/2019 | Wong et al. |
| 10,357,771 B2 | 7/2019 | Bharadwaj et al. |
| 10,395,758 B2 | 8/2019 | Schnall-Levin |
| 10,400,280 B2 | 9/2019 | Hindson et al. |
| 10,428,326 B2 | 10/2019 | Belhocine et al. |
| 10,533,221 B2 | 1/2020 | Hindson et al. |
| 10,544,413 B2 | 1/2020 | Bharadwaj et al. |
| 10,549,279 B2 | 2/2020 | Bharadwaj et al. |
| 10,557,158 B2 | 2/2020 | Hardenbol et al. |
| 10,590,244 B2 | 3/2020 | Delaney et al. |
| 10,745,742 B2 | 8/2020 | Bent et al. |
| 10,752,949 B2 | 8/2020 | Hindson et al. |
| 10,774,374 B2 | 9/2020 | Frisen et al. |
| 10,815,525 B2 | 10/2020 | Lucero et al. |
| 10,829,815 B2 | 11/2020 | Bharadwaj et al. |
| 10,837,047 B2 | 11/2020 | Delaney et al. |
| 10,874,997 B2 | 12/2020 | Weitz et al. |
| 10,995,333 B2 | 5/2021 | Pfeiffer |
| 11,371,094 B2 | 6/2022 | Ryvkin et al. |
| 11,459,607 B1 | 10/2022 | Terry et al. |
| 11,467,153 B2 | 10/2022 | Belhocine et al. |
| 11,655,499 B1 | 5/2023 | Pfeiffer |
| 11,845,983 B1 | 12/2023 | Belhocine et al. |
| 11,851,683 B1 | 12/2023 | Maheshwari et al. |
| 11,851,700 B1 | 12/2023 | Bava et al. |
| 11,952,626 B2 | 4/2024 | Pfeiffer et al. |
| 2002/0005354 A1 | 1/2002 | Spence et al. |
| 2002/0051971 A1 | 5/2002 | Stuelpnagel et al. |
| 2002/0092767 A1 | 7/2002 | Bjornson et al. |
| 2002/0119455 A1 | 8/2002 | Chan |
| 2002/0127736 A1 | 9/2002 | Chou et al. |
| 2003/0036206 A1 | 2/2003 | Chien et al. |
| 2003/0075446 A1 | 4/2003 | Culbertson et al. |
| 2003/0124509 A1 | 7/2003 | Kenis et al. |
| 2003/0215862 A1 | 11/2003 | Parce et al. |
| 2005/0130188 A1 | 6/2005 | Walt et al. |
| 2005/0250147 A1 | 11/2005 | Macevicz |
| 2005/0266582 A1 | 12/2005 | Modlin et al. |
| 2005/0287572 A1 | 12/2005 | Mathies et al. |
| 2006/0177832 A1 | 8/2006 | Brenner |
| 2006/0275782 A1 | 12/2006 | Gunderson et al. |
| 2007/0020640 A1 | 1/2007 | McCloskey et al. |
| 2007/0042419 A1 | 2/2007 | Barany et al. |
| 2007/0172873 A1 | 7/2007 | Brenner et al. |
| 2007/0190543 A1 | 8/2007 | Livak |
| 2007/0196397 A1 | 8/2007 | Torii et al. |
| 2007/0264320 A1 | 11/2007 | Lee et al. |
| 2008/0056948 A1 | 3/2008 | Dale et al. |
| 2008/0166720 A1 | 7/2008 | Hsieh et al. |
| 2008/0242560 A1 | 10/2008 | Gunderson et al. |
| 2009/0011943 A1 | 1/2009 | Drmanac et al. |
| 2009/0047713 A1 | 2/2009 | Handique |
| 2009/0099041 A1 | 4/2009 | Church et al. |
| 2009/0131543 A1 | 5/2009 | Weitz et al. |
| 2009/0148961 A1 | 6/2009 | Luchini et al. |
| 2009/0155563 A1 | 6/2009 | Petsev et al. |
| 2009/0202984 A1 | 8/2009 | Cantor |
| 2009/0235990 A1 | 9/2009 | Beer |
| 2009/0269248 A1 | 10/2009 | Falb et al. |
| 2009/0286687 A1 | 11/2009 | Dressman et al. |
| 2010/0035254 A1 | 2/2010 | Williams |
| 2010/0069263 A1 | 3/2010 | Shendure et al. |
| 2010/0086914 A1 | 4/2010 | Bentley et al. |
| 2010/0105112 A1 | 4/2010 | Holtze et al. |
| 2010/0105866 A1 | 4/2010 | Fraden et al. |

(56) References Cited

U.S. PATENT DOCUMENTS

| | | |
|---|---|---|
| 2010/0184928 A1 | 7/2010 | Kumacheva |
| 2010/0216153 A1 | 8/2010 | Lapidus et al. |
| 2010/0248991 A1 | 9/2010 | Roesler et al. |
| 2010/0304982 A1 | 12/2010 | Hinz et al. |
| 2011/0217736 A1 | 9/2011 | Hindson |
| 2011/0305761 A1 | 12/2011 | Shum et al. |
| 2012/0071331 A1 | 3/2012 | Casbon et al. |
| 2012/0172259 A1 | 7/2012 | Rigatti et al. |
| 2012/0196288 A1 | 8/2012 | Beer |
| 2012/0219947 A1 | 8/2012 | Yurkovetsky et al. |
| 2013/0028812 A1 | 1/2013 | Prieto et al. |
| 2013/0109575 A1 | 5/2013 | Kleinschmidt et al. |
| 2014/0065234 A1 | 3/2014 | Shum et al. |
| 2014/0155295 A1 | 6/2014 | Hindson et al. |
| 2014/0221239 A1 | 8/2014 | Carman et al. |
| 2014/0272996 A1 | 9/2014 | Bemis |
| 2014/0274740 A1 | 9/2014 | Srinivasan et al. |
| 2014/0302503 A1 | 10/2014 | Lowe et al. |
| 2014/0338753 A1 | 11/2014 | Sperling et al. |
| 2014/0378345 A1 | 12/2014 | Hindson et al. |
| 2015/0050697 A1* | 2/2015 | Kim .................. C12N 15/1065 435/194 |
| 2015/0051113 A1* | 2/2015 | Kim .................... C12Q 1/6869 435/6.12 |
| 2015/0267191 A1 | 9/2015 | Steelman et al. |
| 2015/0361418 A1 | 12/2015 | Reed |
| 2015/0376605 A1 | 12/2015 | Jarosz et al. |
| 2015/0376609 A1* | 12/2015 | Hindson et al. ... C12N 15/1065 |
| 2015/0376700 A1 | 12/2015 | Schnall-Levin et al. |
| 2015/0379196 A1 | 12/2015 | Schnall-Levin et al. |
| 2016/0008778 A1 | 1/2016 | Weitz et al. |
| 2016/0024558 A1 | 1/2016 | Hardenbol et al. |
| 2016/0024572 A1 | 1/2016 | Shishkin et al. |
| 2016/0053253 A1 | 2/2016 | Salathia et al. |
| 2016/0059204 A1 | 3/2016 | Hindson et al. |
| 2016/0060621 A1 | 3/2016 | Agresti et al. |
| 2016/0122753 A1 | 5/2016 | Mikkelsen et al. |
| 2016/0122817 A1 | 5/2016 | Jarosz et al. |
| 2016/0203196 A1 | 7/2016 | Schnall-Levin et al. |
| 2016/0232291 A1 | 8/2016 | Kyriazopoulou-Panagiotopoulou et al. |
| 2016/0244809 A1 | 8/2016 | Belgrader et al. |
| 2016/0281160 A1 | 9/2016 | Jarosz et al. |
| 2016/0289769 A1 | 10/2016 | Schwartz et al. |
| 2016/0314242 A1 | 10/2016 | Schnall-Levin et al. |
| 2016/0348093 A1 | 12/2016 | Price et al. |
| 2017/0016041 A1 | 1/2017 | Greenfield et al. |
| 2017/0128937 A1 | 5/2017 | Hung et al. |
| 2017/0144161 A1 | 5/2017 | Hindson et al. |
| 2017/0145476 A1 | 5/2017 | Ryvkin et al. |
| 2017/0159109 A1 | 6/2017 | Zheng et al. |
| 2017/0235876 A1 | 8/2017 | Jaffe et al. |
| 2017/0260584 A1 | 9/2017 | Zheng et al. |
| 2018/0030515 A1 | 2/2018 | Regev et al. |
| 2018/0080075 A1 | 3/2018 | Brenner et al. |
| 2018/0105808 A1 | 4/2018 | Mikkelsen et al. |
| 2018/0251825 A1* | 9/2018 | Stoeckius et al. . C12N 15/1093 |
| 2018/0312822 A1 | 11/2018 | Lee et al. |
| 2018/0312873 A1 | 11/2018 | Zheng |
| 2018/0340169 A1 | 11/2018 | Belhocine et al. |
| 2018/0371545 A1 | 12/2018 | Wong et al. |
| 2019/0060890 A1 | 2/2019 | Bharadwaj et al. |
| 2019/0060905 A1 | 2/2019 | Bharadwaj et al. |
| 2019/0064173 A1 | 2/2019 | Bharadwaj et al. |
| 2019/0071656 A1 | 3/2019 | Chang et al. |
| 2019/0127731 A1 | 5/2019 | McDermott |
| 2019/0134633 A1 | 5/2019 | Bharadwaj et al. |
| 2019/0176152 A1 | 6/2019 | Bharadwaj et al. |
| 2019/0177800 A1 | 6/2019 | Boutet et al. |
| 2019/0323088 A1 | 10/2019 | Boutet et al. |
| 2019/0345636 A1 | 11/2019 | McDermott et al. |
| 2019/0352717 A1 | 11/2019 | Schnall-Levin |
| 2019/0367997 A1 | 12/2019 | Bent et al. |
| 2019/0376118 A1 | 12/2019 | Belhocine et al. |
| 2019/0390266 A1* | 12/2019 | Sharp et al. ......... C12Q 1/6855 |
| 2020/0005902 A1 | 1/2020 | Mellen et al. |
| 2020/0032335 A1 | 1/2020 | Martinez |
| 2020/0033237 A1 | 1/2020 | Hindson et al. |
| 2020/0033366 A1 | 1/2020 | Alvarado Martinez |
| 2020/0056223 A1 | 2/2020 | Bell |
| 2020/0105373 A1 | 4/2020 | Zheng |
| 2020/0239874 A1 | 7/2020 | Mikkelsen et al. |
| 2020/0263232 A1 | 8/2020 | Bell et al. |
| 2020/0291454 A1 | 9/2020 | Belhocine et al. |
| 2020/0407775 A1 | 12/2020 | Bharadwaj et al. |
| 2021/0190770 A1 | 6/2021 | Delaney et al. |
| 2021/0230584 A1 | 7/2021 | Mikkelsen et al. |
| 2021/0270703 A1 | 9/2021 | Abousoud |
| 2022/0162671 A1 | 5/2022 | Pfeiffer et al. |
| 2022/0276229 A1 | 9/2022 | Mikkelsen et al. |
| 2022/0364150 A1 | 11/2022 | Delaney et al. |
| 2022/0403375 A1 | 12/2022 | Martinez |
| 2023/0167496 A1 | 6/2023 | Bava |
| 2023/0236176 A1 | 7/2023 | Mikkelsen et al. |
| 2024/0002914 A1 | 1/2024 | Pfeiffer |

FOREIGN PATENT DOCUMENTS

| | | |
|---|---|---|
| EP | 1967592 B1 | 4/2010 |
| EP | 2540389 A1 | 1/2013 |
| EP | 2635679 B1 | 4/2017 |
| GB | 2097692 A | 11/1982 |
| GB | 2097692 B | 5/1985 |
| WO | WO-84/02000 | 5/1984 |
| WO | WO-95/30782 | 11/1995 |
| WO | WO-99/52708 | 10/1999 |
| WO | WO-2000008212 A1 | 2/2000 |
| WO | WO-2001002850 A1 | 1/2001 |
| WO | WO-0114589 A2 | 3/2001 |
| WO | WO-0190418 A1 | 11/2001 |
| WO | WO-2001089787 A2 | 11/2001 |
| WO | WO-2004002627 A2 | 1/2004 |
| WO | WO-2004065617 A2 | 8/2004 |
| WO | WO-2004069849 A2 | 8/2004 |
| WO | WO-2004091763 A2 | 10/2004 |
| WO | WO-2005021151 A1 | 3/2005 |
| WO | WO-2005049787 A9 | 6/2005 |
| WO | WO-2005082098 A2 | 9/2005 |
| WO | WO-2006040551 A2 | 4/2006 |
| WO | WO-2006078841 A1 | 7/2006 |
| WO | WO-2006096571 A2 | 9/2006 |
| WO | WO-2007081385 A2 | 7/2007 |
| WO | WO-2007081387 A1 | 7/2007 |
| WO | WO-2007089541 A2 | 8/2007 |
| WO | WO-2007133710 A2 | 11/2007 |
| WO | WO-2007140015 A2 | 12/2007 |
| WO | WO-2007147079 A2 | 12/2007 |
| WO | WO-2008021123 A1 | 2/2008 |
| WO | WO-2008109176 A2 | 9/2008 |
| WO | WO-2008121342 A2 | 10/2008 |
| WO | WO-2008134153 A1 | 11/2008 |
| WO | WO-2008150432 A1 | 12/2008 |
| WO | WO-2009011808 A1 | 1/2009 |
| WO | WO-2009015296 A1 | 1/2009 |
| WO | WO-2009085215 A1 | 7/2009 |
| WO | WO-2009152928 A2 | 12/2009 |
| WO | WO-2010033200 A2 | 3/2010 |
| WO | WO-2010104604 A1 | 9/2010 |
| WO | WO-2010117620 A2 | 10/2010 |
| WO | WO-2010148039 A2 | 12/2010 |
| WO | WO-2011028539 A1 | 3/2011 |
| WO | WO-2011047870 A1 | 4/2011 |
| WO | WO-2011056546 A1 | 5/2011 |
| WO | WO-2011066476 A1 | 6/2011 |
| WO | WO-2012048341 A1 | 4/2012 |
| WO | WO-2012061832 A1 | 5/2012 |
| WO | WO-2012083225 A2 | 6/2012 |
| WO | WO-2012106546 A2 | 8/2012 |
| WO | WO-2012112804 A1 | 8/2012 |
| WO | WO-2012112970 A2 | 8/2012 |
| WO | WO-2012116331 A2 | 8/2012 |
| WO | WO-2012142531 A2 | 10/2012 |
| WO | WO-2012142611 A2 | 10/2012 |
| WO | WO-2012149042 A2 | 11/2012 |

(56) References Cited

FOREIGN PATENT DOCUMENTS

| | | |
|---|---|---|
| WO | WO-2012166425 A2 | 12/2012 |
| WO | WO-2012167142 A2 | 12/2012 |
| WO | WO-2013019751 A1 | 2/2013 |
| WO | WO-2013036929 A1 | 3/2013 |
| WO | WO-2013055955 A1 | 4/2013 |
| WO | WO-2013096643 A1 | 6/2013 |
| WO | WO-2013126741 A1 | 8/2013 |
| WO | WO-2013134261 A1 | 9/2013 |
| WO | WO-2014028378 A2 | 2/2014 |
| WO | WO-2014108810 A2 | 7/2014 |
| WO | WO-2014165559 A2 | 10/2014 |
| WO | WO-2015015199 A2 | 2/2015 |
| WO | WO-2015044428 A1 | 4/2015 |
| WO | WO-2015164212 A1 | 10/2015 |
| WO | WO-2016040476 A1 | 3/2016 |
| WO | WO-2016061517 A2 | 4/2016 |
| WO | WO-2016126871 A1 | 8/2016 |
| WO | WO-2016168584 A1 | 10/2016 |
| WO | WO-2017015075 A1 | 1/2017 |
| WO | WO-2017066231 A1 | 4/2017 |
| WO | WO-2017139690 A1 | 8/2017 |
| WO | WO-2017180949 A1 | 10/2017 |
| WO | WO-2017184707 A1 | 10/2017 |
| WO | WO-2017197343 A2 | 11/2017 |
| WO | WO-2018039338 A1 | 3/2018 |
| WO | WO-2018091676 A1 | 5/2018 |
| WO | WO-2018119301 A1 | 6/2018 |
| WO | WO-2018119447 A2 | 6/2018 |
| WO | WO-2018172726 A1 | 9/2018 |
| WO | WO-2018191701 A1 | 10/2018 |
| WO | WO-2018213643 A1 | 11/2018 |
| WO | WO-2018226546 A1 | 12/2018 |
| WO | WO-2018236615 A1 | 12/2018 |
| WO | WO-2019028166 A1 | 2/2019 |
| WO | WO-2019040637 A1 | 2/2019 |
| WO | WO-2019083852 A1 | 5/2019 |
| WO | WO-2019084043 A1 | 5/2019 |
| WO | WO-2019084165 A1 | 5/2019 |
| WO | WO-2019108851 A1 | 6/2019 |
| WO | WO-2019113235 A1 | 6/2019 |
| WO | WO-2019118355 A1 | 6/2019 |
| WO | WO-2019126789 A1 | 6/2019 |
| WO | WO-2019148042 A1 | 8/2019 |
| WO | WO-2019152108 A1 | 8/2019 |
| WO | WO-2019157529 A1 | 8/2019 |
| WO | WO-2019165318 A1 | 8/2019 |
| WO | WO-2019169028 A1 | 9/2019 |
| WO | WO-2019169347 A1 | 9/2019 |
| WO | WO-2019191321 A1 | 10/2019 |
| WO | WO-2019217758 A1 | 11/2019 |
| WO | WO-2020028882 A1 | 2/2020 |
| WO | WO-2020041148 A1 | 2/2020 |
| WO | WO-2020142779 A1 | 7/2020 |
| WO | WO-2020167862 A1 | 8/2020 |
| WO | WO-2020167866 A1 | 8/2020 |
| WO | WO-2020168013 A1 | 8/2020 |
| WO | WO-2020198532 A1 | 10/2020 |
| WO | WO-2021046475 A1 | 3/2021 |
| WO | WO-2021133845 A1 | 7/2021 |
| WO | WO-2021207610 A1 | 10/2021 |
| WO | WO-2021212042 A1 | 10/2021 |
| WO | WO-2021/222302 A1 | 11/2021 |
| WO | WO-2021222301 A1 | 11/2021 |
| WO | WO-2022103712 A1 | 5/2022 |
| WO | WO-2022182682 A1 | 9/2022 |
| WO | WO-2022182785 A1 | 9/2022 |
| WO | WO-2022271908 A1 | 12/2022 |
| WO | WO-2023076528 A2 | 5/2023 |

OTHER PUBLICATIONS

10X Genomics, Inc. CG000184 Rev A. Chromium Single Cell 3' Reagent Kits v3 User Guide with Feature Barcoding Technology for CRISPR Screening. 2018. 70 pages.
10X Genomics, Inc. CG000185 Rev B. Chromium Single Cell 3' Reagent Kits User Guide with Feature Barcoding Technology for Cell Surface Protein. 2018. 66 pages.
10X Genomics, Inc. CG000208 Rev E. Chromium Next GEM Single Cell V(D)J reagent Kits v1.1 User Guide with Feature Barcode Technology for Cell Surface Protein. 2020. 88 pages.
10X Genomics, Inc. CG000209 Rev D. Chromium Next GEM Single Cell ATAC Reagent Kits v1.1 User Guide. 2020.
10X Genomics, Inc. CG000239 Rev B. Visium Spatial Gene Expression Reagent Kits User Guide. 2020.
10X Genomics, Inc. CG00026. Chromium Single Cell 3' Reagent Kit User Guide. 2016.
10X Genomics, Inc. LIT00003 Rev B Chromium Genome Solution Application Note. 2017.
Abate, A.R. et al. "Beating Poisson encapsulation statistics using close-packed ordering" Lab on a Chip (Sep. 21, 2009) 9(18):2628-2631.
Adamson et al., "Production of arrays of chemically distinct nanolitre plugs via repeated splitting in microfluidic devices", Lab Chip 6(9): 1178-1186 (Sep. 2006).
Agasti, S.S. et al. "Photocleavable DNA barcode-antibody conjugates allow sensitive and multiplexed protein analysis in single cell" J Am Chem Soc (2012) 134(45):18499-18502.
Amini, S. et al. "Haplotype-resolved whole-genome sequencing by contiguity-preserving transposition and combinatorial indexing" Nature Genetics (2014) 46:1343-1349 doi:10.1038/ng.3119.
Anna et al.: Formation of dispersions using "flow focusing" in microchannels: Applied Physics Letters, vol. 82, No. 3, pp. 364-366 (2003).
Baret, "Surfactants in droplet-based microfluidics" Lab Chip (12(3):422-433 (2012).
Beer et al. On-Chip, Real-Time, Single-Copy Polymerase Chain Reaction in Picoliter Droplets. Anal Chem 79:8471-8475 (2007).
Braeckmans et al., Scanning the Code. Modern Drug Discovery. 2003:28-32.
Brenner, et al. "In vitro cloning of complex mixtures of DNA on microbeads: physical separation of differentially expressed cDNAs." Proc Natl Acad Sci U S A. Feb. 15, 2000;97(4):1665-70.
Buchman GW, et al. Selective RNA amplification: a novel method using dUMP-containing primers and uracil DNA glycosylase. PCR Methods Appl. Aug. 1993; 3(1):28-31.
Burns, et al. An Integrated Nanoliter DNA Analysis Device. Science. Oct. 16, 1998;282(5388):484-7.
Burns, et al. Microfabricated structures for integrated DNA analysis. Proc Natl Acad Sci U S A. May 28, 1996; 93(11): 5556-5561.
Burns, et al. The intensification of rapid reactions in multiphase systems using slug flow in capillaries. Lab Chip. Sep. 2001;1(1):10-15. Epub Aug. 9, 2001.
Chen, et al. Chemical transfection of cells in picoliter aqueous droplets in fluorocarbon oil. Anal Chem. Nov. 15, 2011;83(22):8816-20. doi: 10.1021/ac2022794. Epub Oct. 17, 2011.
Chien et al. "Multiport flow-control system for lab-on-a-chip microfluidic devices", Fresenius J. Anal Chem, 371:106-111 (Jul. 27, 2001).
Chu, et al. Controllable monodisperse multiple emulsions. Angew Chem Int Ed Engl. 2007;46(47):8970-4.
Clausell-Tormos et al., "Droplet-based microfluidic platforms for the encapsulation and screening of mammalian cells and multicellular organisms", Chem. Biol. 15:427-437 (2008).
Co-pending U.S. Appl. No. 16/434,076, inventor Giresi; Paul, filed Jun. 6, 2019.
Co-pending U.S. Appl. No. 16/434,084, inventor Giresi; Paul, filed Jun. 6, 2019.
Co-pending U.S. Appl. No. 16/434,102, inventors Price; Andrew D. et al., filed Jun. 6, 2019.
Co-pending U.S. Appl. No. 16/737,762, inventors Price; Andrew D et al., filed Jan. 8, 2020.
Co-pending U.S. Appl. No. 16/737,770, inventors Belhocine; Zahara Kamila et al., filed Jan. 8, 2020.
Co-pending U.S. Appl. No. 16/789,273, inventors Maheshwari; Arundhati Shamoni et al., filed Feb. 12, 2020.
Co-pending U.S. Appl. No. 17/014,909, inventor Giresi; Paul, filed Sep. 8, 2020.

(56) References Cited

OTHER PUBLICATIONS

Co-pending U.S. Appl. No. 17/148,942, inventors McDermott; Geoffrey et al., filed Jan. 14, 2021.
Co-pending U.S. Appl. No. 17/166,982, inventors McDermott; Geoffrey et al., filed Feb. 3, 2021.
Co-pending U.S. Appl. No. 17/175,542, inventors Maheshwari; Arundhati Shamoni et al., filed Feb. 12, 2021.
Co-pending U.S. Appl. No. 17/220,303, inventor Walter; Dagmar, filed Apr. 1, 2021.
Co-pending U.S. Appl. No. 17/318,364, inventors Bava; Felice Alessio et al., filed May 12, 2021.
Co-pending U.S. Appl. No. 17/381,612, inventor Martinez; Luigi Jhon Alvarado, filed Jul. 21, 2021.
Co-pending U.S. Appl. No. 17/512,241, inventors Hill; Andrew John et al., filed Oct. 27, 2021.
Co-pending U.S. Appl. No. 17/517,408, inventors Salmanzadeh; Alireza et al., filed Nov. 2, 2021.
Co-pending U.S. Appl. No. 17/518,213, inventor Lund; Paul Eugene, filed Nov. 3, 2021.
Co-pending U.S. Appl. No. 17/522,741, inventors Zheng; Xinying et al., filed Nov. 9, 2021.
Co-pending U.S. Appl. No. 17/545,862, inventor Katherine; Pfeiffer, filed Dec. 8, 2021.
Co-pending U.S. Appl. No. 17/573,350, inventor Corey; M. Nemec, filed Jan. 11, 2022.
Co-pending U.S. Appl. No. 17/580,947, inventor Gibbons; Michael, filed Jan. 21, 2022.
Co-pending U.S. Appl. No. 18/046,843, inventor Toh; Mckenzi, filed Oct. 14, 2022.
Co-pending U.S. Appl. No. 18/152,650, inventor Shastry; Shankar, filed Jan. 10, 2023.
Damean, et al. Simultaneous measurement of reactions in microdroplets filled by concentration gradients. Lab Chip. Jun. 21, 2009;9(12):1707-13. doi: 10.1039/b821021g. Epub Mar. 19, 2009.
Dixit, et al. Perturb-Seq: Dissecting Molecular Circuits with Scalable Single-Cell RNA Profiling of Pooled Genetic Screens. Cell. Dec. 15, 2016;167(7):1853-1866.e17. doi: 10.1016/j.cell.2016.11.038.
Drmanac et al., Sequencing by hybridization (SBH): advantages, achievements, and opportunities. Adv Biochem Eng Biotechnol. 2002;77:75-101.
Duffy et al., Rapid Protyping of Microfluidic Systems and Polydimethylsiloxane, Anal Chem 70:4974-4984 (1998).
Eastburn, et al. Ultrahigh-throughput mammalian single-cell reverse-transcriptase polymerase chain reaction in microfluidic droplets. Anal Chem. Aug. 20, 2013;85(16):8016-21. doi: 10.1021/ac402057q. Epub Aug. 8, 2013.
Esser-Kahn, et al. Triggered release from polymer capsules. Macromolecules. 2011; 44:5539-5553.
Gericke, et al. Functional cellulose beads: preparation, characterization, and applications. Chemical reviews 113.7 (2013): 4812-4836.
Guo, et al. Droplet microfluidics for high-throughput biological assays. Lab Chip. Jun. 21, 2012;12(12):2146-55. doi: 10.1039/c2lc21147e. Epub Feb. 9, 2012.
Gyarmati, et al. Reversible disulphide formation in polymer networks: a versatile functional group from synthesis to applications. European Polymer Journal. 2013; 49:1268-1286.
Hashimshony, et al. CEL-Seq: Single-Cell RNA-Seq by Multiplexed Linear Amplification. Cell Rep. Sep. 27, 2012;2(3):666-73. doi: 10.1016/j.celrep.2012.08.003. Epub Aug. 30, 2012.
Hein at al., Click Chemistry, A Powerful Tool for Pharmaceutical Sciences. Pharmaceutical Research 25:2216-2230 (2008).
Holtze, et al. Biocompatible surfactants for water-in-fluorocarbon emulsions. Lab Chip. Oct. 2008;8(10):1632-9. doi: 10.1039/b806706f. Epub Sep. 2, 2008.
Hug, et al. Measurement of the number of molecules of a single mRNA species in a complex mRNA preparation. J Theor Biol. Apr. 21, 2003;221(4):615-24.

Islam, et al. Highly multiplexed and strand-specific single-cell RNA 5' end sequencing. Nat Protoc. Apr. 5, 2012;7(5):813-28. doi: 10.1038/nprot.2012.022.
Jaitin, et al. Massively parallel single-cell RNA-seq for marker-free decomposition of tissues into cell types. Science. Feb. 14, 2014;343(6172):776-9. doi: 10.1126/science.1247651.
Jarosz, M. et al. "Using 1ng of DNA to detect haplotype phasing and gene fusions from whole exome sequencing of cancer cell lines" Cancer Res (2015) 75(supp15):4742.
Kaper, et al. Supporting Information for "Whole-genome haplotyping by dilution, amplification, and sequencing." Proc Natl Acad Sci U S A. Apr. 2, 2013;110(14):5552-7. doi: 10.1073/pnas.1218696110. Epub Mar. 18, 2013.
Kaper, et al. Whole-genome haplotyping by dilution, amplification, and sequencing. Proc Natl Acad Sci U S A. Apr. 2, 2013;110(14):5552-7. doi: 10.1073/pnas.1218696110. Epub Mar. 18, 2013.
Kenis, et al. Microfabrication Inside Capillaries Using Multiphase Laminar Flow Patterning. Science. 1999; 285:83-85.
Kivioja, et al. Counting absolute Nos. of molecules using unique molecular identifiers. Nat Methods. Nov. 20, 2011;9(1):72-4.
Klein, et al. Droplet barcoding for single-cell transcriptomics applied to embryonic stem cells. Cell. May 21, 2015; 161:1187-1201.
Kolb, et al. Click Chemistry: Diverse Chemical Function from a Few Good Reactions. Angew Chem Int Ed Engl. Jun. 1, 2001; 40(11):2004-2021. doi: 10.1002/1521-3773(20010601)40:112004::AID-ANIE20043.0.CO;2-5.
Korlach et al., Methods in Enzymology, Real-Time DNA Sequencing from Single Polymerase Molecules, (2010) 472:431-455.
Koster et al., "Drop-based microfluidic devices for encapsulation of single cells", Lab on a Chip The Royal Soc. of Chem. 8: 1110-1115 (2008).
Lagally, et al. Single-Molecular DNA Amplification and Analysis in an Integrated Microfluidic Device. Anal Chem. Feb. 1, 2001;73(3):565-70.
Lennon et al. A scalable, fully automated process for construction of sequence-ready barcoded libraries for 454. Genome Biology 11:R15 (2010).
Macosko, et al. Highly Parallel Genome-wide Expression Profiling of Individual Cells Using Nanoliter Droplets. Cell. May 21, 2015;161(5):1202-14. doi: 10.1016/j.cell.2015.05.002.
Madl, et al. "Bioorthogonal Strategies for Engineering Extracellular matrices", Madal, Chritopher, Adv. Funct. Master. Jan. 19, 2018, vol. 28, 1706046, pp. 1-21.
Mair, et al. Injection molded microfluidic chips featuring integrated interconnects. Lab Chip. Oct. 2006;6(10):1346-54. Epub Jul. 31, 2006.
McCoy, R. et al. "Illumina TruSeq Synthetic Long-Reads Empower De Novo Assembly and Resolve Complex, Highly-Repetitive Transposable Elements" PLOS (2014) 9(9):e1016689.
Microfluidic ChipShop. Microfluidic product catalogue. Oct. 2009. 48 pages.
Mimitou, et al. Expanding the CITE-seq tool-kit: Detection of proteins, transcriptomes, clonotypes and CRISPR perturbations with multiplexing, in a single assay. bioRxiv preprint first posted online Nov. 8, 2018; doi: http://dx.doi.org/10.1101/466466.
Navin. The first five years of single-cell cancer genomics and beyond. Genome Res. Oct. 2015;25(10):1499-507. doi: 10.1101/gr.191098.115.
Nisisako, et al. Droplet formation in a microchannel network. Lab Chip. Feb. 2002;2(1):24-6. Epub Jan. 18, 2002.
Nisisako, T. et al. Droplet Formation in a Microchannel on PMMA Plate. Micro Total Analysis Systems. 2001. Kluwer Academic Publishers. pp. 137-138.
Nisisako, T. et al., Microfluidics large-scale integration on a chip for mass production of monodisperse droplets and particles, The Royal Society of Chemistry: Lab Chip, (Nov. 23, 2007) 8:287-293.
Novak, R. et al., "Single cell multiplex gene detection and sequencing using microfluidically generated agarose emulsions" Angew. Chem. Int. Ed. Engl. (2011) 50(2):390-395.
Orakdogen, N. "Novel responsive poly(N,N-dimethylaminoethyl methacrylate) gel beads: preparation, mechanical properties and pH-dependent swelling behavior" J Polym Res (2012) 19:9914.

(56) References Cited

OTHER PUBLICATIONS

Perrott, Jimmy. Optimization and Improvement of Emulsion PCR for the Ion Torrent Next-Generation Sequencing Platform. (2011) Thesis.
Peters, B.A. et al. Accurate whole-genome sequencing and haplotyping from 10 to 20 human cells. Nature, 487(7406):190-195 (Jul. 11, 2012).
Plunkett, et al. Chymotrypsin responsive hydrogel: application of a disulfide exchange protocol for the preparation of methacrylamide containing peptides. Biomacromolecules. Mar.-Apr. 2005;6(2):632-7.
Priest, et al. Generation of Monodisperse Gel Emulsions in a Microfluidic Device, Applied Physics Letters, 88:024106 (2006).
Pushkarev et al. "Single-molecule sequencing of an individual human genome," Nature Biotech (2009) 27:847-850.
Ramsey, J.M. "The burgeoning power of the shrinking laboratory" Nature Biotech (1999) 17:1061-1062.
Ramskold et al. (2012) "Full-length mRNA-Seq from single-cell levels of RNA and individual circulating tumor cells" Nature Biotechnology 30(8):777-782.
Roche. Using Multiplex Identifier (MID) Adaptors for the GS FLX Titanium Chemistry Basic MID Set Genome Sequencer FLX System, Technical Bulletin 004-2009, (Apr. 1, 2009) pp. 1-11.
Rotem, A. et al., "High-throughput single-cell labeling (Hi-SCL) for RNA-Seq using drop-based microfluidics" PLOS One (May 22, 2015) 0116328 (14 pages).
Saikia, et al. Simultaneous multiplexed amplicon sequencing and transcriptome profiling in single cells. Nat Methods. Jan. 2019;16(1):59-62. doi: 10.1038/s41592-018-0259-9. Epub Dec. 17, 2018.
Schubert, et al. Microemulsifying fluorinated oils with mixtures of fluorinated and hydrogenated surfactants. Colloids and Surfaces A; Physicochemical and Engineering Aspects, 84(1994) 97-106.
Seiffert, et al. Microfluidic fabrication of smart microgels from macromolecular precursors. Polymer. vol. 51, Issue 25, Nov. 26, 2010, pp. 5883-5889.
Seiffert, S. et al., "Smart microgel capsules from macromolecular precursors" J. Am. Chem. Soc. (2010) 132:6606-6609.
Shah, et al. "Fabrication of mono disperse thermosensitive microgels and gel capsules in micro fluidic devices", Soft Matter, 4:2303-2309 (2008).
Shelbourne et al. Fast copper-free click DNA ligation by the ring-strain promoted alkyne-azide cycloaddition reaction. Chem. Commun., 2011, 47:6257-6259.
Shendure, et al., Accurate Multiplex Polony Sequencing of an Evolved Bacterial Genome. Science 309.5741 (Sep. 2005): 1728-1732. XP002427180, ISSN: 0036-8075, DOI: 10.1126/SCIENCE.1117839.
Smith, et al. Highly-multiplexed barcode sequencing: an efficient method for parallel analysis of pooled samples. Nucleic Acids Research, 38(13): e142 (2010).
Song, et al. Reactions in droplets in microfluidic channels. Angew Chem Int Ed Engl. Nov. 13, 2006;45(44):7336-56.
Spitale et al., "Structural imprints in vivo decode RNA regulatory mechanisms," Nature. Mar. 26, 2015;519(7544):486-90; doi: 10.1038/nature14263. Epub Mar. 18, 2015.
Thaxton, C.S. et al. "A Bio-Bar-Code Assay Based Upon Dithiothreitol Oligonucleotide Release" Anal Chem (2005) 77:8174-8178.
Theberge, et al. Microdroplets in microfluidics: an evolving platform for discoveries in chemistry and biology. Angew Chem Int Ed Engl. Aug. 9, 2010;49(34):5846-68. doi: 10.1002/anie.200906653.
Thorsen, et al. Dynamic pattern formation in a vesicle-generating microfluidic device. Physical Review Letters. American Physical Society. 2001; 86(18):4163-4166.
Tonelli, et al. Perfluoropolyether functional oligomers: unusual reactivity in organic chemistry. Journal of fluorine chemistry. 2002; 118(1)107-121.
Turchinovich, et al. "Capture and Amplification by Tailing and Switching (CATS): An Ultrasensitive Ligation-Independent Method for Generation of DNA Libraries for Deep Sequencing from Picogram Amounts of DNA and RNA." RNA Biology 11.7 (2014): 817-828. PMC. Web. Nov. 13, 2017.
Uttamapinant, et al. Fast, cell-compatible click chemistry with copper-chelating azides for biomolecular labeling. Angew. Chem. Int. End. Engl., Jun. 11, 2012: 51(24) pp. 5852-5856.
Wagner, et al. Biocompatible fluorinated polyglycerols for droplet microfluidics as an alternative to PEG-based copolymer surfactants. Lab Chip. Jan. 7, 2016;16(1):65-9. doi: 10.1039/c5lc00823a. Epub Dec. 2, 2015.
Weigl, et al. Microfluidic Diffusion-Based Separation and Detection. Science. 1999; pp. 346-347.
Williams, et al. Amplification of complex gene libraries by emulsion PCR. Nature Methods. 2006;3(7):545-50.
Zhang, et al. One-step fabrication of supramolecular microcapsules from microfluidic droplets. Science. Feb. 10, 2012;335(6069):690-4. doi: 10.1126/science.1215416.
Zheng, et al. Massively parallel digital transcriptional profiling of single cells. Nat Commun. Jan. 16, 2017;8:14049. doi: 10.1038/ncomms14049.
Zheng, X.Y. et al. "Haplotyping germline and cancer genomes with high-throughput linked-read sequencing" Nature Biotech (Feb. 1, 2016) 34(3):303-311.
Zhu, et al. Reverse transcriptase template switching: a SMART approach for full-length cDNA library construction. Biotechniques. Apr. 2001;30(4):892-7.
Co-pending U.S. Appl. No. 18/392,684, inventors Fernandes; Sunjay Jude et al., filed Dec. 21, 2023.
Co-pending U.S. Appl. No. 18/643,684, inventor Bava; Felice Alessio, filed Apr. 23, 2024.
Co-pending U.S. Appl. No. 18/743,583, inventor Nagendran; Monica, filed Jun. 14, 2024.

\* cited by examiner

SEQUENCE LISTING

```
Sequence total quantity: 165
SEQ ID NO: 1            moltype = DNA  length = 16
FEATURE                 Location/Qualifiers
source                  1..16
                        mol_type = other DNA
                        organism = synthetic construct
SEQUENCE: 1
tgccttgtaa cgcgaa                                                       16

SEQ ID NO: 2            moltype = DNA  length = 16
FEATURE                 Location/Qualifiers
source                  1..16
                        mol_type = other DNA
                        organism = synthetic construct
SEQUENCE: 2
tatggccgcg caatta                                                       16

SEQ ID NO: 3            moltype = DNA  length = 16
FEATURE                 Location/Qualifiers
source                  1..16
                        mol_type = other DNA
                        organism = synthetic construct
SEQUENCE: 3
ttcgagcgcg caatta                                                       16

SEQ ID NO: 4            moltype = DNA  length = 16
```

```
FEATURE                  Location/Qualifiers
source                   1..16
                         mol_type = other DNA
                         organism = synthetic construct
SEQUENCE: 4
attgcgccga acgtat                                                        16

SEQ ID NO: 5             moltype = DNA   length = 16
FEATURE                  Location/Qualifiers
source                   1..16
                         mol_type = other DNA
                         organism = synthetic construct
SEQUENCE: 5
gttgcacgcg caatta                                                        16

SEQ ID NO: 6             moltype = DNA   length = 16
FEATURE                  Location/Qualifiers
source                   1..16
                         mol_type = other DNA
                         organism = synthetic construct
SEQUENCE: 6
tgccattgcg cgataa                                                        16

SEQ ID NO: 7             moltype = DNA   length = 16
FEATURE                  Location/Qualifiers
source                   1..16
                         mol_type = other DNA
                         organism = synthetic construct
SEQUENCE: 7
aaggatcgcg cctatt                                                        16

SEQ ID NO: 8             moltype = DNA   length = 16
FEATURE                  Location/Qualifiers
source                   1..16
                         mol_type = other DNA
                         organism = synthetic construct
SEQUENCE: 8
gttacgcgcg caatta                                                        16

SEQ ID NO: 9             moltype = DNA   length = 16
FEATURE                  Location/Qualifiers
source                   1..16
                         mol_type = other DNA
                         organism = synthetic construct
SEQUENCE: 9
agcatgtcgc gcatta                                                        16

SEQ ID NO: 10            moltype = DNA   length = 16
FEATURE                  Location/Qualifiers
source                   1..16
                         mol_type = other DNA
                         organism = synthetic construct
SEQUENCE: 10
ttcgcaacgg tcgaat                                                        16

SEQ ID NO: 11            moltype = DNA   length = 16
FEATURE                  Location/Qualifiers
source                   1..16
                         mol_type = other DNA
                         organism = synthetic construct
SEQUENCE: 11
attgcgcgcg aattac                                                        16

SEQ ID NO: 12            moltype = DNA   length = 16
FEATURE                  Location/Qualifiers
source                   1..16
                         mol_type = other DNA
                         organism = synthetic construct
SEQUENCE: 12
tcttagcgga cgcaat                                                        16

SEQ ID NO: 13            moltype = DNA   length = 16
FEATURE                  Location/Qualifiers
source                   1..16
                         mol_type = other DNA
                         organism = synthetic construct
SEQUENCE: 13
atccatggcg cgatta                                                        16
```

-continued

| | | |
|---|---|---|
| SEQ ID NO: 14<br>FEATURE<br>source | moltype = DNA length = 16<br>Location/Qualifiers<br>1..16<br>mol_type = other DNA<br>organism = synthetic construct | |
| SEQUENCE: 14<br>gttcgcacgc gaatta | | 16 |
| SEQ ID NO: 15<br>FEATURE<br>source | moltype = DNA length = 16<br>Location/Qualifiers<br>1..16<br>mol_type = other DNA<br>organism = synthetic construct | |
| SEQUENCE: 15<br>cgattgcgcg acatta | | 16 |
| SEQ ID NO: 16<br>FEATURE<br>source | moltype = DNA length = 16<br>Location/Qualifiers<br>1..16<br>mol_type = other DNA<br>organism = synthetic construct | |
| SEQUENCE: 16<br>tgatcgcgct acgaat | | 16 |
| SEQ ID NO: 17<br>FEATURE<br>source | moltype = DNA length = 16<br>Location/Qualifiers<br>1..16<br>mol_type = other DNA<br>organism = synthetic construct | |
| SEQUENCE: 17<br>cgcattcaat tggcga | | 16 |
| SEQ ID NO: 18<br>FEATURE<br>source | moltype = DNA length = 16<br>Location/Qualifiers<br>1..16<br>mol_type = other DNA<br>organism = synthetic construct | |
| SEQUENCE: 18<br>aacgttcgcg attgac | | 16 |
| SEQ ID NO: 19<br>FEATURE<br>source | moltype = DNA length = 16<br>Location/Qualifiers<br>1..16<br>mol_type = other DNA<br>organism = synthetic construct | |
| SEQUENCE: 19<br>gcttgaccgc gaatta | | 16 |
| SEQ ID NO: 20<br>FEATURE<br>source | moltype = DNA length = 16<br>Location/Qualifiers<br>1..16<br>mol_type = other DNA<br>organism = synthetic construct | |
| SEQUENCE: 20<br>actgcgcgat tcgtaa | | 16 |
| SEQ ID NO: 21<br>FEATURE<br>source | moltype = DNA length = 16<br>Location/Qualifiers<br>1..16<br>mol_type = other DNA<br>organism = synthetic construct | |
| SEQUENCE: 21<br>tccaataatg cgcggt | | 16 |
| SEQ ID NO: 22<br>FEATURE<br>source | moltype = DNA length = 16<br>Location/Qualifiers<br>1..16<br>mol_type = other DNA<br>organism = synthetic construct | |
| SEQUENCE: 22<br>agtcatcgac cggatt | | 16 |
| SEQ ID NO: 23<br>FEATURE<br>source | moltype = DNA length = 16<br>Location/Qualifiers<br>1..16<br>mol_type = other DNA<br>organism = synthetic construct | |
| SEQUENCE: 23<br>agacttcgcg cgatta | | 16 |

```
SEQ ID NO: 24            moltype = DNA  length = 16
FEATURE                  Location/Qualifiers
source                   1..16
                         mol_type = other DNA
                         organism = synthetic construct
SEQUENCE: 24
ctgagtcgcg caatta                                                           16

SEQ ID NO: 25            moltype = DNA  length = 16
FEATURE                  Location/Qualifiers
source                   1..16
                         mol_type = other DNA
                         organism = synthetic construct
SEQUENCE: 25
tcgctaacgg tcgaat                                                           16

SEQ ID NO: 26            moltype = DNA  length = 16
FEATURE                  Location/Qualifiers
source                   1..16
                         mol_type = other DNA
                         organism = synthetic construct
SEQUENCE: 26
tatgcgcgcg aattac                                                           16

SEQ ID NO: 27            moltype = DNA  length = 16
FEATURE                  Location/Qualifiers
source                   1..16
                         mol_type = other DNA
                         organism = synthetic construct
SEQUENCE: 27
tatgcgcgct acgaat                                                           16

SEQ ID NO: 28            moltype = DNA  length = 16
FEATURE                  Location/Qualifiers
source                   1..16
                         mol_type = other DNA
                         organism = synthetic construct
SEQUENCE: 28
aactgcgcga ttcgta                                                           16

SEQ ID NO: 29            moltype = DNA  length = 16
FEATURE                  Location/Qualifiers
source                   1..16
                         mol_type = other DNA
                         organism = synthetic construct
SEQUENCE: 29
tggaccgcgc atatta                                                           16

SEQ ID NO: 30            moltype = DNA  length = 16
FEATURE                  Location/Qualifiers
source                   1..16
                         mol_type = other DNA
                         organism = synthetic construct
SEQUENCE: 30
tatcacaatg cgcggt                                                           16

SEQ ID NO: 31            moltype = DNA  length = 16
FEATURE                  Location/Qualifiers
source                   1..16
                         mol_type = other DNA
                         organism = synthetic construct
SEQUENCE: 31
gtcacgcgcg aattat                                                           16

SEQ ID NO: 32            moltype = DNA  length = 16
FEATURE                  Location/Qualifiers
source                   1..16
                         mol_type = other DNA
                         organism = synthetic construct
SEQUENCE: 32
gtctagcgcg caatta                                                           16

SEQ ID NO: 33            moltype = DNA  length = 16
FEATURE                  Location/Qualifiers
source                   1..16
                         mol_type = other DNA
                         organism = synthetic construct
SEQUENCE: 33
```
tctgcaacgg tcgaat                                                              16

SEQ ID NO: 34            moltype = DNA   length = 16
FEATURE                  Location/Qualifiers
source                   1..16
                         mol_type = other DNA
                         organism = synthetic construct SEQUENCE: 34
ccagtgcgcg aattat                                                              16

SEQ ID NO: 35            moltype = DNA   length = 16
FEATURE                  Location/Qualifiers
source                   1..16
                         mol_type = other DNA
                         organism = synthetic construct SEQUENCE: 35
atcgtcacgc gattag                                                              16

SEQ ID NO: 36            moltype = DNA   length = 16
FEATURE                  Location/Qualifiers
source                   1..16
                         mol_type = other DNA
                         organism = synthetic construct SEQUENCE: 36
gccaatcgac gttagt                                                              16

SEQ ID NO: 37            moltype = DNA   length = 16
FEATURE                  Location/Qualifiers
source                   1..16
                         mol_type = other DNA
                         organism = synthetic construct SEQUENCE: 37
ttagcgcgcg aattac                                                              16

SEQ ID NO: 38            moltype = DNA   length = 16
FEATURE                  Location/Qualifiers
source                   1..16
                         mol_type = other DNA
                         organism = synthetic construct SEQUENCE: 38
tcgatcagtt acgcga                                                              16

SEQ ID NO: 39            moltype = DNA   length = 16
FEATURE                  Location/Qualifiers
source                   1..16
                         mol_type = other DNA
                         organism = synthetic construct SEQUENCE: 39
acctgaatac gcggtt                                                              16

SEQ ID NO: 40            moltype = DNA   length = 16
FEATURE                  Location/Qualifiers
source                   1..16
                         mol_type = other DNA
                         organism = synthetic construct SEQUENCE: 40
tgcggtcgaa cctaat                                                              16

SEQ ID NO: 41            moltype = DNA   length = 16
FEATURE                  Location/Qualifiers
source                   1..16
                         mol_type = other DNA
                         organism = synthetic construct SEQUENCE: 41
tgaacgcgct actatg                                                              16

SEQ ID NO: 42            moltype = DNA   length = 16
FEATURE                  Location/Qualifiers
source                   1..16
                         mol_type = other DNA
                         organism = synthetic construct SEQUENCE: 42
tggcttaatc gcgaca                                                              16

SEQ ID NO: 43            moltype = DNA   length = 16
FEATURE                  Location/Qualifiers
source                   1..16
                         mol_type = other DNA
                         organism = synthetic construct

```
SEQUENCE: 43
taggtccgcg acatta                                                    16

SEQ ID NO: 44           moltype = DNA   length = 16
FEATURE                 Location/Qualifiers
source                  1..16
                        mol_type = other DNA
                        organism = synthetic construct SEQUENCE: 44
ccttggcgaa cgatta                                                    16

SEQ ID NO: 45           moltype = DNA   length = 16
FEATURE                 Location/Qualifiers
source                  1..16
                        mol_type = other DNA
                        organism = synthetic construct SEQUENCE: 45
aagtccgcgc gattat                                                    16

SEQ ID NO: 46           moltype = DNA   length = 16
FEATURE                 Location/Qualifiers
source                  1..16
                        mol_type = other DNA
                        organism = synthetic construct SEQUENCE: 46
gactgtcgcg caatta                                                    16

SEQ ID NO: 47           moltype = DNA   length = 16
FEATURE                 Location/Qualifiers
source                  1..16
                        mol_type = other DNA
                        organism = synthetic construct SEQUENCE: 47
ttaggtccgc tacgaa                                                    16

SEQ ID NO: 48           moltype = DNA   length = 16
FEATURE                 Location/Qualifiers
source                  1..16
                        mol_type = other DNA
                        organism = synthetic construct SEQUENCE: 48
tctgtgaacc gtcgaa                                                    16

SEQ ID NO: 49           moltype = DNA   length = 16
FEATURE                 Location/Qualifiers
source                  1..16
                        mol_type = other DNA
                        organism = synthetic construct SEQUENCE: 49
gtcacaatac gcggtt                                                    16

SEQ ID NO: 50           moltype = DNA   length = 16
FEATURE                 Location/Qualifiers
source                  1..16
                        mol_type = other DNA
                        organism = synthetic construct SEQUENCE: 50
gagacttcgc gcatta                                                    16

SEQ ID NO: 51           moltype = DNA   length = 16
FEATURE                 Location/Qualifiers
source                  1..16
                        mol_type = other DNA
                        organism = synthetic construct SEQUENCE: 51
gagcaattcg cgctat                                                    16

SEQ ID NO: 52           moltype = DNA   length = 16
FEATURE                 Location/Qualifiers
source                  1..16
                        mol_type = other DNA
                        organism = synthetic construct SEQUENCE: 52
cgttacgatt acgcga                                                    16

SEQ ID NO: 53           moltype = DNA   length = 16
FEATURE                 Location/Qualifiers
source                  1..16
                        mol_type = other DNA
```

-continued

```
SEQUENCE: 53
agcacgtaat cgttcg                                                16

SEQ ID NO: 54          moltype = DNA  length = 16
FEATURE                Location/Qualifiers
source                 1..16
                       mol_type = other DNA
                       organism = synthetic construct
SEQUENCE: 54
gcgttaccga acgtat                                                16

SEQ ID NO: 55          moltype = DNA  length = 16
FEATURE                Location/Qualifiers
source                 1..16
                       mol_type = other DNA
                       organism = synthetic construct
SEQUENCE: 55
ttaacgaccg gttacg                                                16

SEQ ID NO: 56          moltype = DNA  length = 16
FEATURE                Location/Qualifiers
source                 1..16
                       mol_type = other DNA
                       organism = synthetic construct
SEQUENCE: 56
attgcgcgcg atacta                                                16

SEQ ID NO: 57          moltype = DNA  length = 16
FEATURE                Location/Qualifiers
source                 1..16
                       mol_type = other DNA
                       organism = synthetic construct
SEQUENCE: 57
ctgttgaccg cgaata                                                16

SEQ ID NO: 58          moltype = DNA  length = 16
FEATURE                Location/Qualifiers
source                 1..16
                       mol_type = other DNA
                       organism = synthetic construct
SEQUENCE: 58
gcaagattcg cgctat                                                16

SEQ ID NO: 59          moltype = DNA  length = 16
FEATURE                Location/Qualifiers
source                 1..16
                       mol_type = other DNA
                       organism = synthetic construct
SEQUENCE: 59
ggccatcgcg aattat                                                16

SEQ ID NO: 60          moltype = DNA  length = 16
FEATURE                Location/Qualifiers
source                 1..16
                       mol_type = other DNA
                       organism = synthetic construct
SEQUENCE: 60
atggaccgcg ctatta                                                16

SEQ ID NO: 61          moltype = DNA  length = 16
FEATURE                Location/Qualifiers
source                 1..16
                       mol_type = other DNA
                       organism = synthetic construct
SEQUENCE: 61
acgcgataat cgttcg                                                16

SEQ ID NO: 62          moltype = DNA  length = 16
FEATURE                Location/Qualifiers
source                 1..16
                       mol_type = other DNA
                       organism = synthetic construct
SEQUENCE: 62
taggcattat ccgcga                                                16

SEQ ID NO: 63          moltype = DNA  length = 16
FEATURE                Location/Qualifiers
source                 1..16
```

```
                              mol_type = other DNA
                              organism = synthetic construct
SEQUENCE: 63
tcagctcgaa cggtta                                                    16

SEQ ID NO: 64                 moltype = DNA   length = 16
FEATURE                       Location/Qualifiers
source                        1..16
                              mol_type = other DNA
                              organism = synthetic construct
SEQUENCE: 64
cattcaattg cgcgag                                                    16

SEQ ID NO: 65                 moltype = DNA   length = 16
FEATURE                       Location/Qualifiers
source                        1..16
                              mol_type = other DNA
                              organism = synthetic construct
SEQUENCE: 65
gctcaattac gcggat                                                    16

SEQ ID NO: 66                 moltype = DNA   length = 16
FEATURE                       Location/Qualifiers
source                        1..16
                              mol_type = other DNA
                              organism = synthetic construct
SEQUENCE: 66
acggatcgca tcgtta                                                    16

SEQ ID NO: 67                 moltype = DNA   length = 16
FEATURE                       Location/Qualifiers
source                        1..16
                              mol_type = other DNA
                              organism = synthetic construct
SEQUENCE: 67
ctgcaattac gcggat                                                    16

SEQ ID NO: 68                 moltype = DNA   length = 16
FEATURE                       Location/Qualifiers
source                        1..16
                              mol_type = other DNA
                              organism = synthetic construct
SEQUENCE: 68
tgtcgattac gcgaac                                                    16

SEQ ID NO: 69                 moltype = DNA   length = 16
FEATURE                       Location/Qualifiers
source                        1..16
                              mol_type = other DNA
                              organism = synthetic construct
SEQUENCE: 69
acctaggcgc gattat                                                    16

SEQ ID NO: 70                 moltype = DNA   length = 16
FEATURE                       Location/Qualifiers
source                        1..16
                              mol_type = other DNA
                              organism = synthetic construct
SEQUENCE: 70
cgcgtagcgc atatta                                                    16

SEQ ID NO: 71                 moltype = DNA   length = 16
FEATURE                       Location/Qualifiers
source                        1..16
                              mol_type = other DNA
                              organism = synthetic construct
SEQUENCE: 71
caatcgttac gcggat                                                    16

SEQ ID NO: 72                 moltype = DNA   length = 16
FEATURE                       Location/Qualifiers
source                        1..16
                              mol_type = other DNA
                              organism = synthetic construct
SEQUENCE: 72
taacgcttac gcggat                                                    16

SEQ ID NO: 73                 moltype = DNA   length = 16
FEATURE                       Location/Qualifiers
```

```
source                      1..16
                            mol_type = other DNA
                            organism = synthetic construct
SEQUENCE: 73
gctaacgcga ttcgta                                                           16

SEQ ID NO: 74               moltype = DNA   length = 16
FEATURE                     Location/Qualifiers
source                      1..16
                            mol_type = other DNA
                            organism = synthetic construct
SEQUENCE: 74
attcctaatg cgcgag                                                           16

SEQ ID NO: 75               moltype = DNA   length = 16
FEATURE                     Location/Qualifiers
source                      1..16
                            mol_type = other DNA
                            organism = synthetic construct
SEQUENCE: 75
ttcactaatg cgcgag                                                           16

SEQ ID NO: 76               moltype = DNA   length = 16
FEATURE                     Location/Qualifiers
source                      1..16
                            mol_type = other DNA
                            organism = synthetic construct
SEQUENCE: 76
caaggattcg cgctat                                                           16

SEQ ID NO: 77               moltype = DNA   length = 16
FEATURE                     Location/Qualifiers
source                      1..16
                            mol_type = other DNA
                            organism = synthetic construct
SEQUENCE: 77
acgattcgac cggtat                                                           16

SEQ ID NO: 78               moltype = DNA   length = 16
FEATURE                     Location/Qualifiers
source                      1..16
                            mol_type = other DNA
                            organism = synthetic construct
SEQUENCE: 78
gagcaactat tcgcgt                                                           16

SEQ ID NO: 79               moltype = DNA   length = 16
FEATURE                     Location/Qualifiers
source                      1..16
                            mol_type = other DNA
                            organism = synthetic construct
SEQUENCE: 79
tacctacgat tgcgag                                                           16

SEQ ID NO: 80               moltype = DNA   length = 16
FEATURE                     Location/Qualifiers
source                      1..16
                            mol_type = other DNA
                            organism = synthetic construct
SEQUENCE: 80
taatcgaccg gttacg                                                           16

SEQ ID NO: 81               moltype = DNA   length = 16
FEATURE                     Location/Qualifiers
source                      1..16
                            mol_type = other DNA
                            organism = synthetic construct
SEQUENCE: 81
gttcacaata cgcggt                                                           16

SEQ ID NO: 82               moltype = DNA   length = 16
FEATURE                     Location/Qualifiers
source                      1..16
                            mol_type = other DNA
                            organism = synthetic construct
SEQUENCE: 82
gctagcgcgc atatta                                                           16

SEQ ID NO: 83               moltype = DNA   length = 16
```

```
FEATURE                Location/Qualifiers
source                 1..16
                       mol_type = other DNA
                       organism = synthetic construct
SEQUENCE: 83
actgacttac gcggat                                                16

SEQ ID NO: 84          moltype = DNA  length = 16
FEATURE                Location/Qualifiers
source                 1..16
                       mol_type = other DNA
                       organism = synthetic construct
SEQUENCE: 84
gcacgttcgc gtaata                                                16

SEQ ID NO: 85          moltype = DNA  length = 16
FEATURE                Location/Qualifiers
source                 1..16
                       mol_type = other DNA
                       organism = synthetic construct
SEQUENCE: 85
aaggtccgcg ctatta                                                16

SEQ ID NO: 86          moltype = DNA  length = 16
FEATURE                Location/Qualifiers
source                 1..16
                       mol_type = other DNA
                       organism = synthetic construct
SEQUENCE: 86
ctagtgaacg cgctat                                                16

SEQ ID NO: 87          moltype = DNA  length = 16
FEATURE                Location/Qualifiers
source                 1..16
                       mol_type = other DNA
                       organism = synthetic construct
SEQUENCE: 87
ggccatcgat tcgtaa                                                16

SEQ ID NO: 88          moltype = DNA  length = 16
FEATURE                Location/Qualifiers
source                 1..16
                       mol_type = other DNA
                       organism = synthetic construct
SEQUENCE: 88
accttgcgcg atagta                                                16

SEQ ID NO: 89          moltype = DNA  length = 16
FEATURE                Location/Qualifiers
source                 1..16
                       mol_type = other DNA
                       organism = synthetic construct
SEQUENCE: 89
ctaggtccgc gaatta                                                16

SEQ ID NO: 90          moltype = DNA  length = 16
FEATURE                Location/Qualifiers
source                 1..16
                       mol_type = other DNA
                       organism = synthetic construct
SEQUENCE: 90
atatcgaccg gttacg                                                16

SEQ ID NO: 91          moltype = DNA  length = 16
FEATURE                Location/Qualifiers
source                 1..16
                       mol_type = other DNA
                       organism = synthetic construct
SEQUENCE: 91
atagcttatg cgcgac                                                16

SEQ ID NO: 92          moltype = DNA  length = 16
FEATURE                Location/Qualifiers
source                 1..16
                       mol_type = other DNA
                       organism = synthetic construct
SEQUENCE: 92
acgttaatcg gtacgc                                                16
```

| | | |
|---|---|---|
| SEQ ID NO: 93<br>FEATURE<br>source | moltype = DNA   length = 16<br>Location/Qualifiers<br>1..16<br>mol_type = other DNA<br>organism = synthetic construct | |
| SEQUENCE: 93<br>catcatcgat tgcgag | | 16 |
| SEQ ID NO: 94<br>FEATURE<br>source | moltype = DNA   length = 16<br>Location/Qualifiers<br>1..16<br>mol_type = other DNA<br>organism = synthetic construct | |
| SEQUENCE: 94<br>gtaactcgac cggatt | | 16 |
| SEQ ID NO: 95<br>FEATURE<br>source | moltype = DNA   length = 16<br>Location/Qualifiers<br>1..16<br>mol_type = other DNA<br>organism = synthetic construct | |
| SEQUENCE: 95<br>tcgaacgcgt attagc | | 16 |
| SEQ ID NO: 96<br>FEATURE<br>source | moltype = DNA   length = 16<br>Location/Qualifiers<br>1..16<br>mol_type = other DNA<br>organism = synthetic construct | |
| SEQUENCE: 96<br>tagtcgaccg attacg | | 16 |
| SEQ ID NO: 97<br>FEATURE<br>source | moltype = DNA   length = 16<br>Location/Qualifiers<br>1..16<br>mol_type = other DNA<br>organism = synthetic construct | |
| SEQUENCE: 97<br>gatcacgcga ttcgta | | 16 |
| SEQ ID NO: 98<br>FEATURE<br>source | moltype = DNA   length = 16<br>Location/Qualifiers<br>1..16<br>mol_type = other DNA<br>organism = synthetic construct | |
| SEQUENCE: 98<br>agttagcgtt acgacc | | 16 |
| SEQ ID NO: 99<br>FEATURE<br>source | moltype = DNA   length = 16<br>Location/Qualifiers<br>1..16<br>mol_type = other DNA<br>organism = synthetic construct | |
| SEQUENCE: 99<br>gctcaataag tcgcgt | | 16 |
| SEQ ID NO: 100<br>FEATURE<br>source | moltype = DNA   length = 16<br>Location/Qualifiers<br>1..16<br>mol_type = other DNA<br>organism = synthetic construct | |
| SEQUENCE: 100<br>cttaggcgcg aattac | | 16 |
| SEQ ID NO: 101<br>FEATURE<br>source | moltype = DNA   length = 16<br>Location/Qualifiers<br>1..16<br>mol_type = other DNA<br>organism = synthetic construct | |
| SEQUENCE: 101<br>taggtcacgt tacgac | | 16 |
| SEQ ID NO: 102<br>FEATURE<br>source | moltype = DNA   length = 16<br>Location/Qualifiers<br>1..16<br>mol_type = other DNA<br>organism = synthetic construct | |
| SEQUENCE: 102<br>ataccttatg cgcgag | | 16 |

SEQ ID NO: 103      moltype = DNA   length = 16
FEATURE             Location/Qualifiers
source              1..16
                    mol_type = other DNA
                    organism = synthetic construct
SEQUENCE: 103
gcacgatagt tcgcta                                                          16

SEQ ID NO: 104      moltype = DNA   length = 16
FEATURE             Location/Qualifiers
source              1..16
                    mol_type = other DNA
                    organism = synthetic construct
SEQUENCE: 104
gtcatacaat tcgcgg                                                          16

SEQ ID NO: 105      moltype = DNA   length = 16
FEATURE             Location/Qualifiers
source              1..16
                    mol_type = other DNA
                    organism = synthetic construct
SEQUENCE: 105
cgactattat gcgcga                                                          16

SEQ ID NO: 106      moltype = DNA   length = 16
FEATURE             Location/Qualifiers
source              1..16
                    mol_type = other DNA
                    organism = synthetic construct
SEQUENCE: 106
taagccgcgt attagc                                                          16

SEQ ID NO: 107      moltype = DNA   length = 16
FEATURE             Location/Qualifiers
source              1..16
                    mol_type = other DNA
                    organism = synthetic construct
SEQUENCE: 107
cgaattcgac cggtat                                                          16

SEQ ID NO: 108      moltype = DNA   length = 16
FEATURE             Location/Qualifiers
source              1..16
                    mol_type = other DNA
                    organism = synthetic construct
SEQUENCE: 108
cgtcaataat cgcgtg                                                          16

SEQ ID NO: 109      moltype = DNA   length = 16
FEATURE             Location/Qualifiers
source              1..16
                    mol_type = other DNA
                    organism = synthetic construct
SEQUENCE: 109
ggaaccttaa tcgcgt                                                          16

SEQ ID NO: 110      moltype = DNA   length = 16
FEATURE             Location/Qualifiers
source              1..16
                    mol_type = other DNA
                    organism = synthetic construct
SEQUENCE: 110
gctcaataat cgcgtg                                                          16

SEQ ID NO: 111      moltype = DNA   length = 16
FEATURE             Location/Qualifiers
source              1..16
                    mol_type = other DNA
                    organism = synthetic construct
SEQUENCE: 111
ccaatgcgcg ttagta                                                          16

SEQ ID NO: 112      moltype = DNA   length = 16
FEATURE             Location/Qualifiers
source              1..16
                    mol_type = other DNA
                    organism = synthetic construct
SEQUENCE: 112

```
gaacttcgac cggtat                                                        16

SEQ ID NO: 113          moltype = DNA   length = 16
FEATURE                 Location/Qualifiers
source                  1..16
                        mol_type = other DNA
                        organism = synthetic construct SEQUENCE: 113
cgcttaatcg aacggt                                                        16

SEQ ID NO: 114          moltype = DNA   length = 16
FEATURE                 Location/Qualifiers
source                  1..16
                        mol_type = other DNA
                        organism = synthetic construct SEQUENCE: 114
ccttgagtcg aacgat                                                        16

SEQ ID NO: 115          moltype = DNA   length = 16
FEATURE                 Location/Qualifiers
source                  1..16
                        mol_type = other DNA
                        organism = synthetic construct SEQUENCE: 115
atcgagtaac cgttcg                                                        16

SEQ ID NO: 116          moltype = DNA   length = 16
FEATURE                 Location/Qualifiers
source                  1..16
                        mol_type = other DNA
                        organism = synthetic construct SEQUENCE: 116
taccgtaacg tagtcg                                                        16

SEQ ID NO: 117          moltype = DNA   length = 16
FEATURE                 Location/Qualifiers
source                  1..16
                        mol_type = other DNA
                        organism = synthetic construct SEQUENCE: 117
gttctcatcg aacgga                                                        16

SEQ ID NO: 118          moltype = DNA   length = 16
FEATURE                 Location/Qualifiers
source                  1..16
                        mol_type = other DNA
                        organism = synthetic construct SEQUENCE: 118
atcttgaatc gcgacg                                                        16

SEQ ID NO: 119          moltype = DNA   length = 16
FEATURE                 Location/Qualifiers
source                  1..16
                        mol_type = other DNA
                        organism = synthetic construct SEQUENCE: 119
agaccttaat cgcgtg                                                        16

SEQ ID NO: 120          moltype = DNA   length = 16
FEATURE                 Location/Qualifiers
source                  1..16
                        mol_type = other DNA
                        organism = synthetic construct SEQUENCE: 120
gaccaatatg tcgcgt                                                        16

SEQ ID NO: 121          moltype = DNA   length = 16
FEATURE                 Location/Qualifiers
source                  1..16
                        mol_type = other DNA
                        organism = synthetic construct SEQUENCE: 121
cgtaatcgac cggtat                                                        16

SEQ ID NO: 122          moltype = DNA   length = 16
FEATURE                 Location/Qualifiers
source                  1..16
                        mol_type = other DNA
                        organism = synthetic construct
```

```
SEQUENCE: 122
gtacactaag tcgcgt                                                          16

SEQ ID NO: 123          moltype = DNA   length = 16
FEATURE                 Location/Qualifiers
source                  1..16
                        mol_type = other DNA
                        organism = synthetic construct
SEQUENCE: 123
tagtaccgat tgaccg                                                          16

SEQ ID NO: 124          moltype = DNA   length = 16
FEATURE                 Location/Qualifiers
source                  1..16
                        mol_type = other DNA
                        organism = synthetic construct
SEQUENCE: 124
agtctaatcg gtacgc                                                          16

SEQ ID NO: 125          moltype = DNA   length = 16
FEATURE                 Location/Qualifiers
source                  1..16
                        mol_type = other DNA
                        organism = synthetic construct
SEQUENCE: 125
gtactgaccg attacg                                                          16

SEQ ID NO: 126          moltype = DNA   length = 16
FEATURE                 Location/Qualifiers
source                  1..16
                        mol_type = other DNA
                        organism = synthetic construct
SEQUENCE: 126
ccttgaatcg aacggt                                                          16

SEQ ID NO: 127          moltype = DNA   length = 16
FEATURE                 Location/Qualifiers
source                  1..16
                        mol_type = other DNA
                        organism = synthetic construct
SEQUENCE: 127
tcgactaatc ggtacg                                                          16

SEQ ID NO: 128          moltype = DNA   length = 16
FEATURE                 Location/Qualifiers
source                  1..16
                        mol_type = other DNA
                        organism = synthetic construct
SEQUENCE: 128
gcggattacg ctacta                                                          16

SEQ ID NO: 129          moltype = DNA   length = 16
FEATURE                 Location/Qualifiers
source                  1..16
                        mol_type = other DNA
                        organism = synthetic construct
SEQUENCE: 129
ccttagtagt acgcga                                                          16

SEQ ID NO: 130          moltype = DNA   length = 16
FEATURE                 Location/Qualifiers
source                  1..16
                        mol_type = other DNA
                        organism = synthetic construct
SEQUENCE: 130
ccttaagtta cgcgag                                                          16

SEQ ID NO: 131          moltype = DNA   length = 16
FEATURE                 Location/Qualifiers
source                  1..16
                        mol_type = other DNA
                        organism = synthetic construct
SEQUENCE: 131
gtaagtacgc gctatc                                                          16

SEQ ID NO: 132          moltype = DNA   length = 16
FEATURE                 Location/Qualifiers
source                  1..16
                        mol_type = other DNA
```

-continued

```
SEQUENCE: 132
ctgtcgcgat cgataa                                                   16

SEQ ID NO: 133          moltype = DNA   length = 16
FEATURE                 Location/Qualifiers
source                  1..16
                        mol_type = other DNA
                        organism = synthetic construct
SEQUENCE: 133
ggacaatcgc tcgtta                                                   16

SEQ ID NO: 134          moltype = DNA   length = 16
FEATURE                 Location/Qualifiers
source                  1..16
                        mol_type = other DNA
                        organism = synthetic construct
SEQUENCE: 134
gtccgtcgat cgataa                                                   16

SEQ ID NO: 135          moltype = DNA   length = 16
FEATURE                 Location/Qualifiers
source                  1..16
                        mol_type = other DNA
                        organism = synthetic construct
SEQUENCE: 135
gacttacgac cggtat                                                   16

SEQ ID NO: 136          moltype = DNA   length = 16
FEATURE                 Location/Qualifiers
source                  1..16
                        mol_type = other DNA
                        organism = synthetic construct
SEQUENCE: 136
ctgttaatcg accgga                                                   16

SEQ ID NO: 137          moltype = DNA   length = 16
FEATURE                 Location/Qualifiers
source                  1..16
                        mol_type = other DNA
                        organism = synthetic construct
SEQUENCE: 137
atgcggtaac ctatcg                                                   16

SEQ ID NO: 138          moltype = DNA   length = 16
FEATURE                 Location/Qualifiers
source                  1..16
                        mol_type = other DNA
                        organism = synthetic construct
SEQUENCE: 138
agatagttac gcgtcc                                                   16

SEQ ID NO: 139          moltype = DNA   length = 16
FEATURE                 Location/Qualifiers
source                  1..16
                        mol_type = other DNA
                        organism = synthetic construct
SEQUENCE: 139
gagtccaact atcggt                                                   16

SEQ ID NO: 140          moltype = DNA   length = 16
FEATURE                 Location/Qualifiers
source                  1..16
                        mol_type = other DNA
                        organism = synthetic construct
SEQUENCE: 140
ttacagtact agcggc                                                   16

SEQ ID NO: 141          moltype = DNA   length = 16
FEATURE                 Location/Qualifiers
source                  1..16
                        mol_type = other DNA
                        organism = synthetic construct
SEQUENCE: 141
gactaatacg cgttcg                                                   16

SEQ ID NO: 142          moltype = DNA   length = 16
FEATURE                 Location/Qualifiers
source                  1..16
```

```
                        mol_type = other DNA
                        organism = synthetic construct
SEQUENCE: 142
tggtaactat accggc                                                   16

SEQ ID NO: 143          moltype = DNA   length = 16
FEATURE                 Location/Qualifiers
source                  1..16
                        mol_type = other DNA
                        organism = synthetic construct
SEQUENCE: 143
cgtacgtaac tatcgg                                                   16

SEQ ID NO: 144          moltype = DNA   length = 16
FEATURE                 Location/Qualifiers
source                  1..16
                        mol_type = other DNA
                        organism = synthetic construct
SEQUENCE: 144
gaccttaatc ggtacg                                                   16

SEQ ID NO: 145          moltype = DNA   length = 16
FEATURE                 Location/Qualifiers
source                  1..16
                        mol_type = other DNA
                        organism = synthetic construct
SEQUENCE: 145
cattaccgga tagtcg                                                   16

SEQ ID NO: 146          moltype = DNA   length = 16
FEATURE                 Location/Qualifiers
source                  1..16
                        mol_type = other DNA
                        organism = synthetic construct
SEQUENCE: 146
gatagttatc gcaccg                                                   16

SEQ ID NO: 147          moltype = DNA   length = 16
FEATURE                 Location/Qualifiers
source                  1..16
                        mol_type = other DNA
                        organism = synthetic construct
SEQUENCE: 147
actagtcgta cgatgc                                                   16

SEQ ID NO: 148          moltype = DNA   length = 16
FEATURE                 Location/Qualifiers
source                  1..16
                        mol_type = other DNA
                        organism = synthetic construct
SEQUENCE: 148
gatcactaat cgcgtg                                                   16

SEQ ID NO: 149          moltype = DNA   length = 16
FEATURE                 Location/Qualifiers
source                  1..16
                        mol_type = other DNA
                        organism = synthetic construct
SEQUENCE: 149
gcgttacgct aatacg                                                   16

SEQ ID NO: 150          moltype = DNA   length = 16
FEATURE                 Location/Qualifiers
source                  1..16
                        mol_type = other DNA
                        organism = synthetic construct
SEQUENCE: 150
cacgatcgta cggtat                                                   16

SEQ ID NO: 151          moltype = DNA   length = 16
FEATURE                 Location/Qualifiers
source                  1..16
                        mol_type = other DNA
                        organism = synthetic construct
SEQUENCE: 151
tgtacgtacg atccga                                                   16

SEQ ID NO: 152          moltype = DNA   length = 16
FEATURE                 Location/Qualifiers
```

```
source                   1..16
                         mol_type = other DNA
                         organism = synthetic construct
SEQUENCE: 152
ctagactaat cgcgtg                                                         16

SEQ ID NO: 153           moltype = DNA   length = 16
FEATURE                  Location/Qualifiers
source                   1..16
                         mol_type = other DNA
                         organism = synthetic construct
SEQUENCE: 153
catagtcgta cgatgc                                                         16

SEQ ID NO: 154           moltype = DNA   length = 16
FEATURE                  Location/Qualifiers
source                   1..16
                         mol_type = other DNA
                         organism = synthetic construct
SEQUENCE: 154
gtcgactaac tatcgg                                                         16

SEQ ID NO: 155           moltype = DNA   length = 22
FEATURE                  Location/Qualifiers
source                   1..22
                         mol_type = other DNA
                         organism = synthetic construct
SEQUENCE: 155
ccttagccgc taataggtga gc                                                  22

SEQ ID NO: 156           moltype = DNA   length = 22
FEATURE                  Location/Qualifiers
source                   1..22
                         mol_type = other DNA
                         organism = synthetic construct
SEQUENCE: 156
ttgctaggac cggccttaaa gc                                                  22

SEQ ID NO: 157           moltype = DNA   length = 22
FEATURE                  Location/Qualifiers
source                   1..22
                         mol_type = other DNA
                         organism = synthetic construct
SEQUENCE: 157
gaggattgcg caccttacta gc                                                  22

SEQ ID NO: 158           moltype = DNA   length = 22
FEATURE                  Location/Qualifiers
source                   1..22
                         mol_type = other DNA
                         organism = synthetic construct
SEQUENCE: 158
caactttagc ggtccaaggt gc                                                  22

SEQ ID NO: 159           moltype = DNA   length = 22
FEATURE                  Location/Qualifiers
source                   1..22
                         mol_type = other DNA
                         organism = synthetic construct
SEQUENCE: 159
acgctagttt cgcgtacgaa gc                                                  22

SEQ ID NO: 160           moltype = DNA   length = 22
FEATURE                  Location/Qualifiers
source                   1..22
                         mol_type = other DNA
                         organism = synthetic construct
SEQUENCE: 160
acgctagttt cgcgtacgaa gc                                                  22

SEQ ID NO: 161           moltype = DNA   length = 22
FEATURE                  Location/Qualifiers
source                   1..22
                         mol_type = other DNA
                         organism = synthetic construct
SEQUENCE: 161
gaggattgcg caccttacta gc                                                  22

SEQ ID NO: 162           moltype = DNA   length = 22
```

-continued

```
FEATURE             Location/Qualifiers
source              1..22
                    mol_type = other DNA
                    organism = synthetic construct
SEQUENCE: 162
ttgctaggac cggccttaaa gc                                         22

SEQ ID NO: 163      moltype = DNA  length = 22
FEATURE             Location/Qualifiers
source              1..22
                    mol_type = other DNA
                    organism = synthetic construct
SEQUENCE: 163
gacaattgtc ggctcgacta gc                                         22

SEQ ID NO: 164      moltype = DNA  length = 32
FEATURE             Location/Qualifiers
source              1..32
                    mol_type = other DNA
                    organism = synthetic construct
misc_difference     32
                    note = a, c, t or g
SEQUENCE: 164
tttttttttt tttttttttt tttttttttt vn                              32

SEQ ID NO: 165      moltype = DNA  length = 52
FEATURE             Location/Qualifiers
source              1..52
                    mol_type = other DNA
                    organism = synthetic construct
misc_difference     1..20
                    note = a, c, t or g
misc_difference     52
                    note = a, c, t or g
SEQUENCE: 165
nnnnnnnnnn nnnnnnnnnn tttttttttt tttttttttt tttttttttt vn        52
```

SYSTEMS AND METHODS FOR SAMPLE ANALYSIS

CROSS-REFERENCE

This application is a continuation of U.S. application Ser. No. 16/737,762, filed Jan. 8, 2020, which claims the benefit of U.S. Provisional Patent Application No. 62/789,893, filed Jan. 8, 2019.

SEQUENCE LISTING

The instant application contains a Sequence Listing which has been submitted electronically in XML file format and is hereby incorporated by reference in its entirety. The XML copy, created on Oct. 17, 2023, is named 43487-836_501_SL.xml and is 146,767 bytes in size.

BACKGROUND

A sample may be processed for various purposes, such as identification of a type of moiety within the sample. The sample may be a biological sample. Biological samples may be processed, such as for detection of a disease (e.g., cancer) or identification of a particular species. There are various approaches for processing samples, such as polymerase chain reaction (PCR) and sequencing.

Biological samples may be processed within various reaction environments, such as partitions. Partitions may be wells or droplets. Droplets or wells may be employed to process biological samples in a manner that enables the biological samples to be partitioned and processed separately. For example, such droplets may be fluidically isolated from other droplets, enabling accurate control of respective environments in the droplets.

Biological samples in partitions may be subjected to various processes, such as chemical processes or physical processes. Samples in partitions may be subjected to heating or cooling, or chemical reactions, such as to yield species that may be qualitatively or quantitatively processed.

SUMMARY

The present disclosure provides methods for use in various sample processing and analysis applications. The methods provided herein may provide barcode molecules comprising one or more sequences such as a barcode sequence and a non-target-specific overhang sequence. Barcode molecules may be attached to supports such as beads. Such methods may employ combinatorial (e.g., split pool) ligation reactions and may be useful, for example, in controlled analysis and processing of analytes such as biological particles, nucleic acid molecules, proteins, and perturbation agents, or the detection of genomic edits.

In an aspect, the present disclosure provides a method for generating a functionalized barcoded molecule, comprising: providing a bead having attached thereto a barcode molecule comprising a barcode sequence and a non-target-specific sequence, which non-target-specific sequence terminates at or in proximity to a 3' end of the barcode molecule, wherein the barcode molecule is not configured to conduct a chemical or biological reaction on a biological analyte; and bringing the barcode molecule in contact with a functionalizing molecule comprising (i) a sequence complementary to the non-target-specific sequence and (ii) a functional moiety, under conditions sufficient to permit the sequence to hybridize to the non-target-specific sequence, to thereby yield the functionalized barcode molecule comprising the functional moiety, which functionalized barcode molecule is configured to conduct the chemical or biological reaction on the biological analyte.

In some embodiments, the barcode molecule comprises a double-stranded portion and a single stranded portion. In some cases, the double-stranded portion comprises the barcode sequence and the single-stranded portion comprises the non-target-specific sequence.

In some embodiments, the method further comprises, subsequent to bringing the barcode molecule in contact with a functionalizing molecule, ligating the sequence that is complementary to the non-target-specific sequence to a strand of the double-stranded portion.

In some embodiments, the sequence is ligated through chemical ligation. In some cases, the chemical ligation comprises formation of a triazole bond between the sequence and the strand. In some cases, the chemical ligation comprises formation of a phosphorothioate bond between the sequence and the strand. In some cases, the chemical ligation comprises formation of an amide bond between the sequence and the strand.

In some embodiments, the bead is a gel bead. In some cases, the barcode molecule is releasably attached to the gel bead. In some cases, the functionalized barcode molecule is releasably attached to the gel bead.

In some embodiments, the functional moiety comprises a unique molecular identifier. In some cases, the functional moiety comprises a target specific sequence, wherein said target-specific sequence is complementary to a sequence of said biological analyte. In some cases, the functional moiety comprises a target specific sequence, wherein said target-specific sequence is complementary to a sequence of an assay molecule, wherein the assay molecule can be bound to said biological analyte. In some cases, the functional moiety comprises a non-target-specific sequence, wherein said non-target-specific sequence is complementary to a sequence of said biological analyte. In some cases, the functional moiety comprises a non-target-specific sequence, wherein said non-target-specific sequence is complementary to a sequence of an assay molecule, wherein said assay molecule can be bound to said biological analyte. In some cases, the functional moiety comprises a blunt end, wherein said blunt end can be ligated to said biological analyte. In some cases, the functional moiety comprises a sticky end, wherein said sticky end can be ligated to said biological analyte.

In some cases, the biological analyte comprises a deoxyribonucleic acid-conjugated antibody. In some cases, the biological analyte comprises a guide ribonucleic acid (RNA) barcode.

In some cases, the biological analyte is a ribonucleic acid (RNA) molecule, and wherein the functional moiety comprises a target-specific sequence, and wherein the target-specific sequence is complementary to the RNA molecule. In some cases, the target sequence is a poly-T sequence. In some cases, the biological analyte is a deoxyribonucleic acid (DNA) molecule, and wherein the target-specific sequence of the functional moiety is complementary to the DNA molecule.

In some embodiments, bringing the barcode molecule in contact with a functionalizing molecule is performed in bulk. In some embodiments, it is performed in a partition of a plurality of partitions. In some cases, the partition is a droplet. In some cases, the partition is a well. In some cases, it is performed in a reaction vessel having the biological analyte.

In some embodiments, the method further comprises, subsequent to bringing the barcode molecule in contact with a functionalizing molecule, bringing the functionalized barcode molecule in contact with the biological analyte.

In some embodiments, the barcode molecule is attached to the bead through one or more linkers. In some cases, the one or more linkers comprise nucleic acid molecules.

In some embodiments, the bead comprises a plurality of barcode molecules, which plurality of barcode molecules comprises the barcode molecule.

In some embodiments, the non-target-specific sequence comprises between 5 and 30 nucleotides or nucleotide analogues.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

In an aspect, disclosed herein are methods for generating a functionalized barcode molecule, comprising (a) providing a bead having attached thereto a barcode molecule comprising a barcode sequence; and (b) bringing said barcode molecule in contact with a functionalizing molecule comprising a functional sequence, under conditions sufficient to permit chemical ligation of said barcode molecule to said functionalizing molecule to thereby yield said functionalized barcode molecule comprising said functional sequence.

In some embodiments, said barcode molecule comprises a first functional group and said functionalizing molecule comprises a second functional group, and wherein said chemical ligation comprises formation of a chemical bond between said first and second functional group.

In some embodiments, said chemical ligation comprises formation of a triazole bond between said functionalizing molecule and said barcode molecule. In some embodiments, said chemical ligation comprises formation of a phosphorothioate bond between said functionalizing molecule and said barcode molecule. In some embodiments, said chemical ligation comprises formation of an amide bond between said functionalizing molecule and said barcode molecule.

In some embodiments, said functionalizing molecule is ligated to a 3' region of said barcode molecule. In some embodiments, said functionalizing molecule is ligated to a 5' region of said barcode molecule.

In some embodiments, said barcode molecule further comprises an additional sequence selected from the group consisting of: a sequence for permitting said barcoded nucleic acid molecule or a derivative thereof to couple to a flow cell of a sequencer, an adapter sequence, an unique molecular identifier, a primer sequence, a primer binding sequence, and any combination thereof.

In some embodiments, said functional sequence comprises a sequence selected from the group consisting of: a unique molecular identifier sequence, an adapter sequence, a primer sequence, a primer binding sequence, a target-specific sequence, a non-target-specific sequence, and any combination thereof.

In some embodiments, said functional sequence comprises a target specific-sequence, wherein said target-specific sequence is complementary to a sequence of a biological analyte or a derivative thereof. In some embodiments, said biological analyte is a ribonucleic acid (RNA) molecule, and wherein said target-specific sequence is complementary to said RNA molecule. In some embodiments, said target-specific sequence is a poly-T sequence. In some embodiments, said biological analyte is a deoxyribonucleic acid (DNA) molecule, and wherein said target-specific sequence is complementary to said DNA molecule.

In some embodiments, said functional sequence comprises a non-target-specific sequence, wherein said non-target-specific sequence is complementary to a sequence of an assay molecule, wherein said assay molecule is configured to bind to a biological analyte.

In some embodiments, said functional sequence comprises a blunt end, wherein said blunt end can be ligated to a biological analyte. In some embodiments, said functional sequence comprises a sticky end, wherein said sticky end can be ligated to a biological analyte.

In some embodiments, said barcode molecule is not configured to conduct a chemical or biological reaction on a biological analyte. In some embodiments, said biological analyte is a deoxyribonucleic acid molecule (DNA) molecule. In some embodiments, said biological analyte is a ribonucleic acid (RNA) molecule. In some embodiments, said biological analyte is a deoxyribonucleic acid-conjugated antibody. In some embodiments, said biological analyte comprises a guide ribonucleic acid (RNA) barcode sequence.

In some embodiments, said functionalized barcode molecule is configured to conduct a chemical or biological reaction on a biological analyte. In some embodiments, (b) is performed in a bulk solution comprising a plurality of beads and a plurality of functionalizing molecules, wherein said plurality of beads comprises said bead and wherein said plurality of functionalizing molecules comprises said functionalizing molecule.

In some embodiments, (b) is performed in a partition of a plurality of partitions. In some embodiments, said partition is a droplet. In some embodiments, said partition is a well.

In some embodiments, further comprising, subsequent to (b), bringing said functionalized barcode molecule in contact with a biological analyte. In some embodiments, (b) is performed in a reaction vessel comprising a biological analyte.

In some embodiments, said barcode molecule is attached to said bead through one or more linkers. In some embodiments, in (a) said bead comprises a plurality of barcode molecules, which plurality of barcode molecules comprises said barcode molecule. In some embodiments, said bead is a gel bead. In some embodiments, said barcode molecule is releasably attached to said gel bead. In some embodiments, said functionalized barcode molecule is releasably attached to said gel bead.

In another aspect, disclosed is a method for generating a functionalized barcode molecule, comprising providing a bead having attached thereto a barcode molecule comprising a barcode sequence and a non-target-specific sequence; and bringing the barcode molecule in contact with a functionalizing molecule comprising (i) a sequence complementary to the non-target-specific sequence and (ii) a functional moiety, under conditions sufficient to permit chemical ligation of the barcode molecule to the functionalizing molecule to thereby yield the functionalized barcode molecule comprising the functional moiety.

In some embodiments, the barcode molecule is not configured to conduct a chemical or biological reaction on a biological analyte. In some embodiments, the functionalized barcode molecule is configured to conduct said chemical or biological reaction on said biological analyte.

In some embodiments, the chemical ligation comprises formation of a bond between said functionalizing molecule and said barcode molecule. In some cases, the chemical ligation comprises formation of a triazole bond between said functionalizing molecule and said barcode molecule. In some cases, the chemical ligation comprises formation of a phosphorothioate bond between said functionalizing molecule and said barcode molecule. In some cases, the chemical ligation comprises formation of an amide bond between said functionalizing molecule and said barcode molecule.

In some embodiments, in (a), the barcode molecule comprises a double-stranded portion and a single stranded portion of said barcode molecule. In some cases, the double-stranded portion comprises said barcode sequence and the single-stranded portion comprises the non-target-specific sequence. In some cases, the non-target-specific sequence is 3' of said barcode sequence. In some cases, the non-target-specific sequence is 5' of said barcode sequence. In some cases, the chemical ligation comprises ligation of said sequence complementary to said non-target-specific sequence to a strand of said double-stranded portion In some embodiments, the bead is a gel bead. In some cases, the barcode molecule is releasably attached to the gel bead. In some cases, the functionalized barcode molecule is releasably attached to the gel bead.

In some embodiments, the functional moiety comprises a unique molecular identifier. In some embodiments, the functional moiety comprises a target specific sequence, the target-specific sequence is complementary to a sequence of the biological analyte. In some embodiments, the functional moiety comprises a second non-target-specific sequence, wherein the second non-target-specific sequence is complementary to a sequence of an assay molecule, wherein the assay molecule can be bound to the biological analyte.

In some embodiments, the functional moiety comprises a blunt end, wherein the blunt end can be ligated to the biological analyte. In some embodiments, the functional moiety comprises a sticky end, wherein the sticky end can be ligated to the biological analyte.

In some embodiments, the biological analyte is a deoxyribonucleic acid-conjugated antibody. In some embodiments, the biological analyte comprises a guide ribonucleic acid (RNA) barcode.

In some embodiments, the biological analyte is a ribonucleic acid (RNA) molecule, and wherein the target-specific sequence is complementary to the RNA molecule. In some cases, the target-specific sequence is a poly-T sequence. In some embodiments, the biological analyte is a deoxyribonucleic acid (DNA) molecule, and wherein the target-specific sequence is complementary to the DNA molecule.

In some embodiments, (b) is performed in bulk. In some embodiments, (b) is performed in a partition of a plurality of partitions. In some cases, the partition is a droplet.

In some cases, the partition is a well.

In some embodiments, further comprising, subsequent to (b), bringing the functionalized barcode molecule in contact with the biological analyte. In some embodiments, (b) is performed in a reaction vessel having the biological analyte.

In some embodiments, the barcode molecule is attached to the bead through one or more linkers. In some cases, the one or more linkers comprise nucleic acid molecules. In some embodiments, in (a), the bead comprises a plurality of barcode molecules, which plurality of barcode molecules comprises the barcode molecule.

In some embodiments, the non-target-specific sequence comprises between 5 and 30 nucleotides or nucleotide analogues.

In some embodiments, the conditions permit hybridization of the non-target-specific sequence to the sequence complementary to the non-target-specific sequence Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 9 discloses SEQ ID NOS 165 and 165, respectively, in order of appearance.

DETAILED DESCRIPTION

Figure 1:
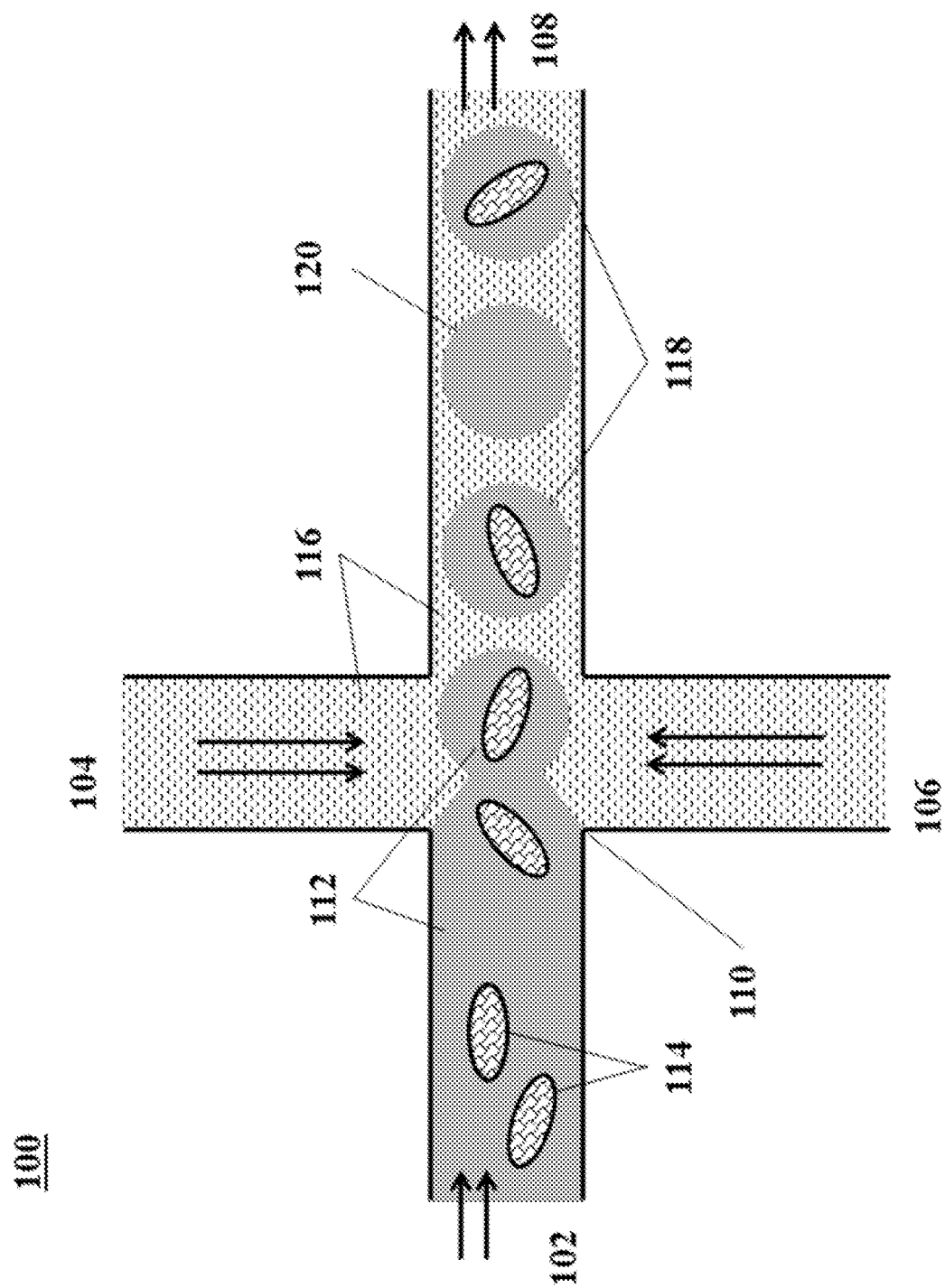
FIG. 1 shows an example of a microfluidic channel structure for partitioning individual biological particles.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

The term "barcode," as used herein, generally refers to a label, or identifier, that conveys or is capable of conveying information about an analyte. A barcode can be part of an analyte. A barcode can be independent of an analyte. A barcode can be a tag attached to an analyte (e.g., nucleic acid molecule) or a combination of the tag in addition to an endogenous characteristic of the analyte (e.g., size of the analyte or end sequence(s)). A barcode may be unique. Barcodes can have a variety of different formats. For example, barcodes can include: polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads.

The term "real time," as used herein, can refer to a response time of less than about 1 second, a tenth of a second, a hundredth of a second, a millisecond, or less. The response time may be greater than 1 second. In some instances, real time can refer to simultaneous or substantially simultaneous processing, detection or identification.

The term "subject," as used herein, generally refers to an animal, such as a mammal (e.g., human) or avian (e.g., bird), or other organism, such as a plant. For example, the subject can be a vertebrate, a mammal, a rodent (e.g., a mouse), a primate, a simian or a human. Animals may include, but are not limited to, farm animals, sport animals, and pets. A subject can be a healthy or asymptomatic individual, an individual that has or is suspected of having a disease (e.g., cancer) or a pre-disposition to the disease, and/or an individual that is in need of therapy or suspected of needing therapy. A subject can be a patient. A subject can be a microorganism or microbe (e.g., bacteria, fungi, archaea, viruses).

The term "genome," as used herein, generally refers to genomic information from a subject, which may be, for example, at least a portion or an entirety of a subject's hereditary information. A genome can be encoded either in DNA or in RNA. A genome can comprise coding regions (e.g., that code for proteins) as well as non-coding regions. A genome can include the sequence of all chromosomes together in an organism. For example, the human genome ordinarily has a total of 46 chromosomes. The sequence of all of these together may constitute a human genome.

The terms "adaptor(s)", "adapter(s)" and "tag(s)" may be used synonymously. An adaptor or tag can be coupled to a polynucleotide sequence to be "tagged" by any approach, including ligation, hybridization, or other approaches.

The term "sequencing," as used herein, generally refers to methods and technologies for determining the sequence of nucleotide bases in one or more polynucleotides. The polynucleotides can be, for example, nucleic acid molecules such as deoxyribonucleic acid (DNA) or ribonucleic acid (RNA), including variants or derivatives thereof (e.g., single stranded DNA). Sequencing can be performed by various systems currently available, such as, without limitation, a sequencing system by Illumina®, Pacific Biosciences (PacBio®), Oxford Nanopore®, or Life Technologies (Ion Torrent®). Alternatively or in addition, sequencing may be performed using nucleic acid amplification, polymerase chain reaction (PCR) (e.g., digital PCR, quantitative PCR, or real time PCR), or isothermal amplification. Such systems may provide a plurality of raw genetic data corresponding to the genetic information of a subject (e.g., human), as generated by the systems from a sample provided by the subject. In some examples, such systems provide sequencing reads (also "reads" herein). A read may include a string of nucleic acid bases corresponding to a sequence of a nucleic acid molecule that has been sequenced. In some situations, systems and methods provided herein may be used with proteomic information.

The term "bead," as used herein, generally refers to a particle. The bead may be a solid or semi-solid particle. The bead may be a gel bead. The gel bead may include a polymer matrix (e.g., matrix formed by polymerization or cross-linking). The polymer matrix may include one or more polymers (e.g., polymers having different functional groups or repeat units). Polymers in the polymer matrix may be randomly arranged, such as in random copolymers, and/or have ordered structures, such as in block copolymers. Cross-linking can be via covalent, ionic, or inductive, interactions, or physical entanglement. The bead may be a macromolecule. The bead may be formed of nucleic acid molecules bound together. The bead may be formed via covalent or non-covalent assembly of molecules (e.g., macromolecules), such as monomers or polymers. Such polymers or monomers may be natural or synthetic. Such polymers or monomers may be or include, for example, nucleic acid molecules (e.g., DNA or RNA). The bead may be formed of a polymeric material. The bead may be magnetic or non-magnetic. The bead may be rigid. The bead may be flexible and/or compressible. The bead may be disruptable or dissolvable. The bead may be a solid particle (e.g., a metal-based particle including but not limited to iron oxide, gold or silver) covered with a coating comprising one or more polymers. Such coating may be disruptable or dissolvable.

The term "sample," as used herein, generally refers to a biological sample of a subject. The biological sample may comprise any number of macromolecules, for example, cellular macromolecules. The sample may be a cell sample. The sample may be a cell line or cell culture sample. The sample can include one or more cells. The sample can include one or more microbes. The biological sample may be a nucleic acid sample or protein sample. The biological sample may also be a carbohydrate sample or a lipid sample. The biological sample may be derived from another sample. The sample may be a tissue sample, such as a biopsy, core biopsy, needle aspirate, or fine needle aspirate. The sample may be a fluid sample, such as a blood sample, urine sample, or saliva sample. The sample may be a skin sample. The sample may be a cheek swab. The sample may be a plasma or serum sample. The sample may be a cell-free or cell free sample. A cell-free sample may include extracellular polynucleotides. Extracellular polynucleotides may be isolated from a bodily sample that may be selected from the group consisting of blood, plasma, serum, urine, saliva, mucosal excretions, sputum, stool and tears.

The term "biological particle," as used herein, generally refers to a discrete biological system derived from a biological sample. The biological particle may be a macromolecule. The biological particle may be a small molecule. The biological particle may be a virus. The biological particle may be a cell or derivative of a cell. The biological particle may be an organelle. The biological particle may be a rare cell from a population of cells. The biological particle may be any type of cell, including without limitation prokaryotic cells, eukaryotic cells, bacterial, fungal, plant, mammalian, or other animal cell type, mycoplasmas, normal tissue cells, tumor cells, or any other cell type, whether derived from single cell or multicellular organisms. The biological particle may be a constituent of a cell. The biological particle may be or may include DNA, RNA, organelles, proteins, or any combination thereof. The biological particle may be or may include a matrix (e.g., a gel or polymer matrix) comprising a cell or one or more constituents from a cell (e.g., cell bead), such as DNA, RNA, organelles, proteins, or any combination thereof, from the cell. The biological particle may be obtained from a tissue of a subject. The biological particle may be a hardened cell. Such hardened cell may or may not include a cell wall or cell membrane. The biological particle may include one or more constituents of a cell, but may not include other constituents of the cell. An example of such constituents is a nucleus or an organelle. A cell may be a live cell. The live cell may be capable of being cultured, for example, being cultured when enclosed in a gel or polymer matrix, or cultured when comprising a gel or polymer matrix.

The term "macromolecular constituent," as used herein, generally refers to a macromolecule contained within or from a biological particle. The macromolecular constituent may comprise a nucleic acid. In some cases, the biological particle may be a macromolecule. The macromolecular constituent may comprise DNA. The macromolecular constituent may comprise RNA. The RNA may be coding or non-coding. The RNA may be messenger RNA (mRNA), ribosomal RNA (rRNA) or transfer RNA (tRNA), for example. The RNA may be a transcript. The RNA may be small RNA that are less than 200 nucleic acid bases in length, or large RNA that are greater than 200 nucleic acid bases in length. Small RNAs may include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA) and small rDNA-derived RNA (srRNA). The RNA may be double-stranded RNA or single-stranded RNA. The RNA may be circular RNA. The macromolecular constituent may comprise a protein. The macromolecular constituent may comprise a peptide. The macromolecular constituent may comprise a polypeptide.

The term "molecular tag," as used herein, generally refers to a molecule capable of binding to a macromolecular constituent. The molecular tag may bind to the macromolecular constituent with high affinity. The molecular tag may bind to the macromolecular constituent with high specificity. The molecular tag may comprise a nucleotide sequence. The molecular tag may comprise a nucleic acid sequence. The nucleic acid sequence may be at least a portion or an entirety of the molecular tag. The molecular tag may be a nucleic acid molecule or may be part of a nucleic acid molecule. The molecular tag may be an oligonucleotide or a polypeptide. The molecular tag may comprise a DNA aptamer. The molecular tag may be or comprise a primer. The molecular tag may be, or comprise, a protein. The molecular tag may comprise a polypeptide. The molecular tag may be a barcode.

The term "partition," as used herein, generally, refers to a space or volume that may be suitable to contain one or more species or conduct one or more reactions. A partition may be a physical compartment, such as a droplet or well. The partition may isolate space or volume from another space or volume. The droplet may be a first phase (e.g., aqueous phase) in a second phase (e.g., oil) immiscible with the first phase. The droplet may be a first phase in a second phase that does not phase separate from the first phase, such as, for example, a capsule or liposome in an aqueous phase. A partition may comprise one or more other (inner) partitions. In some cases, a partition may be a virtual compartment that can be defined and identified by an index (e.g., indexed libraries) across multiple and/or remote physical compartments. For example, a physical compartment may comprise a plurality of virtual compartments.

The terms "a," "an," and "the," as used herein, generally refers to singular and plural references unless the context clearly dictates otherwise.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

Provided herein are methods that may be used for various sample processing and/or analysis applications. A method of the present disclosure may provide a support (e.g., a bead, such as a gel bead) attached thereto a barcode molecule. The support may have attached thereto two or more different barcode molecules (e.g., nucleic acid barcode molecules) each comprising one or more sequences (e.g., priming sequences, barcode sequences, random N-mer sequences, capture sequences, poly(T) sequences, and/or other sequences). Two or more different barcode molecules attached to a support may comprise the same or different features. For example, a first barcode molecule attached to a support may comprise a first feature (e.g., a first sequence, such as a first nucleic acid sequence) and a second barcode molecule attached to the same support may comprise a second feature (e.g., a second sequence, such as a second nucleic acid sequence) that is the same as or different from said first feature. In some cases, a first barcode molecule attached to a support may comprise a first feature and a second feature and a second barcode molecule attached to the same support may comprise a third feature and a fourth feature, where the first and third features may be different from the second and fourth features. For example, different nucleic acid barcode molecules attached to the same bead may comprise the same barcode sequence and one or more different other sequences (e.g., functional or starter sequences). A barcode molecule may be releasably attached to a support (e.g., a bead). Methods of generating a plurality of barcode molecules coupled to a plurality of supports may comprise combinatorial (e.g., split pool) assembly and/or a series of hybridization and ligation processes. The methods may facilitate combinatorial construction of a bead library comprising beads comprising a plurality of different barcode molecules.

Barcode Molecules

In an aspect, the present disclosure provides a method for generating a plurality of barcode molecules (e.g., nucleic acid barcode molecules) from a plurality of molecules (e.g., nucleic acid molecules, such as a nucleic acid molecule comprising a starter or functional flow cell sequence) coupled to a plurality of supports (e.g., beads). The method may comprise combinatorially assembling (e.g., using a split pool method) the plurality of barcode molecules by coupling one or more molecules to each of the plurality of molecules. Each of the molecules coupled to a molecule coupled to a support may comprise one or more features, such as one or more nucleic acid sequences (e.g., barcode sequences, functional sequences, starter sequences, and/or overhang sequences, or complements thereof). A feature may comprise a barcode sequence or a portion of a barcode sequence. The plurality of molecules generated through this method may comprise (i) a first set of barcode molecules coupled to a support of a plurality of supports and (ii) a second set of barcode molecules coupled to the same support, where barcode molecules of the first set of barcode molecules are different than barcode molecules of the second set of barcode molecules. Barcode molecules of the first set of barcode molecules and barcode molecules of the second set of barcode molecules may comprise the same barcode sequence. The barcode molecules of the first set of barcode molecules and the barcode molecules of the second set of barcode molecules may comprise a barcode sequence that is different from other barcode sequences of other barcode molecules coupled to other supports of the plurality of supports. Accordingly, the method may provide a combinatorially constructed library of beads where each bead comprises two or more different barcode molecules, where each barcode molecule attached to a given bead comprises the same barcode sequence.

In some cases, methods of the present disclosure may be used to generate nucleic acid barcode molecules. In some cases, methods of the present disclosure may be used to generate barcode molecules that may be useful in a plurality of assays. A support may have multiple barcode molecule populations coupled thereto, each population of which may be configured for use in a different assay.

The methods described herein may comprise multiple ligation and/or hybridization processes. For example, a method may comprise providing a bead (e.g., a gel bead) that may have a starter sequence coupled thereto; providing a first molecule comprising a first sequence; attaching the first sequence of the first molecule to the starter sequence, thereby generating a first product; providing a second molecule comprising a second sequence; and attaching the second sequence of the second molecule to the first product, thereby generating a second product. The second molecule may comprise a barcode molecule, and may comprise one or more barcode sequences, functional sequences, overhang sequences and/or other sequences. In some cases, the second sequence comprises an overhang sequences. In some cases, the method may further comprise providing a third molecule comprising a third sequence and attaching the third sequence of the third molecule to the second product, thereby generating a third product. In some cases, the third product is a functionalized bead, wherein the third sequence comprises a functional sequence. In some cases, the third molecule comprises an assay primer. In other cases, the third product may comprise a barcode molecule, and may comprise one or more barcode sequences, functional sequences, overhang sequences and/or other sequences.

A support used in a method of the present disclosure may be, for example, a well, matrix, rod, container, or bead(s). A support may have any useful features and characteristics, such as any useful size, fluidity, solidity, density, porosity, and composition. In some cases, a support may be a bead such as a gel bead. A bead may be solid or semi-solid. Additional details of beads are provided elsewhere herein.

A support (e.g., a bead) may comprise a starter sequence functionalized thereto (e.g., as described herein). A starter sequence may be attached to the support via, for example, a disulfide linkage. A starter sequence may comprise a partial read sequence and/or flow cell functional sequence. Such a sequence may permit sequencing of nucleic acid molecules attached to the sequence by a sequencer (e.g., an Illumina sequencer). Different starter sequences may be useful for different sequencing applications. A starter sequence may comprise, for example, a TruSeq or Nextera sequence. A starter sequence may have any useful characteristics such as any useful length and nucleotide composition. For example, a starter sequence may comprise 2, 3, 4, 5, 6, 7, 8, 9, 10, 11, 12, 13, 14, 15, 16, 17, 18, 19, 20, or more nucleotides. In some cases, a starter sequence may comprise 15 nucleotides. Nucleotides of a starter sequence may be naturally occurring or non-naturally occurring (e.g., as described herein). A bead may comprise a plurality of starter sequences attached thereto. For example, a bead may comprise a plurality of first starter sequences attached thereto. In some cases, a bead may comprise two or more different starter sequences attached thereto. For example, a bead may comprise both a plurality of first starter sequences (e.g., Nextera sequences) and a plurality of second starter sequences (e.g., TruSeq sequences) attached thereto. For a bead comprising two or more different starter sequences attached thereto, the sequence of each different starter sequence may be distinguishable from the sequence of each other starter sequence at an end distal to the bead. For example, the different starter sequences may comprise one or more nucleotide differences in the 2, 3, 4, 5, 6, 7, 8, 9, 10, or more nucleotides furthest from the bead.

A first molecule (e.g., a first nucleic acid molecule or segment) may be attached to the starter sequence attached to the support (e.g., bead, such as a gel bead). Attachment of the first molecule may comprise hybridization and/or ligation (e.g., as described herein). A first molecule (e.g., a first nucleic acid molecule) may be provided that is capable of attaching to a starter sequence attached to a bead. A first molecule may be, for example, a nucleic acid molecule. In some cases, the first molecule may comprise an amino acid, peptide, polyethylene glycol (PEG) moiety, hydrocarbon chain, or another moiety. A first nucleic acid molecule may comprise a double-stranded region, one or more single-stranded regions, or both. For example, a first nucleic acid molecule may comprise a central portion that is a double-stranded region and adjacent regions on either side of the double-stranded region that are single-stranded regions. Such a nucleic acid molecule may be referred to as a "splint oligonucleotide". Both single-stranded regions of the first nucleic acid molecule may be on the same strand. The single-stranded region on a first end of a first nucleic acid molecule may comprise 1, 2, 3, 4, 5, 6, or more nucleotides. This single-stranded region may be referred to as an "overhang" sequence. The single-stranded region on a second end of a first nucleic acid molecule may comprise a sequence that is complementary to a starter sequence attached to the bead. For example, the bead may comprise a starter sequence comprising a TruSeq sequence, and a first nucleic acid molecule may comprise a single-stranded region comprising a sequence that is complementary to a distal portion of the TruSeq sequence. The complementary sequence may comprise any useful length and base composition. Similarly, the double-stranded region may comprise any useful length and composition. A strand of the double-stranded region of the first nucleic acid molecule may comprise a barcode sequence, and the corresponding strand may comprise a complement of the barcode sequence. As an example, the first nucleic acid molecule may comprise a first strand including a first barcode sequence and a second strand including a sequence complementary to a starter sequence or a portion thereof that is attached to a bead, a sequence complementary to the first barcode sequence of the first strand, and an overhang sequence.

A second molecule (e.g., a second nucleic acid molecule or segment) may be provided that is capable of attaching to the overhang sequence of a first molecule attached to a starter sequence attached to a support (e.g., bead). A second molecule may be, for example, a nucleic acid molecule and/or may comprise an amino acid, peptide, PEG moiety, hydrocarbon chain, or another moiety. A second nucleic acid molecule may comprise a double-stranded region and one or more single-stranded regions. For example, a second nucleic acid molecule may comprise a central portion that is a double-stranded region and adjacent regions on either side that are single-stranded regions. The single-stranded regions of the second nucleic acid molecule may be on the same or different strands. In some cases, a first strand of a second nucleic acid molecule comprises a single-stranded region comprising 1, 2, 3, 4, 5, 6, or more nucleotides. This single-stranded region may be referred to as a "complementary overhang" sequence. This sequence may be complementary to the overhang sequence of a first nucleic acid molecule. The first strand may comprise a second single-stranded region at a second end that comprises one or more additional sequences such as a unique molecular identifier or a functional sequence. The single-stranded region of a second end of the first strand of the second nucleic acid molecule may comprise 1, 2, 3, 4, 5, 6, 7, 8, 9, 10, 12, 14, 16, 18, 20, 25, 30, 35, 40, 45, 50, or more nucleotides. The first strand may further comprise a second barcode sequence in the double stranded region of the second nucleic acid molecule. The second strand may comprise a sequence complementary to the second barcode sequence. Accordingly, in some cases, a second nucleic acid molecule comprises a first strand comprising a complementary overhang sequence, a second barcode sequence, and one or more additional sequences such as a unique molecular identifier or a functional sequence and a second strand comprising a sequence that is complementary to the second barcode sequence. In other cases, the first strand may include a single-stranded region and the second strand may include a single-stranded region. The single-stranded region of a first strand of a second nucleic acid molecule may comprise a "complementary overhang" sequence that is complementary to the overhang sequence of a first nucleic acid molecule. The single-stranded region of the second strand of the second nucleic acid molecule may comprise 1, 2, 3, 4, 5, 6, or more nucleotides. This single-stranded region may be referred to as a "second overhang" sequence. The double-stranded region may comprise any useful length and composition. A strand of the double-stranded region of the second nucleic acid molecule may comprise a second barcode sequence, and the corresponding strand may comprise a complement of the second barcode sequence. As an example, the second nucleic acid molecule may comprise a first strand including a second barcode sequence and a complementary overhang sequence and a second strand including a sequence complementary to the second barcode sequence of the first strand, and a second overhang sequence. The second overhang 2, 3, 4, 5, 6, 7, 8, 9, 10, 11, 12, 13, 14, 15, 16, 17, 18, 19, 20, or more nucleotides. Nucleotides of the second overhang may be identical. Nucleotides of the second overhang may be different. In some cases, the second overhang is a 5' overhang. In other cases the second overhang is a 3' overhang.

A second nucleic acid molecule may be ligated to the first nucleic acid molecule (e.g., as described herein). Following ligation of the second nucleic acid molecule to the first nucleic acid molecule, the bead comprises a double-stranded nucleic acid barcode molecule attached thereto. In some cases, the second nucleic acid molecule comprises a second overhang sequence. This double-stranded nucleic acid barcode molecule with an overhang sequence may also be referred to as a "nucleic acid barcode molecule".

Figure 9:
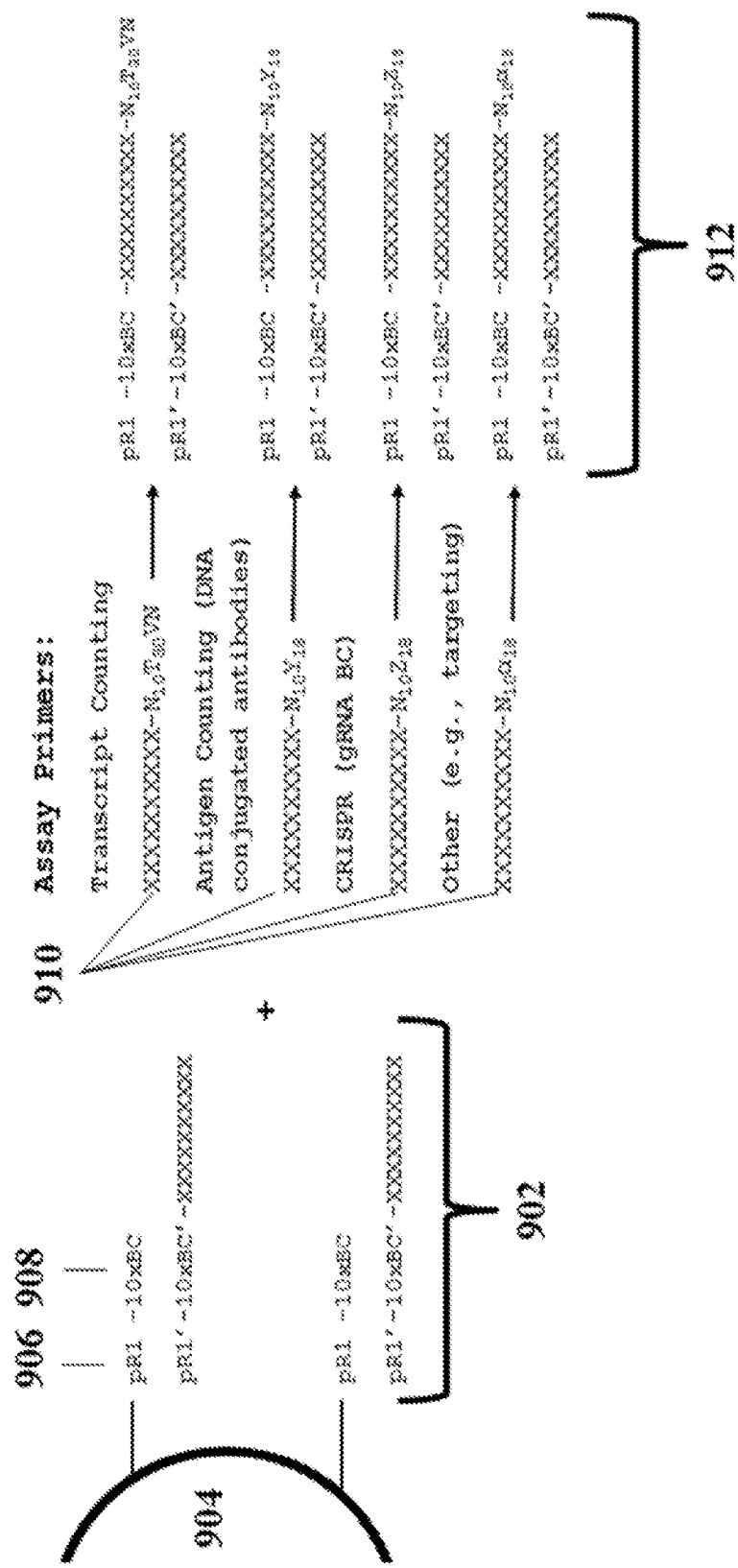
FIG. 9 shows an exemplary functionalized barcoded molecule comprising a bead coupled to a barcode molecule that can bind to assay primers for biochemical analyses.

FIG. 9 illustrates an exemplary nucleic acid barcode molecule 902 comprising an overhang bound to a bead 904. The nucleic acid barcode molecule 902 comprises a first nucleic acid molecule 906 (indicated as pR1) bound to the bead 904. The first nucleic acid molecule is attached to a second nucleic acid molecule 908. In this embodiment, the second nucleic acid molecule comprises a barcode (indicated as 10×BC) and a 5' overhang (indicated as XXXXXXXXXX, wherein X is a variable nucleotide).

Multiple barcode molecules (e.g., nucleic acid barcode molecules) may be generated on the same support (e.g., bead). For example, a bead may comprise a plurality of starter sequences attached thereto, and barcode molecules may be generated using all or a portion of the plurality of starter sequences. The barcode molecules attached to a given support may be the same (e.g., comprising the same barcode sequences, overhang sequences and/or other sequences). In some cases, barcode molecules attached to the same support may differ in unique molecular identifiers included in each barcode molecule. Such barcode molecules may otherwise include the same components. In some cases, the barcode molecule is a double-stranded nucleic acid molecule. In some cases, the barcode molecule is a single-stranded nucleic acid molecule. In some cases, the barcode molecule comprises a first functional group configured to couple to, and/or form a chemical bond with, a second functional group.

In some cases, multiple different barcode molecules (e.g., nucleic acid barcode molecules) may be generated on the same support (e.g., bead). For example, two different barcode molecules may be generated on the same support. Alternatively, three or more different barcode molecules may be generated on the same support. Different barcode molecules attached to the same support may comprise one or more different sequences. For example, different barcode molecules may comprise one or more different barcode sequences, and/or other sequences (e.g., starter sequences). In some cases, different barcode molecules attached to the same support may comprise the same barcode sequences. Different barcode molecules attached to the same support may comprise barcode sequences that are the same or different. Similarly, different barcode molecules may comprise unique molecular identifiers (UMIs) that are the same or different.

A nucleic acid molecule and/or a starter sequence associated with a support (e.g., bead) may comprise natural and/or non-naturally occurring (e.g., modified) nucleotides. For example, a nucleotide of a nucleic acid molecule and/or starter sequence associated with a bead may comprise any number or concentration of guanine, cytosine, thymine, uracil, and adenine bases, as well as non-naturally occurring (e.g., modified) nucleosides. A modified nucleoside may comprise one or more modifications (e.g., alkylation, hydroxylation, oxidation, or other modification) in its nucleobase and/or sugar moieties. A nucleic acid molecule and/or a starter sequence associated with a bead may comprise a nucleotide comprising a modified phosphate linker moiety. A nucleotide of a nucleic acid molecule and/or starter sequence may comprise one or more detectable moieties such as one or more fluorophores.

A barcode sequence of a barcode molecule (e.g., a nucleic acid barcode molecule) may comprise a first barcode sequence, a second barcode sequence, and, in some cases, a third barcode sequence. A first overhang sequence or a complement thereof and, in some cases, a second overhang sequence or a complement thereof, may be inserted between two or more sequences of a barcode sequence. For example, a barcode sequence may comprise a first barcode sequence and a second barcode sequence flanking an overhang sequence or complement thereof. In some cases, a barcode sequence may comprise, in order, a first barcode sequence, a first overhang sequence or complement thereof, a second barcode sequence, a second overhang sequence or complement thereof, and a third barcode sequence. A barcode sequence may have any useful length and composition. In some cases, a barcode sequence may comprise 4 or more nucleotides, such as 5, 6, 7, 8, 9, 10, 11, 12, 13, 14, 15, 16, 17, 18, 19, 20, 21, 22, 23, 24, 25, 26, 27, 28, 29, 30, or more nucleotides. For example, a barcode sequence may comprise a first barcode sequence comprising 6 nucleotides and a second barcode sequence comprising 8 nucleotides for a total of 14 nucleotides. In another example, a barcode sequence may comprise a first barcode sequence comprising 6 nucleotides, a second barcode sequence comprising 6 nucleotides, and a third barcode sequence comprising 8 nucleotides for a total of 20 nucleotides. A barcode sequence may comprise naturally occurring and/or non-naturally occurring nucleotides. A barcode sequence may comprise any useful sequence and composition of nucleotides. In some cases, all nucleic acid barcode molecules attached to a given bead comprise the same barcode sequences. In other cases, nucleic acid barcode molecules attached to a given bead may comprise different barcode sequences. For example, all nucleic acid barcode molecules may comprise the same first and second barcode sequences and different third barcode sequences. For beads for which all nucleic acid barcode molecules comprise the same barcode sequence, each nucleic acid barcode molecule may comprise a different unique molecular identifier that identifies the nucleic acid barcode molecules attached to the beads.

Overhang sequences may help control the generation of different nucleic acid barcode molecules on a given bead (e.g., as described herein) and/or may help binding to a primer assay as described herein. A given overhang sequence may comprise 2, 3, 4, 5, 6, or more nucleotides. In some cases, the overhang sequence comprises 2 nucleotides. Examples of overhang sequences comprising 2 nucleotides include GT (referred to herein as "alpha"), CA ("beta"), AG ("gamma"), TC ("delta"), GA ("epsilon"), CT ("zeta"), AC ("eta"), and TG ("theta").

Assay Primers

Successive attachment of a first molecule and a second molecule to a bead or a sequence attached thereto may result in the generation of a bead comprising a barcode molecule (e.g., a nucleic acid barcode molecule). The barcode molecule may be useful in various analysis and processing applications. Barcode molecules attached to beads may be useful for capturing and/or labeling, for example, nucleic acid sequences. In some cases, a third molecule (e.g., a third nucleic acid molecule or segment) may be provided that is capable of attaching to the second overhang sequence of a second molecule attached to a first molecule attached to a starter sequence attached to a support (e.g., bead) to generate a functionalized support, such as a functionalized bead. The third molecule may be, for example, a nucleic acid molecule and/or may comprise an amino acid, peptide, PEG moiety, hydrocarbon chain, or another moiety. In some cases, the third molecule is an assay primer.

A barcode molecule (e.g., a nucleic acid barcode molecule) may be combined with one or more assay primers comprising functional sequences designed to interact with a particular nucleic acid sequence or type of sequence. For example, an assay primer may comprise a functional sequence selected from the group consisting of capture sequences (e.g., random N-mers), poly(T) sequences, poly (C)sequences, primer sequences, universal primer sequences, primer annealing sequences, or other sequences. The assay primer may comprise one or more barcode sequences and/or unique molecular identifiers and be useful for indexing nucleic acid sequences deriving from one or a variety of sources. If a plurality of beads each comprising one or more barcode molecules comprising a unique barcode and/or unique molecular identifier is partitioned amongst a plurality of partitions (e.g., droplets or wells, as described herein) each comprising an analyte, the barcode molecules alone or bound to assay primers may be useful for indexing the analytes corresponding to each partition.

An assay primer may comprise a priming region and a sequence that is capable of binding or ligating to the second nucleic acid molecule for a barcode molecule. In some cases, the assay primer may comprise a sequence that can be ligated to a second nucleic acid molecule. In some cases, the assay primer can be ligated to a second nucleic acid molecule. In some instances, the assay primer comprises a first functional group and the second nucleic acid molecule comprises a second functional group, wherein the first and the second functional group can form a chemical bond, ligating the assay primer to the second nucleic acid molecule. In some cases, the 5' overhang of a second nucleic acid molecule comprises a non-target-specific sequence. In some cases, the 5' overhang of a second nucleic acid molecule comprises a target-specific sequence. Assay primers may comprise a sequence complementary to the splint oligo second sequence and an assay-specific sequence that determines assay primer functionality (e.g., a poly-T primer, a random N-mer primer, a target-specific primer, or a labelling agent capture sequence as described herein).

The priming region of an assay primer may comprise functional sequences that may be useful for different applications and assays. For example, a functional sequence capable of hybridizing with an mRNA molecule (e.g., a functional sequence comprising a poly(T) sequence) may facilitate analysis of an mRNA analyte, while a functional sequence capable of hybridizing with a DNA molecule (e.g., a capture sequence, such as a capture sequence comprising a random N-mer) may facilitate analysis of a DNA analyte.

In some cases, two or more applications or assays may occur at the same time. For example, a bead comprising at least two nucleic acid barcode molecules with a 5' overhang that is complementary to a sequence of an assay primer can bind to an assay primer comprising a poly(T) sequence and a different assay primer comprising a DNA capture sequence such that the same bead can be used to analyze an mRNA analyte and a DNA analyte in tandem (e.g., in a multi-assay method). In some cases, the barcode molecules are double-stranded nucleic acid molecules. In some cases, the barcode molecules are single-stranded nucleic acid molecules. In some cases, two or more applications or assays may occur at the same time. For example, a bead comprising at least two nucleic acid barcode molecules configured to chemically ligate to an assay primer can bind to an assay primer comprising a poly(T) sequence and a different assay primer comprising a DNA capture sequence such that the same bead can be used to analyze an mRNA analyte and a DNA analyte in tandem (e.g., in a multi-assay method). Other examples of functional sequences include functional sequences capable of interacting with other nucleic acid molecules (e.g., transfer RNA (tRNA) molecules, ribosomal RNA (rRNA) molecules, and mitochondrial RNA (mtRNA) molecules), functional sequences capable of interacting with an oligonucleotide coupled to a labeling agent (e.g., an oligonucleotide coupled to a protein or antibody or a lipid molecule) and capable of detecting a an analyte (e.g., an intracellular protein, extracellular protein, transmembrane protein, or surface protein), and functional sequences capable of interacting with a nucleic acid sequence of or encoding a perturbation agent such as a clustered regularly interspersed short palindromic repeat (CRISPR) agent (e.g., crRNA or sgRNA), transcription-activator like effector nucleases (TALENs, e.g., TALEN mRNA sequence)), zinc finger nucleases (ZFN, e.g., ZFN mRNA sequence), or other perturbation agent. A functional sequence may comprise a random N-mer. In some cases, a functional sequence may be referred to as a "target sequence." Examples of functional sequences that can be useful in assay primers of the claimed methods are provided in Table 1 below:

TABLE 1

Sequences for inclusion in assay primers

| Sequence Number | Sequence |
|---|---|
| 1 | TGCCTTGTAACGCGAA |
| 2 | TATGGCCGCGCAATTA |
| 3 | TTCGAGCGCGCAATTA |
| 4 | ATTGCGCCGAACGTAT |
| 5 | GTTGCACGCGCAATTA |
| 6 | TGCCATTGCGCGATAA |
| 7 | AAGGATCGCGCCTATT |
| 8 | GTTACGCGCGCAATTA |
| 9 | AGCATGTCGCGCATTA |
| 10 | TTCGCAACGGTCGAAT |
| 11 | ATTGCGCGCGAATTAC |

TABLE 1-continued

Sequences for inclusion in assay primers

| Sequence Number | Sequence |
|---|---|
| 12 | TCTTAGCGGACGCAAT |
| 13 | ATCCATGGCGCGATTA |
| 14 | GTTCGCACGCGAATTA |
| 15 | CGATTGCGCGACATTA |
| 16 | TGATCGCGCTACGAAT |
| 17 | CGCATTCAATTGGCGA |
| 18 | AACGTTCGCGATTGAC |
| 19 | GCTTGACCGCGAATTA |
| 20 | ACTGCGCGATTCGTAA |
| 21 | TCCAATAATGCGCGGT |
| 22 | AGTCATCGACCGGATT |
| 23 | AGACTTCGCGCGATTA |
| 24 | CTGAGTCGCGCAATTA |
| 25 | TCGCTAACGGTCGAAT |
| 26 | TATGCGCGCGAATTAC |
| 27 | TATGCGCGCTACGAAT |
| 28 | AACTGCGCGATTCGTA |
| 29 | TGGACCGCGCATATTA |
| 30 | TATCACAATGCGCGGT |
| 31 | GTCACGCGCGAATTAT |
| 32 | GTCTAGCGCGCAATTA |
| 33 | TCTGCAACGGTCGAAT |
| 34 | CCAGTGCGCGAATTAT |
| 35 | ATCGTCACGCGATTAG |
| 36 | GCCAATCGACGTTAGT |
| 37 | TTAGCGCGCGAATTAC |
| 38 | TCGATCAGTTACGCGA |
| 39 | ACCTGAATACGCGGTT |
| 40 | TGCGGTCGAACCTAAT |
| 41 | TGAACGCGCTACTATG |
| 42 | TGGCTTAATCGCGACA |
| 43 | TAGGTCCGCGACATTA |
| 44 | CCTTGGCGAACGATTA |
| 45 | AAGTCCGCGCGATTAT |
| 46 | GACTGTCGCGCAATTA |
| 47 | TTAGGTCCGCTACGAA |
| 48 | TCTGTGAACCGTCGAA |

TABLE 1-continued

Sequences for inclusion in assay primers

| Sequence Number | Sequence |
|---|---|
| 49 | GTCACAATACGCGGTT |
| 50 | GAGACTTCGCGCATTA |
| 51 | GAGCAATTCGCGCTAT |
| 52 | CGTTACGATTACGCGA |
| 53 | AGCACGTAATCGTTCG |
| 54 | GCGTTACCGAACGTAT |
| 55 | TTAACGACCGGTTACG |
| 56 | ATTGCGCGCGATACTA |
| 57 | CTGTTGACCGCGAATA |
| 58 | GCAAGATTCGCGCTAT |
| 59 | GGCCATCGCGAATTAT |
| 60 | ATGGACCGCGCTATTA |
| 61 | ACGCGATAATCGTTCG |
| 62 | TAGGCATTATCCGCGA |
| 63 | TCAGCTCGAACGGTTA |
| 64 | CATTCAATTGCGCGAG |
| 65 | GCTCAATTACGCGGAT |
| 66 | ACGGATCGCATCGTTA |
| 67 | CTGCAATTACGCGGAT |
| 68 | TGTCGATTACGCGAAC |
| 69 | ACCTAGGCGCGATTAT |
| 70 | CGCGTAGCGCATATTA |
| 71 | CAATCGTTACGCGGAT |
| 72 | TAACGCTTACGCGGAT |
| 73 | GCTAACGCGATTCGTA |
| 74 | ATTCCTAATGCGCGAG |
| 75 | TTCACTAATGCGCGAG |
| 76 | CAAGGATTCGCGCTAT |
| 77 | ACGATTCGACCGGTAT |
| 78 | GAGCAACTATTCGCGT |
| 79 | TACCTACGATTGCGAG |
| 80 | TAATCGACCGGTTACG |
| 81 | GTTCACAATACGCGGT |
| 82 | GCTAGCGCGCATATTA |
| 83 | ACTGACTTACGCGGAT |
| 84 | GCACGTTCGCGTAATA |
| 85 | AAGGTCCGCGCTATTA |
| 86 | CTAGTGAACGCGCTAT |

TABLE 1-continued

Sequences for inclusion in assay primers

| Sequence Number | Sequence |
|---|---|
| 87 | GGCCATCGATTCGTAA |
| 88 | ACCTTGCGCGATAGTA |
| 89 | CTAGGTCCGCGAATTA |
| 90 | ATATCGACCGGTTACG |
| 91 | ATAGCTTATGCGCGAC |
| 92 | ACGTTAATCGGTACGC |
| 93 | CATCATCGATTGCGAG |
| 94 | GTAACTCGACCGGATT |
| 95 | TCGAACGCGTATTAGC |
| 96 | TAGTCGACCGATTACG |
| 97 | GATCACGCGATTCGTA |
| 98 | AGTTAGCGTTACGACC |
| 99 | GCTCAATAAGTCGCGT |
| 100 | CTTAGGCGCGAATTAC |
| 101 | TAGGTCACGTTACGAC |
| 102 | ATACCTTATGCGCGAG |
| 103 | GCACGATAGTTCGCTA |
| 104 | GTCATACAATTCGCGG |
| 105 | CGACTATTATGCGCGA |
| 106 | TAAGCCGCGTATTAGC |
| 107 | CGAATTCGACCGGTAT |
| 108 | CGTCAATAATCGCGTG |
| 109 | GGAACCTTAATCGCGT |
| 110 | GCTCAATAATCGCGTG |
| 111 | CCAATGCGCGTTAGTA |
| 112 | GAACTTCGACCGGTAT |
| 113 | CGCTTAATCGAACGGT |
| 114 | CCTTGAGTCGAACGAT |
| 115 | ATCGAGTAACCGTTCG |
| 116 | TACCGTAACGTAGTCG |
| 117 | GTTCTCATCGAACGGA |
| 118 | ATCTTGAATCGCGACG |
| 119 | AGACCTTAATCGCGTG |
| 120 | GACCAATATGTCGCGT |
| 121 | CGTAATCGACCGGTAT |

TABLE 1-continued

Sequences for inclusion in assay primers

| Sequence Number | Sequence |
|---|---|
| 122 | GTACACTAAGTCGCGT |
| 123 | TAGTACCGATTGACCG |
| 124 | AGTCTAATCGGTACGC |
| 125 | GTACTGACCGATTACG |
| 126 | CCTTGAATCGAACGGT |
| 127 | TCGACTAATCGGTACG |
| 128 | GCGGATTACGCTACTA |
| 129 | CCTTAGTAGTACGCGA |
| 130 | CCTTAAGTTACGCGAG |
| 131 | GTAAGTACGCGCTATC |
| 132 | CTGTCGCGATCGATAA |
| 133 | GGACAATCGCTCGTTA |
| 134 | GTCCGTCGATCGATAA |
| 135 | GACTTACGACCGGTAT |
| 136 | CTGTTAATCGACCGGA |
| 137 | ATGCGGTAACCTATCG |
| 138 | AGATAGTTACGCGTCC |
| 139 | GAGTCCAACTATCGGT |
| 140 | TTACAGTACTAGCGGC |
| 141 | GACTAATACGCGTTCG |
| 142 | TGGTAACTATACCGGC |
| 143 | CGTACGTAACTATCGG |
| 144 | GACCTTAATCGGTACG |
| 145 | CATTACCGGATAGTCG |
| 146 | GATAGTTATCGCACCG |
| 147 | ACTAGTCGTACGATGC |
| 148 | GATCACTAATCGCGTG |
| 149 | GCGTTACGCTAATACG |
| 150 | CACGATCGTACGGTAT |
| 151 | TGTACGTACGATCCGA |
| 152 | CTAGACTAATCGCGTG |
| 153 | CATAGTCGTACGATGC |
| 154 | GTCGACTAACTATCGG |

Additional functional sequences that may be included in assay primers are included in Table 2 below:

TABLE 2

Sequences for inclusion in assay primers

| Sequence Number | Sequence |
|---|---|
| 155 | CCTTAGCCGCTAATAGGTGAGC |
| 156 | TTGCTAGGACCGGCCTTAAAGC |
| 157 | GAGGATTGCGCACCTTACTAGC |
| 158 | CAACTTTAGCGGTCCAAGGTGC |
| 159 | ACGCTAGTTTCGCGTACGAAGC |
| 160 | ACGCTAGTTTCGCGTACGAAGC |
| 161 | GAGGATTGCGCACCTTACTAGC |
| 162 | TTGCTAGGACCGGCCTTAAAGC |
| 163 | GACAATTGTCGGCTCGACTAGC |

In some cases, an assay primer may comprise a sequence selected from the sequences included in Tables 1 and 2. In some cases, an assay primer may comprise a complement or reverse complement of a sequence selected from the sequences included in Tables 1 and 2. In some embodiments, a particular analyte of interest (e.g., nucleic acid, cell surface protein, CRISPR RNA or other perturbation agent) may comprise, may be coupled to, or otherwise associated with an oligonucleotide comprising a sequence that is at least partially complementary to a sequence on a barcode molecule (e.g., a sequence in Table 1 or 2).

FIG. 9 provides exemplary assay primers 910 for use with the barcode molecules described herein. For example, the top assay primer comprises a non-target-specific sequence (shown as XXXXXXXXXX) and a sequence indicated by $N_{10}$ and $T_{30}VN$ (SEQ ID NO: 164). The sequence $N_{10}$ represents a random N-mer that represents a unique molecular identifier while the sequence $T_{30}VN$ (SEQ ID NO: 164) represents a functional sequence. This assay primer may be used for transcript counting. Another exemplary assay primer (second from the top) comprises a non-target-specific sequence (shown as XXXXXXXXXX) and a sequence indicated by $N_{10}$ and $Y_{18}$. This assay primer may be used in combination with the nucleic barcode molecules for antigen counting. Another exemplary primer (third from the top) comprises a non-target-specific sequence (shown as XXXXXXXXXX) and a sequence indicated by $N_{10}$ and $Z_{18}$. This exemplary primer may be used to detect genomic edits following a gene-editing reaction. In some cases, the exemplary assay primer or functionalized molecule 910 can chemically ligate to the second molecule 908, to create a functionalized barcode molecule 912. The non-target-specific sequence (shown as XXXXXXXXXX) of the exemplary assay primers 910 can bind to the 5' overhang of the second molecule 908, to create functionalized beads 912. In some cases, the non-target-specific sequence (shown as XXXXXXXXXX) of 910 is complementary to a non-target-specific sequence (shown as XXXXXXXXXX) of the 5' overhang of the second molecule of 908.

Biochemical Analyses

Analyses may be conducted using the barcode molecules bound to beads and assay primers as described herein. In some cases, the assay primers may be added to the beads attached with the barcode molecules to form functionalized beads that can be used for analyses. In other cases, assay primers are added to the reaction mix with the barcode molecules at the same times. These beads may be divided amongst different partitions and used for analysis of different analytes. For example, a single bead of the collection of beads may be co-partitioned with a single biological particle (e.g., a cell) comprising an analyte and one or more reagents. A plurality of partitions may be similarly generated (e.g., as described herein) such that each partition includes a bead having attached thereto a differently functionalized barcode molecule.

In some cases, the methods described herein may be used to screen cells carrying mutations, e.g., mutations generated by gene editing such as CRISPR technology. For example, a bead comprising a first nucleic acid barcode molecule attached to an assay primer for CRISPR RNA (e.g., crRNA or guide RNA) or its complementary DNA and a second nucleic acid barcode with an assay primer for endogenous nucleic acid in the cell (e.g., total mRNA or a specific mRNA) may be made into a partition with a cell transfected with CRISPR RNA or a plasmid expressing CRISPR RNA. In some cases, the expressed CRISPR RNA or the plasmid may have a barcode (CRISPR barcode) or a capture sequence. The assay primers attached to the nucleic acid barcode molecules on the bead may be used to amplify and sequence the CRISPR RNA (e.g., using a nucleic acid barcode molecule comprising a sequence complementary to the CRISPR capture sequence, and endogenous mRNA (e.g., using a nucleic acid barcode molecule comprising an oligo (dT) sequence), thus determining the mutations generated by in the cell. In some cases, the methods may be used to perform single cell RNA sequencing, e.g., as described in Dixit, et al., Perturb-Seq: Dissecting Molecular Circuits with Scalable Single-Cell RNA Profiling of Pooled Genetic Screens. Cell; Dec. 15, 2016; 167(7):1853-1866.e17, which is incorporated herein by reference in its entirety.

In any of the methods described herein, a double-stranded nucleic acid barcode molecule attached to a bead may be denatured to provide a single-stranded nucleic acid barcode molecule attached to the bead. Denaturation may be achieved controlling, for example, temperature, pressure, and/or pH conditions and/or by employing a chemical or biological agent such as a detergent.

A support (e.g., a bead such as a gel bead) may comprise a plurality of oligonucleotides or barcode molecules (e.g., nucleic acid barcode molecules) attached thereto. The support may comprise at least 10,000 barcode molecules attached thereto. For example, the support may comprise at least 100,000, 1,000,000, or 10,000,000 barcode molecules attached thereto. In any of the methods described herein, one or more oligonucleotides or barcode molecules may be releasably attached to a support. A barcode molecule may be releasable from a support upon application of a stimulus. Such a stimulus may be selected from the group consisting of a thermal stimulus, a photo stimulus, and a chemical stimulus. For example, the stimulus may be a reducing agent such as dithiothreitol Application of a stimulus may result in one or more of (i) cleavage of a linkage between barcode molecules of the plurality of barcode molecules and the support, and (ii) degradation or dissolution of the support (e.g., bead) to release barcode molecules of the plurality of barcode molecules from the support. For a support comprising multiple different barcode molecules, different barcode molecules may be released from the bead upon application of different supports. For example, a first stimulus may be applied to release a first barcode molecule and may not release a second barcode molecule, and a second stimulus may be applied to release the second barcode molecule and may not release the first barcode molecule.

Different analytes capable of being analyzed by a support (e.g., a bead) comprising multiple different barcode molecules or a collection of such supports (e.g., beads) may be contained within or associated with a cell. A cell may be, for example, a human cell, an animal cell, or a plant cell. In some cases, the cell may be derived from a tissue or fluid, as described herein. The cell may be a prokaryotic cell or a eukaryotic cell. The cell may be a lymphocyte such as a B cell or T cell. Access to a plurality of molecules included in a cell may be provided by lysing or permeabilizing the cell. Lysing the cell may release an analyte contained therein from the cell. A cell may be lysed using a lysis agent such as a bioactive agent. A bioactive agent useful for lysing a cell may be, for example, an enzyme (e.g., as described herein). Alternatively, an ionic or non-ionic surfactant such as TritonX-100, Tween 20, sarcosyl, or sodium dodecyl sulfate may be used to lyse a cell. Cell lysis may also be achieved using a cellular disruption method such as an electroporation or a thermal, acoustic, or mechanical disruption method. Alternatively, a cell may be permeabilized to provide access to a plurality of nucleic acid molecules included therein. Permeabilization may involve partially or completely dissolving or disrupting a cell membrane or a portion thereof. Permeabilization may be achieved by, for example, contacting a cell membrane with an organic solvent or a detergent such as Triton X-100 or NP-40.

A biological particle (e.g., a cell) including an analyte may be partitioned with a bead comprising one or more nucleic acid barcode molecules within a partition such as a well or droplet, e.g., as described herein. One or more reagents may be co-partitioned with a cell and bead. For example, a cell may be co-partitioned with one or more reagents selected from the group consisting of lysis agents or buffers, permeabilizing agents, enzymes (e.g., enzymes capable of digesting one or more nucleic acid molecules, extending one or more nucleic acid molecules, reverse transcribing an RNA molecule, permeabilizing or lysing a cell, or carrying out other actions), fluorophores, oligonucleotides, primers, barcodes, nucleic acid barcode molecules (e.g., nucleic acid barcode molecules comprising one or more barcode sequences), buffers, deoxynucleotide triphosphates, detergents, reducing agents, chelating agents, oxidizing agents, nanoparticles, beads, and antibodies. In some cases, a cell and bead may be co-partitioned with one or more reagents selected from the group consisting of temperature-sensitive enzymes, pH-sensitive enzymes, light-sensitive enzymes, reverse transcriptases, proteases, ligase, polymerases, restriction enzymes, nucleases, protease inhibitors, exonucleases, and nuclease inhibitors. For example, a cell and a bead may be co-partitioned with a reverse transcriptase and nucleotide molecules. Partitioning a cell, a bead, and one or more reagents may comprise flowing a first phase comprising an aqueous fluid, the cell, the bead, and the one or more reagents and a second phase comprising a fluid that is immiscible with the aqueous fluid toward a junction. Upon interaction of the first and second phases, a discrete droplet of the first phase comprising the cell, bead, and the one or more reagents may be formed. In some cases, the partition may comprise a single cell and a single bead. The cell may be lysed or permeabilized within the partition (e.g., droplet) to provide access to the plurality of molecules of the cell. Accordingly, molecules originating from the same cell may be isolated and barcoded within the same partition with the same barcode.

The present disclosure also provides a method for processing a plurality of analytes using a plurality of supports comprising a plurality of barcode molecules (e.g., as described herein). The method may comprise providing a plurality of barcode molecules coupled to a plurality of supports (e.g., beads, such as gel beads, as described herein). The plurality of barcode molecules may comprise first and second barcode molecules coupled to the same support. The first and second barcode molecules may be different. The first and second barcode molecules may be identical. The support may be partitioned into a partition (e.g., a droplet or well), such that the partition comprises the support comprising the plurality of barcode molecules as well as a plurality of analytes. The plurality of analytes may comprise, for example, nucleic acid molecules (e.g., DNA and RNA molecules), amino acids, polypeptides, and/or proteins. The plurality of analytes may derive from the same source. For example, the plurality of analytes may be included in or derived from the same biological particle (e.g., cell). The biological particle may be lysed or permeabilized to provide access to the plurality of analytes. Subsequent to partitioning, a first barcode molecule of the first barcode molecules coupled to the support and functionalized with a first assay primer, and a first analyte (e.g., a DNA molecule) of the plurality of analytes may be used to generate a first barcoded analyte. A second barcode molecule of the second barcode molecules coupled to the support and functionalized with a second assay primer, and a second analyte (e.g., an RNA molecule) of the plurality of analytes may be used to generate a second barcoded analyte. The first and second barcoded analytes, or derivatives thereof, may be recovered from the partition. The first and second barcoded analytes, or derivatives thereof, may then be subjected to subsequent processing and analysis, such as nucleic acid sequencing. A derivative of a barcoded analyte may include one or more functional sequences in addition to those of the barcoded analyte, such as one or more sequencing adapters or primers or other functional sequences. In an example, the first and second barcoded analytes are generated and are subsequently functionalized with sequencing adapters suitable for performing a nucleic acid assay (e.g., nucleic acid sequencing). In another example, a derivative of a barcoded analyte may comprise a portion of the barcoded analyte. For example, a portion of the barcoded analyte may be separated from the barcoded analyte and, optionally, another molecular segment or functional sequence may be added to the barcoded analyte.

Barcode molecules (e.g., first barcode molecules or said second barcode molecules) coupled to a support (e.g., bead) may be configured to interact with various analytes by being coupled to an assay primer. For example, some or all barcode molecules coupled to a given support (e.g., bead) may be configured to interact with DNA molecules using an assay primer that binds DNA molecules. Alternatively or in addition, some or all barcode molecules coupled to a given support (e.g., bead) may be configured to interact with RNA molecules (e.g., mRNA molecules) using an assay primer that binds RNA molecules. In some cases, the assay primers may also be configured to interact with amino acids, polypeptides or proteins.

Ligation Methods

Described herein is an exemplary double ligation method involving a bead comprising a starter sequence comprising a TruSeq sequence. A first nucleic acid molecule comprising a first strand and a second strand is ligated to the TruSeq sequence. The second strand of the first nucleic acid molecule comprises a sequence complementary to a portion of the TruSeq sequence at one end and a two-nucleotide overhang sequence (CA) at a second end. The first strand comprises a first barcode sequence, and the second strand comprises a sequence complementary to the first barcode sequence. A second nucleic acid molecule comprising a first strand and a second strand is ligated to the first nucleic acid molecule. The first strand comprises a barcode sequence and the second strand comprises a sequence complementary to the second barcode sequence.

Alternatively, concentration and other reaction parameters may be used to control the nucleic acid barcode molecules formed in a so-called "concentration control" construction method. For example, two different nucleic acid barcode molecules may be attached to a bead, where each nucleic acid barcode molecule comprises the same starter sequence (e.g., a TruSeq sequence). The barcode sequence associated with each nucleic acid barcode molecule may be the same. In order to achieve multiple different nucleic acid barcode molecules attached to a bead, different concentrations of a second or third nucleic acid molecule may be added to a ligation reaction mixture. For example, for a double ligation reaction, equal concentrations of a first nucleic acid molecule and a second nucleic acid molecule may be added to the ligation reaction mixture, which may result in equal concentrations of the first and second nucleic acid molecules attached to a bead.

Multiple ligation reactions used in the preparation of barcode molecules (e.g., nucleic acid barcode molecules) according to the methods provided herein may be performed in a combinatorial fashion. Combinatorial (e.g., split pool) approaches permit the generation of a high diversity of barcode molecules (e.g., barcoded beads) using a reduced number of molecules (e.g., nucleic acid molecules). A combinatorial scheme involves assembling multiple molecular segments or sequences (e.g., a nucleic acid molecule or a portion thereof) to provide a larger molecule (e.g., a molecule comprising two or more molecular segments or sequences).

In some cases, a combinatorial ligation method such as that described herein may comprise immobilizing a plurality of beads to a plurality of supports (e.g., wells of a well plate). The first ligation step may involve providing a plurality of first molecules (e.g., first nucleic acid molecules) to each partition and promoting a ligation reaction. Rather than pooling the plurality of beads from each partition, excess material may be washed out of each partition and a plurality of second molecules (e.g., second nucleic acid molecules) washed into each partition for a second ligation reaction. Accordingly, the methods of the present disclosure may comprise moving beads between partitions or moving fluids between partitions.

Double ligation reactions may be carried out in a series of well plates. For example, ligation of first molecules (e.g., first nucleic acid molecules) may be performed within wells of a 96 well plates using, e.g., 96 different first molecules (e.g., as described herein). Each well may also include a plurality of beads and one or more reagents. The plurality of beads may comprise one or more different starter sequences attached thereto. The plate may then be subjected to appropriate reaction conditions (e.g., appropriate pressure, concentration, and temperature conditions with appropriate reagents) to promote ligation between first molecules and starter sequences of beads within each well. Subsequent to this first ligation reaction, the contents of each well may be pooled and mixed. The contents of the resultant pooled mixture may then be redistributed between a plurality of wells in a separate well plate. For example, beads in the pooled mixture may be partitioned among 96 wells of a second 96 well plate. Each well may include a different second molecule (e.g., as described herein) and one or more reagents. A second ligation reaction may be performed within each well to generate a plurality of beads comprising the same second molecule and a plurality of different first molecules within each well.

Combinatorial (e.g., split pool) ligation approaches such as those provided herein may generate significant diversity of barcode molecules. However, in some cases, unwanted off-products may also be generated. This may be due to ligation steps having less than 100% efficiency, such as between 95-97% efficiency. Off-products may not include the full length barcode sequence as the desired products and/or may lack a functional sequence. The overall efficiency of a combinatorial process may decrease for processes involving more ligation steps (e.g., triple ligation may be less efficient and generate more off-products than double ligation). Because off-products may interfere with biochemical reactions of interest, it may be beneficial to remove off-products (e.g., partial ligation products) without having other adverse effects on desired products. Removing the off-products may comprise degrading the off-products. Degrading these components may be accomplished by, for example, the use of one or more exonucleases. Exonucleases (e.g., ExoI) are typically inhibited by phosphorothioate bonds in the phosphate backbone of a nucleic acid. By incorporating a phosphorothioate bond between the final 3' base of a barcode molecule and the base immediately preceding it, a molecule can be created that is resistant to 3'→5' exonuclease activity. This bond can be incorporated onto the final oligo that is ligated during a split pool ligation process. In this case, only molecules that are full length (e.g., desired products) can be protected from the exonuclease and partial ligation products (e.g., off-target products) may be digested by the exonuclease. This process may provide a population of molecules that include nearly 100% of the desired molecules (e.g., full length). Such a process may be particularly useful in a triple ligation approach where the initial efficiency may otherwise be undesirably low. This process may be used on any pool of molecules constructed in a combinatorial process where the final component (e.g., molecular segment or sequence) added includes a 3' phosphorothioate bond. The process may be performed within partitions (e.g., droplets or wells) and/or with molecules (e.g., barcode molecules) coupled to beads (e.g., gel beads) or a solid surface. Alternatively, the process may be performed with molecules (e.g., barcode molecules) in solution. A variety of exonucleases may be used in the process, including exonucleases unable to degrade phosphorothioate bonds. Other 3' modifications can be used to achieve the same effect including, for example, spacer molecules, biotin, and fluorophores. Blockers at the 3' end of a complete barcode molecule may also be employed. Such modifications may inhibit the ability of the molecule (e.g., barcode molecule) to particulate in a given reaction, however. Accordingly, a modification may be removed or reversed subsequent to an exonuclease digestion process, e.g., using an enzymatic or chemical mechanism.

The use of exonucleases such as Exonuclease I (ExoI) to "clean-up" combinatorial processes performed on supports (e.g., gel beads) permits digestion of partially ligated molecules, leaving only fully ligated barcode molecules coupled to the supports. Notably, exonucleases such as ExoI may be stored in solutions comprising one or more materials capable of degrading supports (e.g., gel beads). For example, a solution for storing ExoI may include dithiothreitol (DTT), which may degrade gel beads. Accordingly, an exonuclease may be purified before it is used according to the methods provided herein.

A method of improving efficiency of a combinatorial assembly process may comprise performing one or more ligation processes (e.g., as described herein), performing an additional ligation process using a molecular segment or sequence comprising a phosphorothioate moiety, and subjecting the resulting ligation products to conditions sufficient to remove or degrade products that do not comprise the molecular segment or sequence comprising the phosphorothioate moiety. These conditions may comprise combining the ligation products with an exonuclease such as ExoI. The exonuclease may be included in a buffered solution, such as a solution comprising Tris-HCl, $MgCl_2$, NaCl, Triton X-100, glycerol, and/or ATP. The conditions may comprise incubation at, e.g., about 37 degrees Celsius (° C.) or higher for several minutes. In an example, the ligation products may be incubated with the exonuclease at about 37° C. for about 1 hour and may then be subjected to approximately 15 minutes of incubation at a higher temperature such as about 65° C.

The present disclosure also provides kits comprising a plurality of barcode molecules (e.g., nucleic acid barcode molecules). A kit may comprise a plurality of supports (e.g., beads, such as gel beads) and a plurality of barcode molecules coupled to the plurality of supports. First barcode molecules and second barcode molecules may comprise barcode sequences (e.g., as described herein). The barcode sequences of first barcode molecules and second barcode molecules attached to the same support may be identical. The barcode sequences of first barcode molecules and second barcode molecules attached to the same support may be different.

The plurality of supports may be a plurality of beads (e.g., as described herein), such that barcode molecules (e.g., first barcode molecules of the first set of barcode molecules and the second barcode molecules of the second set of barcode molecules) are coupled to a bead of the plurality of beads. At least a subset of the barcode molecules coupled to a bead may be coupled to an interior of the bead. Alternatively or in addition, barcode molecules may be coupled to a surface (e.g., an interior or exterior surface) of a bead. Barcode molecules may be releasably coupled to a bead, e.g., via chemical cross-linkers (e.g., as described herein). Beads may be gel beads. Beads may be dissolvable or disruptable (e.g., upon application of an appropriate stimulus).

Figure 10:
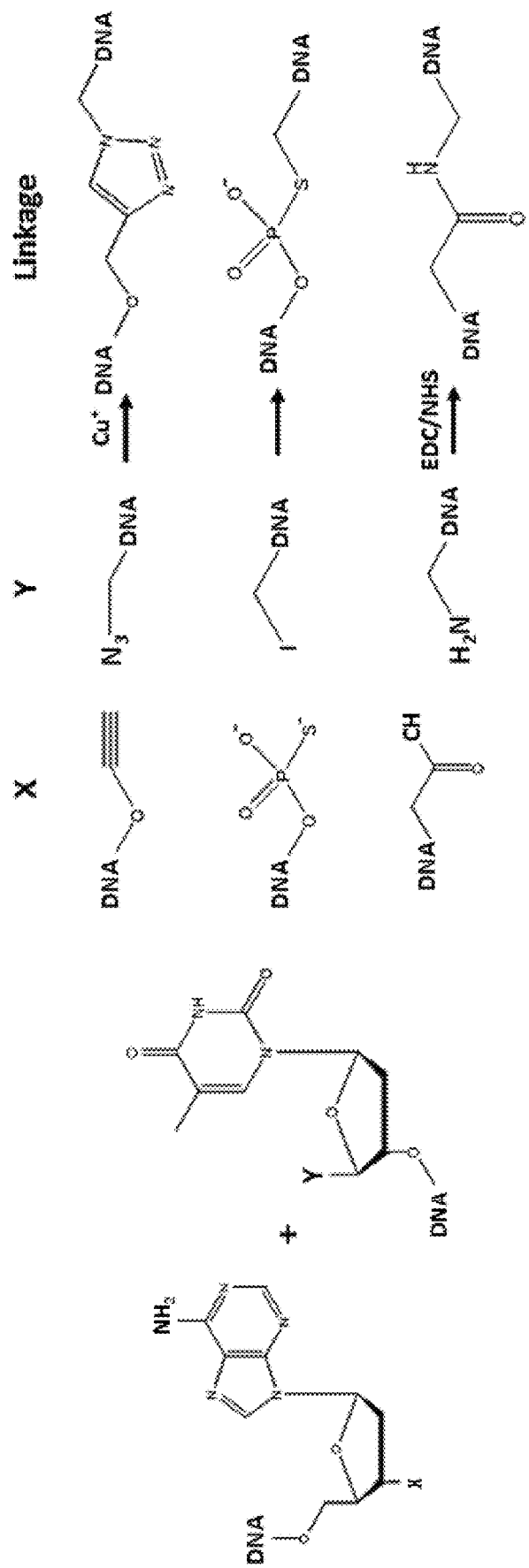
FIG. 10 shows exemplary chemical reactions for ligating an assay primer to a barcoded oligonucleotide bound to a bead.

Ligation between a nucleic barcode molecule (e.g. comprising a first nucleic acid molecule and a second nucleic acid molecule) and an assay primer or functionalizing molecule to form a functionalized nucleic acid barcode molecule coupled to a support such as bead may be through a number of enzymatic and/chemical reactions. FIG. 10 provides exemplary chemical reactions that may occur between two or more nucleic acid molecules. FIG. 10 further provides exemplary chemical reactions that can occur between a barcode molecule and a functionalizing molecule. In some cases, the barcode molecule is coupled to a bead. In some cases, the barcode molecule comprises a first functional or chemical group (e.g., X in FIG. 10) and the functionalizing molecule comprises a second functional or chemical group (e.g., Y in FIG. 10), and wherein said chemical ligation comprises formation of a chemical bond between said first and second functional group. For example, the chemical reaction may be a copper-mediated cycoaddition (click chemistry, as described herein). The ligation reaction can be between a iodide group (first functional group) and a phosphorothioate group (second functional group) to form a phosphorothioate bond. Additionally, the chemical ligation reaction may be between an acid group and an amine group to form an amide bond. In some cases, the second nucleic acid molecule of a nucleic acid barcode molecule coupled to a bead, and a sequence of an assay primer.

As used herein, the term "click chemistry," generally refers to reactions that are modular, wide in scope, give high yields, generate only inoffensive byproducts, such as those that can be removed by nonchromatographic methods, and are stereospecific (but not necessarily enantioselective). See, e.g., Angew. Chem. Int. Ed., 2001, 40(11):2004-2021, which is entirely incorporated herein by reference for all purposes. In some cases, click chemistry can describe pairs of functional groups that can selectively react with each other in mild, aqueous conditions.

An example of click chemistry reaction can be the Huisgen 1,3-dipolar cycloaddition of an azide and an alkynes, i.e., Copper-catalyzed reaction of an azide with an alkyne to form a 5-membered heteroatom ring called 1,2,3-triazole. The reaction can also be known as a Cu(I)-Catalyzed Azide-Alkyne Cycloaddition (CuAAC), a Cu(I) click chemistry or a $Cu^+$ click chemistry. Catalyst for the click chemistry can be Cu(I) salts, or Cu(I) salts made in situ by reducing Cu(II) reagent to Cu(I) reagent with a reducing reagent (Pharm Res. 2008, 25(10): 2216-2230). Known Cu(II) reagents for the click chemistry can include, but are not limited to, Cu(II)-(TBTA) complex and Cu(II) (THPTA) complex. TBTA, which is tris-[(1-benzyl-1H-1,2,3-triazol-4-yl)methyl]amine, also known as tris-(benzyltriazolylmethyl)amine, can be a stabilizing ligand for Cu(I) salts. THPTA, which is tris-(hydroxypropyltriazolylmethyl) amine, can be another example of stabilizing agent for Cu(I). Other conditions can also be accomplished to construct the 1,2,3-triazole ring from an azide and an alkyne using copper-free click chemistry, such as by the Strain-promoted Azide-Alkyne Click chemistry reaction (SPAAC, see, e.g., Chem. Commun., 2011, 47:6257-6259 and Nature, 2015, 519 (7544):486-90), each of which is entirely incorporated herein by reference for all purposes.

Systems and Methods for Sample Compartmentalization

In an aspect, the systems and methods described herein provide for the compartmentalization, depositing, or partitioning of one or more particles (e.g., biological particles, macromolecular constituents of biological particles, beads, reagents, etc.) into discrete compartments or partitions (referred to interchangeably herein as partitions), where each partition maintains separation of its own contents from the contents of other partitions. The partition can be a droplet in an emulsion. A partition may comprise one or more other partitions.

A partition may include one or more particles. A partition may include one or more types of particles. For example, a partition of the present disclosure may comprise one or more biological particles and/or macromolecular constituents thereof. A partition may comprise one or more gel beads. A partition may comprise one or more cell beads. A partition may include a single gel bead, a single cell bead, or both a single cell bead and single gel bead. A partition may include one or more reagents. Alternatively, a partition may be unoccupied. For example, a partition may not comprise a bead. A cell bead can be a biological particle and/or one or more of its macromolecular constituents encased inside of a gel or polymer matrix, such as via polymerization of a droplet containing the biological particle and precursors capable of being polymerized or gelled. Unique identifiers, such as barcodes, may be injected into the droplets previous to, subsequent to, or concurrently with droplet generation, such as via a microcapsule (e.g., bead), as described elsewhere herein. Microfluidic channel networks (e.g., on a chip) can be utilized to generate partitions as described herein. Alternative mechanisms may also be employed in the partitioning of individual biological particles, including porous membranes through which aqueous mixtures of cells are extruded into non-aqueous fluids.

The partitions can be flowable within fluid streams. The partitions may comprise, for example, micro-vesicles that have an outer barrier surrounding an inner fluid center or core. In some cases, the partitions may comprise a porous matrix that is capable of entraining and/or retaining materials within its matrix. The partitions can be droplets of a first phase within a second phase, wherein the first and second phases are immiscible. For example, the partitions can be droplets of aqueous fluid within a non-aqueous continuous phase (e.g., oil phase). In another example, the partitions can be droplets of a non-aqueous fluid within an aqueous phase. In some examples, the partitions may be provided in a water-in-oil emulsion or oil-in-water emulsion. A variety of different vessels are described in, for example, U.S. Patent Application Publication No. 2014/0155295, which is entirely incorporated herein by reference for all purposes. Emulsion systems for creating stable droplets in non-aqueous or oil continuous phases are described in, for example, U.S. Patent Application Publication No. 2010/0105112, which is entirely incorporated herein by reference for all purposes.

In the case of droplets in an emulsion, allocating individual particles to discrete partitions may in one non-limiting example be accomplished by introducing a flowing stream of particles in an aqueous fluid into a flowing stream of a non-aqueous fluid, such that droplets are generated at the junction of the two streams. Fluid properties (e.g., fluid flow rates, fluid viscosities, etc.), particle properties (e.g., volume fraction, particle size, particle concentration, etc.), microfluidic architectures (e.g., channel geometry, etc.), and other parameters may be adjusted to control the occupancy of the resulting partitions (e.g., number of biological particles per partition, number of beads per partition, etc.). For example, partition occupancy can be controlled by providing the aqueous stream at a certain concentration and/or flow rate of particles. To generate single biological particle partitions, the relative flow rates of the immiscible fluids can be selected such that, on average, the partitions may contain less than one biological particle per partition in order to ensure that those partitions that are occupied are primarily singly occupied. In some cases, partitions among a plurality of partitions may contain at most one biological particle (e.g., bead, DNA, cell or cellular material). In some embodiments, the various parameters (e.g., fluid properties, particle properties, microfluidic architectures, etc.) may be selected or adjusted such that a majority of partitions are occupied, for example, allowing for only a small percentage of unoccupied partitions. The flows and channel architectures can be controlled as to ensure a given number of singly occupied partitions, less than a certain level of unoccupied partitions and/or less than a certain level of multiply occupied partitions.

FIG. 1 shows an example of a microfluidic channel structure 100 for partitioning individual biological particles. The channel structure 100 can include channel segments 102, 104, 106 and 108 communicating at a channel junction 110. In operation, a first aqueous fluid 112 that includes suspended biological particles (or cells) 114 may be transported along channel segment 102 into junction 110, while a second fluid 116 that is immiscible with the aqueous fluid 112 is delivered to the junction 110 from each of channel segments 104 and 106 to create discrete droplets 118, 120 of the first aqueous fluid 112 flowing into channel segment 108, and flowing away from junction 110. The channel segment 108 may be fluidically coupled to an outlet reservoir where the discrete droplets can be stored and/or harvested. A discrete droplet generated may include an individual biological particle 114 (such as droplets 118). A discrete droplet generated may include more than one individual biological particle 114 (not shown in FIG. 1). A discrete droplet may contain no biological particle 114 (such as droplet 120). Each discrete partition may maintain separation of its own contents (e.g., individual biological particle 114) from the contents of other partitions.

The second fluid 116 can comprise an oil, such as a fluorinated oil, that includes a fluorosurfactant for stabilizing the resulting droplets, for example, inhibiting subsequent coalescence of the resulting droplets 118, 120. Examples of particularly useful partitioning fluids and fluorosurfactants are described, for example, in U.S. Patent Application Publication No. 2010/0105112, which is entirely incorporated herein by reference for all purposes.

As will be appreciated, the channel segments described herein may be coupled to any of a variety of different fluid sources or receiving components, including reservoirs, tubing, manifolds, or fluidic components of other systems. As will be appreciated, the microfluidic channel structure 100 may have other geometries. For example, a microfluidic channel structure can have more than one channel junction. For example, a microfluidic channel structure can have 2, 3, 4, or 5 channel segments each carrying particles (e.g., biological particles, cell beads, and/or gel beads) that meet at a channel junction. Fluid may be directed to flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

The generated droplets may comprise two subsets of droplets: (1) occupied droplets 118, containing one or more biological particles 114, and (2) unoccupied droplets 120, not containing any biological particles 114. Occupied droplets 118 may comprise singly occupied droplets (having one biological particle) and multiply occupied droplets (having more than one biological particle). As described elsewhere herein, in some cases, the majority of occupied partitions can include no more than one biological particle per occupied partition and some of the generated partitions can be unoccupied (of any biological particle). In some cases, though, some of the occupied partitions may include more than one biological particle. In some cases, the partitioning process may be controlled such that fewer than about 25% of the occupied partitions contain more than one biological particle, and in many cases, fewer than about 20% of the occupied partitions have more than one biological particle, while in some cases, fewer than about 10% or even fewer than about 5% of the occupied partitions include more than one biological particle per partition.

In some cases, it may be desirable to minimize the creation of excessive numbers of empty partitions, such as to reduce costs and/or increase efficiency. While this minimization may be achieved by providing a sufficient number of biological particles (e.g., biological particles 114) at the partitioning junction 110, such as to ensure that at least one biological particle is encapsulated in a partition, the Poissonian distribution may expectedly increase the number of partitions that include multiple biological particles. As such, where singly occupied partitions are to be obtained, at most about 95%, 90%, 85%, 80%, 75%, 70%, 65%, 60%, 55%, 50%, 45%, 40%, 35%, 30%, 25%, 20%, 15%, 10%, 5% or less of the generated partitions can be unoccupied.

In some cases, the flow of one or more of the biological particles (e.g., in channel segment 102), or other fluids directed into the partitioning junction (e.g., in channel segments 104, 106) can be controlled such that, in many cases, no more than about 50% of the generated partitions, no more than about 25% of the generated partitions, or no more than about 10% of the generated partitions are unoccupied. These flows can be controlled so as to present a non-Poissonian distribution of single-occupied partitions while providing lower levels of unoccupied partitions. The above noted ranges of unoccupied partitions can be achieved while still providing any of the single occupancy rates described above. For example, in many cases, the use of the systems and methods described herein can create resulting partitions that have multiple occupancy rates of less than about 25%, less than about 20%, less than about 15%, less than about 10%, and in many cases, less than about 5%, while having unoccupied partitions of less than about 50%, less than about 40%, less than about 30%, less than about 20%, less than about 10%, less than about 5%, or less.

Figure 2:
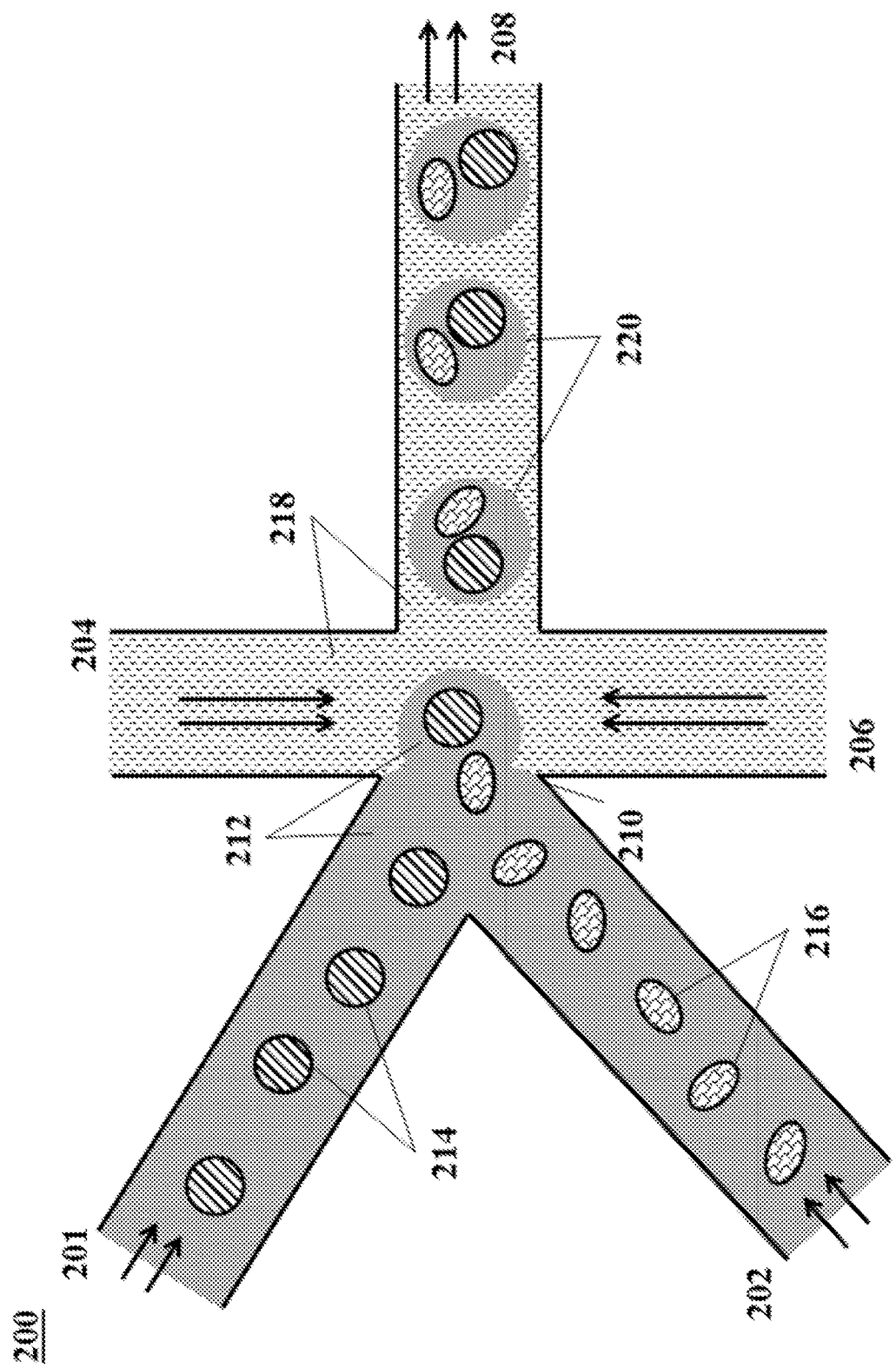
FIG. 2 shows an example of a microfluidic channel structure for delivering barcode carrying beads to droplets.

As will be appreciated, the above-described occupancy rates are also applicable to partitions that include both biological particles and additional reagents, including, but not limited to, microcapsules or beads (e.g., gel beads) carrying barcoded nucleic acid molecules (e.g., oligonucleotides) (described in relation to FIG. 2). The occupied partitions (e.g., at least about 10%, 20%, 30%, 40%, 50%, 60%, 70%, 80%, 90%, 95%, or 99% of the occupied partitions) can include both a microcapsule (e.g., bead) comprising barcoded nucleic acid molecules and a biological particle.

In another aspect, in addition to or as an alternative to droplet based partitioning, biological particles may be encapsulated within a microcapsule that comprises an outer shell, layer or porous matrix in which is entrained one or more individual biological particles or small groups of biological particles. The microcapsule may include other reagents. Encapsulation of biological particles may be performed by a variety of processes. Such processes may combine an aqueous fluid containing the biological particles with a polymeric precursor material that may be capable of being formed into a gel or other solid or semi-solid matrix upon application of a particular stimulus to the polymer precursor. Such stimuli can include, for example, thermal stimuli (e.g., either heating or cooling), photo-stimuli (e.g., through photo-curing), chemical stimuli (e.g., through cross-linking, polymerization initiation of the precursor (e.g., through added initiators)), mechanical stimuli, or a combination thereof.

Preparation of microcapsules comprising biological particles may be performed by a variety of methods. For example, air knife droplet or aerosol generators may be used to dispense droplets of precursor fluids into gelling solutions in order to form microcapsules that include individual biological particles or small groups of biological particles. Likewise, membrane based encapsulation systems may be used to generate microcapsules comprising encapsulated biological particles as described herein. Microfluidic systems of the present disclosure, such as that shown in FIG. 1, may be readily used in encapsulating cells as described herein. In particular, and with reference to FIG. 1, the aqueous fluid 112 comprising (i) the biological particles 114 and (ii) the polymer precursor material (not shown) is flowed into channel junction 110, where it is partitioned into droplets 118, 120 through the flow of non-aqueous fluid 116. In the case of encapsulation methods, non-aqueous fluid 116 may also include an initiator (not shown) to cause polymerization and/or crosslinking of the polymer precursor to form the microcapsule that includes the entrained biological particles. Examples of polymer precursor/initiator pairs include those described in U.S. Patent Application Publication No. 2014/0378345, which is entirely incorporated herein by reference for all purposes.

For example, in the case where the polymer precursor material comprises a linear polymer material, such as a linear polyacrylamide, PEG, or other linear polymeric material, the activation agent may comprise a cross-linking agent, or a chemical that activates a cross-linking agent within the formed droplets. Likewise, for polymer precursors that comprise polymerizable monomers, the activation agent may comprise a polymerization initiator. For example, in certain cases, where the polymer precursor comprises a mixture of acrylamide monomer with a N,N'-bis-(acryloyl) cystamine (BAC) comonomer, an agent such as tetraethylmethylenediamine (TEMED) may be provided within the second fluid streams 116 in channel segments 104 and 106, which can initiate the copolymerization of the acrylamide and BAC into a cross-linked polymer network, or hydrogel. Upon contact of the second fluid stream 116 with the first fluid stream 112 at junction 110, during formation of droplets, the TEMED may diffuse from the second fluid 116 into the aqueous fluid 112 comprising the linear polyacrylamide, which will activate the crosslinking of the polyacrylamide within the droplets 118, 120, resulting in the formation of gel (e.g., hydrogel) microcapsules, as solid or semi-solid beads or particles entraining the cells 114. Although described in terms of polyacrylamide encapsulation, other 'activatable' encapsulation compositions may also be employed in the context of the methods and compositions described herein. For example, formation of alginate droplets followed by exposure to divalent metal ions (e.g., $Ca^{2+}$ ions), can be used as an encapsulation process using the described processes. Likewise, agarose droplets may also be transformed into capsules through temperature based gelling (e.g., upon cooling, etc.).

In some cases, encapsulated biological particles can be selectively releasable from the microcapsule, such as through passage of time or upon application of a particular stimulus, that degrades the microcapsule sufficiently to allow the biological particles (e.g., cell), or its other contents to be released from the microcapsule, such as into a partition (e.g., droplet). For example, in the case of the polyacrylamide polymer described above, degradation of the microcapsule may be accomplished through the introduction of an appropriate reducing agent, such as DTT or the like, to cleave disulfide bonds that cross-link the polymer matrix. See, for example, U.S. Patent Application Publication No. 2014/0378345, which is entirely incorporated herein by reference for all purposes.

The biological particle can be subjected to other conditions sufficient to polymerize or gel the precursors. The conditions sufficient to polymerize or gel the precursors may comprise exposure to heating, cooling, electromagnetic radiation, and/or light. The conditions sufficient to polymerize or gel the precursors may comprise any conditions sufficient to polymerize or gel the precursors. Following polymerization or gelling, a polymer or gel may be formed around the biological particle. The polymer or gel may be diffusively permeable to chemical or biochemical reagents. The polymer or gel may be diffusively impermeable to macromolecular constituents of the biological particle. In this manner, the polymer or gel may act to allow the biological particle to be subjected to chemical or biochemical operations while spatially confining the macromolecular constituents to a region of the droplet defined by the polymer or gel. The polymer or gel may include one or more of disulfide cross-linked polyacrylamide, agarose, alginate, polyvinyl alcohol, polyethylene glycol (PEG)-diacrylate, PEG-acrylate, PEG-thiol, PEG-azide, PEG-alkyne, other acrylates, chitosan, hyaluronic acid, collagen, fibrin, gelatin, or elastin. The polymer or gel may comprise any other polymer or gel.

The polymer or gel may be functionalized to bind to targeted analytes, such as nucleic acids, proteins, carbohydrates, lipids or other analytes. The polymer or gel may be polymerized or gelled via a passive mechanism. The polymer or gel may be stable in alkaline conditions or at elevated temperature. The polymer or gel may have mechanical properties similar to the mechanical properties of the bead. For instance, the polymer or gel may be of a similar size to the bead. The polymer or gel may have a mechanical strength (e.g. tensile strength) similar to that of the bead. The polymer or gel may be of a lower density than an oil. The polymer or gel may be of a density that is roughly similar to that of a buffer. The polymer or gel may have a tunable pore size. The pore size may be chosen to, for instance, retain denatured nucleic acids. The pore size may be chosen to maintain diffusive permeability to exogenous chemicals such as sodium hydroxide (NaOH) and/or endogenous chemicals such as inhibitors. The polymer or gel may be biocompatible. The polymer or gel may maintain or enhance cell viability. The polymer or gel may be biochemically compatible. The polymer or gel may be polymerized and/or depolymerized thermally, chemically, enzymatically, and/or optically.

The polymer may comprise poly(acrylamide-co-acrylic acid) crosslinked with disulfide linkages. The preparation of the polymer may comprise a two-step reaction. In the first activation step, poly(acrylamide-co-acrylic acid) may be exposed to an acylating agent to convert carboxylic acids to esters. For instance, the poly(acrylamide-co-acrylic acid) may be exposed to 4-(4,6-dimethoxy-1,3,5-triazin-2-yl)-4-methylmorpholinium chloride (DMTMM). The polyacrylamide-co-acrylic acid may be exposed to other salts of 4-(4,6-dimethoxy-1,3,5-triazin-2-yl)-4-methylmorpholinium. In the second cross-linking step, the ester formed in the first step may be exposed to a disulfide crosslinking agent. For instance, the ester may be exposed to cystamine (2,2'-dithiobis(ethylamine)). Following the two steps, the biological particle may be surrounded by polyacrylamide strands linked together by disulfide bridges. In this manner, the biological particle may be encased inside of or comprise a gel or matrix (e.g., polymer matrix) to form a "cell bead." A cell bead can contain biological particles (e.g., a cell) or macromolecular constituents (e.g., RNA, DNA, proteins, etc.) of biological particles. A cell bead may include a single cell or multiple cells, or a derivative of the single cell or multiple cells. For example after lysing and washing the cells, inhibitory components from cell lysates can be washed away and the macromolecular constituents can be bound as cell beads. Systems and methods disclosed herein can be applicable to both cell beads (and/or droplets or other partitions) containing biological particles and cell beads (and/or droplets or other partitions) containing macromolecular constituents of biological particles.

Encapsulated biological particles can provide certain potential advantages of being more storable and more portable than droplet-based partitioned biological particles.

Furthermore, in some cases, it may be desirable to allow biological particles to incubate for a select period of time before analysis, such as in order to characterize changes in such biological particles over time, either in the presence or absence of different stimuli. In such cases, encapsulation may allow for longer incubation than partitioning in emulsion droplets, although in some cases, droplet partitioned biological particles may also be incubated for different periods of time, e.g., at least 10 seconds, at least 30 seconds, at least 1 minute, at least 5 minutes, at least 10 minutes, at least 30 minutes, at least 1 hour, at least 2 hours, at least 5 hours, or at least 10 hours or more. The encapsulation of biological particles may constitute the partitioning of the biological particles into which other reagents are co-partitioned. Alternatively or in addition, encapsulated biological particles may be readily deposited into other partitions (e.g., droplets) as described above.

Beads

A partition may comprise one or more unique identifiers, such as barcodes. Barcodes may be previously, subsequently or concurrently delivered to the partitions that hold the compartmentalized or partitioned biological particle. For example, barcodes may be injected into droplets previous to, subsequent to, or concurrently with droplet generation. The delivery of the barcodes to a particular partition allows for the later attribution of the characteristics of the individual biological particle to the particular partition. Barcodes may be delivered, for example on a nucleic acid molecule (e.g., an oligonucleotide), to a partition via any suitable mechanism. Barcoded nucleic acid molecules can be delivered to a partition via a microcapsule. A microcapsule, in some instances, can comprise a bead. Beads are described in further detail below.

In some cases, barcoded nucleic acid molecules can be initially associated with the microcapsule and then released from the microcapsule. Release of the barcoded nucleic acid molecules can be passive (e.g., by diffusion out of the microcapsule). In addition or alternatively, release from the microcapsule can be upon application of a stimulus which allows the barcoded nucleic acid nucleic acid molecules to dissociate or to be released from the microcapsule. Such stimulus may disrupt the microcapsule, an interaction that couples the barcoded nucleic acid molecules to or within the microcapsule, or both. Such stimulus can include, for example, a thermal stimulus, photo-stimulus, chemical stimulus (e.g., change in pH or use of a reducing agent(s)), a mechanical stimulus, a radiation stimulus; a biological stimulus (e.g., enzyme), or any combination thereof.

FIG. 2 shows an example of a microfluidic channel structure 200 for delivering barcode carrying beads to droplets. The channel structure 200 can include channel segments 201, 202, 204, 206 and 208 communicating at a channel junction 210. In operation, the channel segment 201 may transport an aqueous fluid 212 that includes a plurality of beads 214 (e.g., with nucleic acid molecules, oligonucleotides, molecular tags) along the channel segment 201 into junction 210. The plurality of beads 214 may be sourced from a suspension of beads. For example, the channel segment 201 may be connected to a reservoir comprising an aqueous suspension of beads 214. The channel segment 202 may transport the aqueous fluid 212 that includes a plurality of biological particles 216 along the channel segment 202 into junction 210. The plurality of biological particles 216 may be sourced from a suspension of biological particles. For example, the channel segment 202 may be connected to a reservoir comprising an aqueous suspension of biological particles 216. In some instances, the aqueous fluid 212 in either the first channel segment 201 or the second channel segment 202, or in both segments, can include one or more reagents, as further described below. A second fluid 218 that is immiscible with the aqueous fluid 212 (e.g., oil) can be delivered to the junction 210 from each of channel segments 204 and 206. Upon meeting of the aqueous fluid 212 from each of channel segments 201 and 202 and the second fluid 218 from each of channel segments 204 and 206 at the channel junction 210, the aqueous fluid 212 can be partitioned as discrete droplets 220 in the second fluid 218 and flow away from the junction 210 along channel segment 208. The channel segment 208 may deliver the discrete droplets to an outlet reservoir fluidly coupled to the channel segment 208, where they may be harvested.

As an alternative, the channel segments 201 and 202 may meet at another junction upstream of the junction 210. At such junction, beads and biological particles may form a mixture that is directed along another channel to the junction 210 to yield droplets 220. The mixture may provide the beads and biological particles in an alternating fashion, such that, for example, a droplet comprises a single bead and a single biological particle.

Beads, biological particles and droplets may flow along channels at substantially regular flow profiles (e.g., at regular flow rates). Such regular flow profiles may permit a droplet to include a single bead and a single biological particle. Such regular flow profiles may permit the droplets to have an occupancy (e.g., droplets having beads and biological particles) greater than 5%, 10%, 20%, 30%, 40%, 50%, 60%, 70%, 80%, 90%, or 95%. Such regular flow profiles and devices that may be used to provide such regular flow profiles are provided in, for example, U.S. Patent Publication No. 2015/0292988, which is entirely incorporated herein by reference.

The second fluid 218 can comprise an oil, such as a fluorinated oil, that includes a fluorosurfactant for stabilizing the resulting droplets, for example, inhibiting subsequent coalescence of the resulting droplets 220.

A discrete droplet that is generated may include an individual biological particle 216. A discrete droplet that is generated may include a barcode or other reagent carrying bead 214. A discrete droplet generated may include both an individual biological particle and a barcode carrying bead, such as droplets 220. In some instances, a discrete droplet may include more than one individual biological particle or no biological particle. In some instances, a discrete droplet may include more than one bead or no bead. A discrete droplet may be unoccupied (e.g., no beads, no biological particles).

Beneficially, a discrete droplet partitioning a biological particle and a barcode carrying bead may effectively allow the attribution of the barcode to macromolecular constituents of the biological particle within the partition. The contents of a partition may remain discrete from the contents of other partitions.

As will be appreciated, the channel segments described herein may be coupled to any of a variety of different fluid sources or receiving components, including reservoirs, tubing, manifolds, or fluidic components of other systems. As will be appreciated, the microfluidic channel structure 200 may have other geometries. For example, a microfluidic channel structure can have more than one channel junctions. For example, a microfluidic channel structure can have 2, 3, 4, or 5 channel segments each carrying beads that meet at a channel junction. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

A bead may be porous, non-porous, solid, semi-solid, semi-fluidic, fluidic, and/or a combination thereof. In some instances, a bead may be dissolvable, disruptable, and/or degradable. In some cases, a bead may not be degradable. In some cases, the bead may be a gel bead. A gel bead may be a hydrogel bead. A gel bead may be formed from molecular precursors, such as a polymeric or monomeric species. A semi-solid bead may be a liposomal bead. Solid beads may comprise metals including iron oxide, gold, and silver. In some cases, the bead may be a silica bead. In some cases, the bead can be rigid. In other cases, the bead may be flexible and/or compressible.

A bead may be of any suitable shape. Examples of bead shapes include, but are not limited to, spherical, non-spherical, oval, oblong, amorphous, circular, cylindrical, and variations thereof.

Beads may be of uniform size or heterogeneous size. In some cases, the diameter of a bead may be at least about 10 nanometers (nm), 100 nm, 500 nm, 1 micrometer (µm), 5 µm, 10 µm, 20 µm, 30 µm, 40 µm, 50 µm, 60 µm, 70 µm, 80 µm, 90 µm, 100 µm, 250 µm, 500 µm, 1 mm, or greater. In some cases, a bead may have a diameter of less than about 10 nm, 100 nm, 500 nm, 1 µm, 5 µm, 10 µm, 20 µm, 30 µm, 40 µm, 50 µm, 60 µm, 70 µm, 80 µm, 90 µm, 100 µm, 250 µm, 500 µm, 1 mm, or less. In some cases, a bead may have a diameter in the range of about 40-75 µm, 30-75 µm, 20-75 µm, 40-85 µm, 40-95 µm, 20-100 µm, 10-100 µm, 1-100 µm, 20-250 µm, or 20-500 µm.

In certain aspects, beads can be provided as a population or plurality of beads having a relatively monodisperse size distribution. Where it may be desirable to provide relatively consistent amounts of reagents within partitions, maintaining relatively consistent bead characteristics, such as size, can contribute to the overall consistency. In particular, the beads described herein may have size distributions that have a coefficient of variation in their cross-sectional dimensions of less than 50%, less than 40%, less than 30%, less than 20%, and in some cases less than 15%, less than 10%, less than 5%, or less.

A bead may comprise natural and/or synthetic materials. For example, a bead can comprise a natural polymer, a synthetic polymer or both natural and synthetic polymers. Examples of natural polymers include proteins and sugars such as deoxyribonucleic acid, rubber, cellulose, starch (e.g., amylose, amylopectin), proteins, enzymes, polysaccharides, silks, polyhydroxyalkanoates, chitosan, dextran, collagen, carrageenan, ispaghula, acacia, agar, gelatin, shellac, sterculia gum, xanthan gum, Corn sugar gum, guar gum, gum karaya, agarose, alginic acid, alginate, or natural polymers thereof. Examples of synthetic polymers include acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly(tetrafluoroethylene), poly (vinyl acetate), poly(vinyl alcohol), poly(vinyl chloride), poly(vinylidene dichloride), poly(vinylidene difluoride), poly(vinyl fluoride) and/or combinations (e.g., co-polymers) thereof. Beads may also be formed from materials other than polymers, including lipids, micelles, ceramics, glass-ceramics, material composites, metals, other inorganic materials, and others.

In some instances, the bead may contain molecular precursors (e.g., monomers or polymers), which may form a polymer network via polymerization of the molecular precursors. In some cases, a precursor may be an already polymerized species capable of undergoing further polymerization via, for example, a chemical cross-linkage. In some cases, a precursor can comprise one or more of an acrylamide or a methacrylamide monomer, oligomer, or polymer. In some cases, the bead may comprise prepolymers, which are oligomers capable of further polymerization. For example, polyurethane beads may be prepared using prepolymers. In some cases, the bead may contain individual polymers that may be further polymerized together. In some cases, beads may be generated via polymerization of different precursors, such that they comprise mixed polymers, co-polymers, and/or block co-polymers. In some cases, the bead may comprise covalent or ionic bonds between polymeric precursors (e.g., monomers, oligomers, linear polymers), nucleic acid molecules (e.g., oligonucleotides), primers, and other entities. In some cases, the covalent bonds can be carbon-carbon bonds, thioether bonds, or carbon-heteroatom bonds.

Cross-linking may be permanent or reversible, depending upon the particular cross-linker used. Reversible cross-linking may allow for the polymer to linearize or dissociate under appropriate conditions. In some cases, reversible cross-linking may also allow for reversible attachment of a material bound to the surface of a bead. In some cases, a cross-linker may form disulfide linkages. In some cases, the chemical cross-linker forming disulfide linkages may be cystamine or a modified cystamine.

In some cases, disulfide linkages can be formed between molecular precursor units (e.g., monomers, oligomers, or linear polymers) or precursors incorporated into a bead and nucleic acid molecules (e.g., oligonucleotides). Cystamine (including modified cystamines), for example, is an organic agent comprising a disulfide bond that may be used as a crosslinker agent between individual monomeric or polymeric precursors of a bead. Polyacrylamide may be polymerized in the presence of cystamine or a species comprising cystamine (e.g., a modified cystamine) to generate polyacrylamide gel beads comprising disulfide linkages (e.g., chemically degradable beads comprising chemically-reducible cross-linkers). The disulfide linkages may permit the bead to be degraded (or dissolved) upon exposure of the bead to a reducing agent.

In some cases, chitosan, a linear polysaccharide polymer, may be crosslinked with glutaraldehyde via hydrophilic chains to form a bead. Crosslinking of chitosan polymers may be achieved by chemical reactions that are initiated by heat, pressure, change in pH, and/or radiation.

In some cases, a bead may comprise an acrydite moiety, which in certain aspects may be used to attach one or more nucleic acid molecules (e.g., barcode sequence, barcoded nucleic acid molecule, barcoded oligonucleotide, primer, or other oligonucleotide) to the bead. In some cases, an acrydite moiety can refer to an acrydite analogue generated from the reaction of acrydite with one or more species, such as, the reaction of acrydite with other monomers and cross-linkers during a polymerization reaction. Acrydite moieties may be modified to form chemical bonds with a species to be attached, such as a nucleic acid molecule (e.g., barcode sequence, barcoded nucleic acid molecule, barcoded oligonucleotide, primer, or other oligonucleotide). Acrydite moieties may be modified with thiol groups capable of forming a disulfide bond or may be modified with groups already comprising a disulfide bond. The thiol or disulfide (via disulfide exchange) may be used as an anchor point for a species to be attached or another part of the acrydite moiety may be used for attachment. In some cases, attachment can be reversible, such that when the disulfide bond is broken (e.g., in the presence of a reducing agent), the attached species is released from the bead. In other cases, an acrydite moiety can comprise a reactive hydroxyl group that may be used for attachment.

Functionalization of beads for attachment of nucleic acid molecules (e.g., oligonucleotides) may be achieved through a wide range of different approaches, including activation of chemical groups within a polymer, incorporation of active or activatable functional groups in the polymer structure, or attachment at the pre-polymer or monomer stage in bead production.

For example, precursors (e.g., monomers, cross-linkers) that are polymerized to form a bead may comprise acrydite moieties, such that when a bead is generated, the bead also comprises acrydite moieties. The acrydite moieties can be attached to a nucleic acid molecule (e.g., oligonucleotide), which may include a priming sequence (e.g., a primer for amplifying target nucleic acids, random primer, primer sequence for messenger RNA) and/or one or more barcode sequences. The one more barcode sequences may include sequences that are the same for all nucleic acid molecules coupled to a given bead and/or sequences that are different across all nucleic acid molecules coupled to the given bead. The nucleic acid molecule may be incorporated into the bead.

In some cases, the nucleic acid molecule can comprise a functional sequence, for example, for attachment to a sequencing flow cell, such as, for example, a P5 sequence for Illumina® sequencing. In some cases, the nucleic acid molecule or derivative thereof (e.g., oligonucleotide or polynucleotide generated from the nucleic acid molecule) can comprise another functional sequence, such as, for example, a P7 sequence for attachment to a sequencing flow cell for Illumina sequencing. In some cases, the nucleic acid molecule can comprise a barcode sequence. In some cases, the primer can further comprise a unique molecular identifier (UMI). In some cases, the primer can comprise an R1 primer sequence for Illumina sequencing. In some cases, the primer can comprise an R2 primer sequence for Illumina sequencing. Examples of such nucleic acid molecules (e.g., oligonucleotides, polynucleotides, etc.) and uses thereof, as may be used with compositions, devices, methods and systems of the present disclosure, are provided in U.S. Patent Pub. Nos. 2014/0378345 and 2015/0376609, each of which is entirely incorporated herein by reference.

Figure 8:
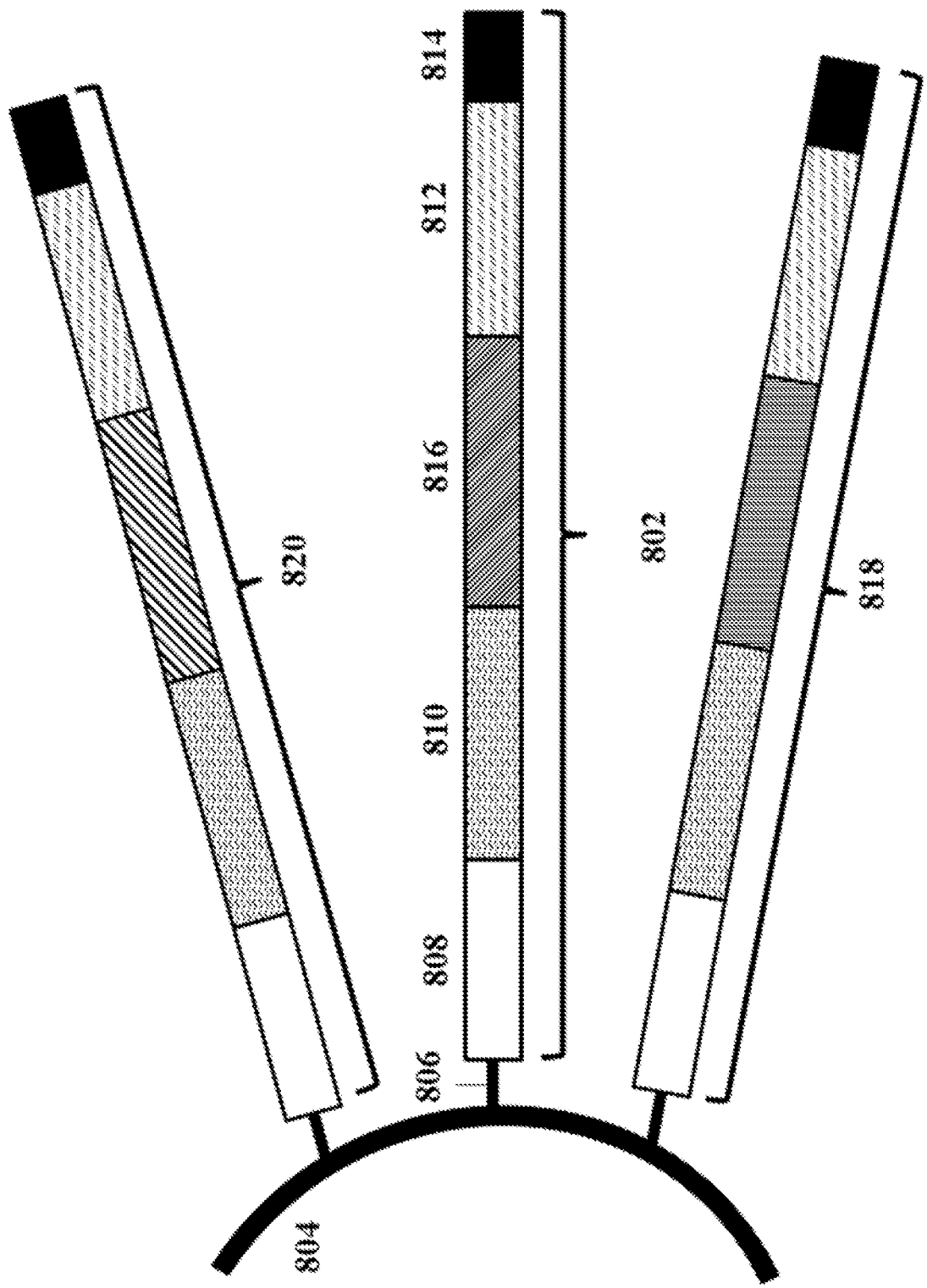
FIG. 8 illustrates an example of a barcode carrying bead.

FIG. 8 illustrates an example of a barcode carrying bead. A nucleic acid molecule 802, such as an oligonucleotide, can be coupled to a bead 804 by a releasable linkage 806, such as, for example, a disulfide linker. The same bead 804 may be coupled (e.g., via releasable linkage) to one or more other nucleic acid molecules 818, 820. The nucleic acid molecule 802 may be or comprise a barcode. As noted elsewhere herein, the structure of the barcode may comprise a number of sequence elements. The nucleic acid molecule 802 may comprise a functional sequence 808 that may be used in subsequent processing. For example, the functional sequence 808 may include one or more of a sequencer specific flow cell attachment sequence (e.g., a P5 sequence for Illumina® sequencing systems) and a sequencing primer sequence (e.g., a R1 primer for Illumina® sequencing systems). The nucleic acid molecule 802 may comprise a barcode sequence 810 for use in barcoding the sample (e.g., DNA, RNA, protein, etc.). In some cases, the barcode sequence 810 can be bead-specific such that the barcode sequence 810 is common to all nucleic acid molecules (e.g., including nucleic acid molecule 802) coupled to the same bead 804. Alternatively or in addition, the barcode sequence 810 can be partition-specific such that the barcode sequence 810 is common to all nucleic acid molecules coupled to one or more beads that are partitioned into the same partition. The nucleic acid molecule 802 may comprise a specific priming sequence 812, such as an mRNA specific priming sequence (e.g., poly-T sequence), a targeted priming sequence, and/or a random priming sequence. The nucleic acid molecule 802 may comprise an anchoring sequence 814 to ensure that the specific priming sequence 812 hybridizes at the sequence end (e.g., of the mRNA). For example, the anchoring sequence 814 can include a random short sequence of nucleotides, such as a 1-mer, 2-mer, 3-mer or longer sequence, which can ensure that a poly-T segment is more likely to hybridize at the sequence end of the poly-A tail of the mRNA.

The nucleic acid molecule 802 may comprise a unique molecular identifying sequence 816 (e.g., unique molecular identifier (UMI)). In some cases, the unique molecular identifying sequence 816 may comprise from about 5 to about 8 nucleotides. Alternatively, the unique molecular identifying sequence 816 may compress less than about 5 or more than about 8 nucleotides. The unique molecular identifying sequence 816 may be a unique sequence that varies across individual nucleic acid molecules (e.g., 802, 818, 820, etc.) coupled to a single bead (e.g., bead 804). In some cases, the unique molecular identifying sequence 816 may be a random sequence (e.g., such as a random N-mer sequence). For example, the UMI may provide a unique identifier of the starting mRNA molecule that was captured, in order to allow quantitation of the number of original expressed RNA. As will be appreciated, although FIG. 8 shows three nucleic acid molecules 802, 818, 820 coupled to the surface of the bead 804, an individual bead may be coupled to any number of individual nucleic acid molecules, for example, from one to tens to hundreds of thousands or even millions of individual nucleic acid molecules. The respective barcodes for the individual nucleic acid molecules can comprise both common sequence segments or relatively common sequence segments (e.g., 808, 810, 812, etc.) and variable or unique sequence segments (e.g., 816) between different individual nucleic acid molecules coupled to the same bead.

In operation, a biological particle (e.g., cell, DNA, RNA, etc.) can be co-partitioned along with a barcode bearing bead 804. The barcoded nucleic acid molecules 802, 818, 820 can be released from the bead 804 in the partition. By way of example, in the context of analyzing sample RNA, the poly-T segment (e.g., 812) of one of the released nucleic acid molecules (e.g., 802) can hybridize to the poly-A tail of a mRNA molecule. Reverse transcription may result in a cDNA transcript of the mRNA, but which transcript includes each of the sequence segments 808, 810, 816 of the nucleic acid molecule 802. Because the nucleic acid molecule 802 comprises an anchoring sequence 814, it will more likely hybridize to and prime reverse transcription at the sequence end of the poly-A tail of the mRNA. Within any given partition, all of the cDNA transcripts of the individual mRNA molecules may include a common barcode sequence segment 810. However, the transcripts made from the different mRNA molecules within a given partition may vary at the unique molecular identifying sequence 812 segment (e.g., UMI segment). Beneficially, even following any subsequent amplification of the contents of a given partition, the number of different UMIs can be indicative of the quantity of mRNA originating from a given partition, and thus from the biological particle (e.g., cell). As noted above, the transcripts can be amplified, cleaned up and sequenced to identify the sequence of the cDNA transcript of the mRNA, as well as to sequence the barcode segment and the UMI segment. While a poly-T primer sequence is described, other targeted or random priming sequences may also be used in priming the reverse transcription reaction. Likewise, although described as releasing the barcoded oligonucleotides into the partition, in some cases, the nucleic acid molecules bound to the bead (e.g., gel bead) may be used to hybridize and capture the mRNA on the solid phase of the bead, for example, in order to facilitate the separation of the RNA from other cell contents.

In some cases, precursors comprising a functional group that is reactive or capable of being activated such that it becomes reactive can be polymerized with other precursors to generate gel beads comprising the activated or activatable functional group. The functional group may then be used to attach additional species (e.g., disulfide linkers, primers, other oligonucleotides, etc.) to the gel beads. For example, some precursors comprising a carboxylic acid (COOH) group can co-polymerize with other precursors to form a gel bead that also comprises a COOH functional group. In some cases, acrylic acid (a species comprising free COOH groups), acrylamide, and bis(acryloyl)cystamine can be co-polymerized together to generate a gel bead comprising free COOH groups. The COOH groups of the gel bead can be activated (e.g., via 1-Ethyl-3-(3-dimethylaminopropyl)carbodiimide (EDC) and N-Hydroxysuccinimide (NHS) or 4-(4,6-Dimethoxy-1,3,5-triazin-2-yl)-4-methylmorpholinium chloride (DMTMM)) such that they are reactive (e.g., reactive to amine functional groups where EDC/NHS or DMTMM are used for activation). The activated COOH groups can then react with an appropriate species (e.g., a species comprising an amine functional group where the carboxylic acid groups are activated to be reactive with an amine functional group) comprising a moiety to be linked to the bead.

Beads comprising disulfide linkages in their polymeric network may be functionalized with additional species via reduction of some of the disulfide linkages to free thiols. The disulfide linkages may be reduced via, for example, the action of a reducing agent (e.g., DTT, TCEP, etc.) to generate free thiol groups, without dissolution of the bead. Free thiols of the beads can then react with free thiols of a species or a species comprising another disulfide bond (e.g., via thiol-disulfide exchange) such that the species can be linked to the beads (e.g., via a generated disulfide bond). In some cases, free thiols of the beads may react with any other suitable group. For example, free thiols of the beads may react with species comprising an acrydite moiety. The free thiol groups of the beads can react with the acrydite via Michael addition chemistry, such that the species comprising the acrydite is linked to the bead. In some cases, uncontrolled reactions can be prevented by inclusion of a thiol capping agent such as N-ethylmalieamide or iodoacetate.

Activation of disulfide linkages within a bead can be controlled such that only a small number of disulfide linkages are activated. Control may be exerted, for example, by controlling the concentration of a reducing agent used to generate free thiol groups and/or concentration of reagents used to form disulfide bonds in bead polymerization. In some cases, a low concentration (e.g., molecules of reducing agent:gel bead ratios of less than or equal to about 1:100,000,000,000, less than or equal to about 1:10,000,000,000, less than or equal to about 1:1,000,000,000, less than or equal to about 1:100,000,000, less than or equal to about 1:10,000,000, less than or equal to about 1:1,000,000, less than or equal to about 1:100,000, less than or equal to about 1:10,000) of reducing agent may be used for reduction. Controlling the number of disulfide linkages that are reduced to free thiols may be useful in ensuring bead structural integrity during functionalization. In some cases, optically-active agents, such as fluorescent dyes may be coupled to beads via free thiol groups of the beads and used to quantify the number of free thiols present in a bead and/or track a bead.

In some cases, addition of moieties to a gel bead after gel bead formation may be advantageous. For example, addition of an oligonucleotide (e.g., barcoded oligonucleotide) after gel bead formation may avoid loss of the species during chain transfer termination that can occur during polymerization. Moreover, smaller precursors (e.g., monomers or cross linkers that do not comprise side chain groups and linked moieties) may be used for polymerization and can be minimally hindered from growing chain ends due to viscous effects. In some cases, functionalization after gel bead synthesis can minimize exposure of species (e.g., oligonucleotides) to be loaded with potentially damaging agents (e.g., free radicals) and/or chemical environments. In some cases, the generated gel may possess an upper critical solution temperature (UCST) that can permit temperature driven swelling and collapse of a bead. Such functionality may aid in oligonucleotide (e.g., a primer) infiltration into the bead during subsequent functionalization of the bead with the oligonucleotide. Post-production functionalization may also be useful in controlling loading ratios of species in beads, such that, for example, the variability in loading ratio is minimized. Species loading may also be performed in a batch process such that a plurality of beads can be functionalized with the species in a single batch.

A bead injected or otherwise introduced into a partition may comprise releasably, cleavably, or reversibly attached barcodes. A bead injected or otherwise introduced into a partition may comprise activatable barcodes. A bead injected or otherwise introduced into a partition may be degradable, disruptable, or dissolvable beads.

Barcodes can be releasably, cleavably or reversibly attached to the beads such that barcodes can be released or be releasable through cleavage of a linkage between the barcode molecule and the bead, or released through degradation of the underlying bead itself, allowing the barcodes to be accessed or be accessible by other reagents, or both. In non-limiting examples, cleavage may be achieved through reduction of di-sulfide bonds, use of restriction enzymes, photo-activated cleavage, or cleavage via other types of stimuli (e.g., chemical, thermal, pH, enzymatic, etc.) and/or reactions, such as described elsewhere herein. Releasable barcodes may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to, or as an alternative to the cleavable linkages between the beads and the associated molecules, such as barcode containing nucleic acid molecules (e.g., barcoded oligonucleotides), the beads may be degradable, disruptable, or dissolvable spontaneously or upon exposure to one or more stimuli (e.g., temperature changes, pH changes, exposure to particular chemical species or phase, exposure to light, reducing agent, etc.). In some cases, a bead may be dissolvable, such that material components of the beads are solubilized when exposed to a particular chemical species or an environmental change, such as a change temperature or a change in pH. In some cases, a gel bead can be degraded or dissolved at elevated temperature and/or in basic conditions. In some cases, a bead may be thermally degradable such that when the bead is exposed to an appropriate change in temperature (e.g., heat), the bead degrades. Degradation or dissolution of a bead bound to a species (e.g., a nucleic acid molecule, e.g., barcoded oligonucleotide) may result in release of the species from the bead.

As will be appreciated from the above disclosure, the degradation of a bead may refer to the disassociation of a bound or entrained species from a bead, both with and without structurally degrading the physical bead itself. For example, the degradation of the bead may involve cleavage of a cleavable linkage via one or more species and/or methods described elsewhere herein. In another example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

A degradable bead may be introduced into a partition, such as a droplet of an emulsion or a well, such that the bead degrades within the partition and any associated species (e.g., oligonucleotides) are released within the droplet when the appropriate stimulus is applied. The free species (e.g., oligonucleotides, nucleic acid molecules) may interact with other reagents contained in the partition. For example, a polyacrylamide bead comprising cystamine and linked, via a disulfide bond, to a barcode sequence, may be combined with a reducing agent within a droplet of a water-in-oil emulsion. Within the droplet, the reducing agent can break the various disulfide bonds, resulting in bead degradation and release of the barcode sequence into the aqueous, inner environment of the droplet. In another example, heating of a droplet comprising a bead-bound barcode sequence in basic solution may also result in bead degradation and release of the attached barcode sequence into the aqueous, inner environment of the droplet.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing nucleic acid molecule (e.g., oligonucleotide) bearing beads.

In some cases, beads can be non-covalently loaded with one or more reagents. The beads can be non-covalently loaded by, for instance, subjecting the beads to conditions sufficient to swell the beads, allowing sufficient time for the reagents to diffuse into the interiors of the beads, and subjecting the beads to conditions sufficient to de-swell the beads. The swelling of the beads may be accomplished, for instance, by placing the beads in a thermodynamically favorable solvent, subjecting the beads to a higher or lower temperature, subjecting the beads to a higher or lower ion concentration, and/or subjecting the beads to an electric field. The swelling of the beads may be accomplished by various swelling methods. The de-swelling of the beads may be accomplished, for instance, by transferring the beads in a thermodynamically unfavorable solvent, subjecting the beads to lower or high temperatures, subjecting the beads to a lower or higher ion concentration, and/or removing an electric field. The de-swelling of the beads may be accomplished by various de-swelling methods. Transferring the beads may cause pores in the bead to shrink. The shrinking may then hinder reagents within the beads from diffusing out of the interiors of the beads. The hindrance may be due to steric interactions between the reagents and the interiors of the beads. The transfer may be accomplished microfluidically. For instance, the transfer may be achieved by moving the beads from one co-flowing solvent stream to a different co-flowing solvent stream. The swellability and/or pore size of the beads may be adjusted by changing the polymer composition of the bead.

In some cases, an acrydite moiety linked to a precursor, another species linked to a precursor, or a precursor itself can comprise a labile bond, such as chemically, thermally, or photo-sensitive bond e.g., disulfide bond, UV sensitive bond, or the like. Once acrydite moieties or other moieties comprising a labile bond are incorporated into a bead, the bead may also comprise the labile bond. The labile bond may be, for example, useful in reversibly linking (e.g., covalently linking) species (e.g., barcodes, primers, etc.) to a bead. In some cases, a thermally labile bond may include a nucleic acid hybridization based attachment, e.g., where an oligonucleotide is hybridized to a complementary sequence that is attached to the bead, such that thermal melting of the hybrid releases the oligonucleotide, e.g., a barcode containing sequence, from the bead or microcapsule.

The addition of multiple types of labile bonds to a gel bead may result in the generation of a bead capable of responding to varied stimuli. Each type of labile bond may be sensitive to an associated stimulus (e.g., chemical stimulus, light, temperature, enzymatic, etc.) such that release of species attached to a bead via each labile bond may be controlled by the application of the appropriate stimulus. Such functionality may be useful in controlled release of species from a gel bead. In some cases, another species comprising a labile bond may be linked to a gel bead after gel bead formation via, for example, an activated functional group of the gel bead as described above. As will be appreciated, barcodes that are releasably, cleavably or reversibly attached to the beads described herein include barcodes that are released or releasable through cleavage of a linkage between the barcode molecule and the bead, or that are released through degradation of the underlying bead itself, allowing the barcodes to be accessed or accessible by other reagents, or both.

The barcodes that are releasable as described herein may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to thermally cleavable bonds, disulfide bonds and UV sensitive bonds, other non-limiting examples of labile bonds that may be coupled to a precursor or bead include an ester linkage (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNAase)). A bond may be cleavable via other nucleic acid molecule targeting enzymes, such as restriction enzymes (e.g., restriction endonucleases), as described further below.

Species may be encapsulated in beads during bead generation (e.g., during polymerization of precursors). Such species may or may not participate in polymerization. Such species may be entered into polymerization reaction mixtures such that generated beads comprise the species upon bead formation. In some cases, such species may be added to the gel beads after formation. Such species may include, for example, nucleic acid molecules (e.g., oligonucleotides), reagents for a nucleic acid amplification reaction (e.g., primers, polymerases, dNTPs, co-factors (e.g., ionic co-factors), buffers) including those described herein, reagents for enzymatic reactions (e.g., enzymes, co-factors, substrates, buffers), reagents for nucleic acid modification reactions such as polymerization, ligation, or digestion, and/or reagents for template preparation (e.g., tagmentation) for one or more sequencing platforms (e.g., Nextera® for Illumina®). Such species may include one or more enzymes described herein, including without limitation, polymerase, reverse transcriptase, restriction enzymes (e.g., endonuclease), transposase, ligase, proteinase K, DNAse, etc. Such species may include one or more reagents described elsewhere herein (e.g., lysis agents, inhibitors, inactivating agents, chelating agents, stimulus). Trapping of such species may be controlled by the polymer network density generated during polymerization of precursors, control of ionic charge within the gel bead (e.g., via ionic species linked to polymerized species), or by the release of other species. Encapsulated species may be released from a bead upon bead degradation and/or by application of a stimulus capable of releasing the species from the bead. Alternatively or in addition, species may be partitioned in a partition (e.g., droplet) during or subsequent to partition formation. Such species may include, without limitation, the abovementioned species that may also be encapsulated in a bead.

A degradable bead may comprise one or more species with a labile bond such that, when the bead/species is exposed to the appropriate stimuli, the bond is broken and the bead degrades. The labile bond may be a chemical bond (e.g., covalent bond, ionic bond) or may be another type of physical interaction (e.g., van der Waals interactions, dipole-dipole interactions, etc.). In some cases, a crosslinker used to generate a bead may comprise a labile bond. Upon exposure to the appropriate conditions, the labile bond can be broken and the bead degraded. For example, upon exposure of a polyacrylamide gel bead comprising cystamine crosslinkers to a reducing agent, the disulfide bonds of the cystamine can be broken and the bead degraded.

A degradable bead may be useful in more quickly releasing an attached species (e.g., a nucleic acid molecule, a barcode sequence, a primer, etc) from the bead when the appropriate stimulus is applied to the bead as compared to a bead that does not degrade. For example, for a species bound to an inner surface of a porous bead or in the case of an encapsulated species, the species may have greater mobility and accessibility to other species in solution upon degradation of the bead. In some cases, a species may also be attached to a degradable bead via a degradable linker (e.g., disulfide linker). The degradable linker may respond to the same stimuli as the degradable bead or the two degradable species may respond to different stimuli. For example, a barcode sequence may be attached, via a disulfide bond, to a polyacrylamide bead comprising cystamine. Upon exposure of the barcoded-bead to a reducing agent, the bead degrades and the barcode sequence is released upon breakage of both the disulfide linkage between the barcode sequence and the bead and the disulfide linkages of the cystamine in the bead.

As will be appreciated from the above disclosure, while referred to as degradation of a bead, in many instances as noted above, that degradation may refer to the disassociation of a bound or entrained species from a bead, both with and without structurally degrading the physical bead itself. For example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

Where degradable beads are provided, it may be beneficial to avoid exposing such beads to the stimulus or stimuli that cause such degradation prior to a given time, in order to, for example, avoid premature bead degradation and issues that arise from such degradation, including for example poor flow characteristics and aggregation. By way of example, where beads comprise reducible cross-linking groups, such as disulfide groups, it will be desirable to avoid contacting such beads with reducing agents, e.g., DTT or other disulfide cleaving reagents. In such cases, treatment to the beads described herein will, in some cases be provided free of reducing agents, such as DTT. Because reducing agents are often provided in commercial enzyme preparations, it may be desirable to provide reducing agent free (or DTT free) enzyme preparations in treating the beads described herein. Examples of such enzymes include, e.g., polymerase enzyme preparations, reverse transcriptase enzyme preparations, ligase enzyme preparations, as well as many other enzyme preparations that may be used to treat the beads described herein. The terms "reducing agent free" or "DTT free" preparations can refer to a preparation having less than about 1/10th, less than about 1/50th, or even less than about 1/100th of the lower ranges for such materials used in degrading the beads. For example, for DTT, the reducing agent free preparation can have less than about 0.01 millimolar (mM), 0.005 mM, 0.001 mM DTT, 0.0005 mM DTT, or even less than about 0.0001 mM DTT. In many cases, the amount of DTT can be undetectable.

Numerous chemical triggers may be used to trigger the degradation of beads. Examples of these chemical changes may include, but are not limited to pH-mediated changes to the integrity of a component within the bead, degradation of a component of a bead via cleavage of cross-linked bonds, and depolymerization of a component of a bead.

In some embodiments, a bead may be formed from materials that comprise degradable chemical crosslinkers, such as BAC or cystamine. Degradation of such degradable crosslinkers may be accomplished through a number of mechanisms. In some examples, a bead may be contacted with a chemical degrading agent that may induce oxidation, reduction or other chemical changes. For example, a chemical degrading agent may be a reducing agent, such as dithiothreitol (DTT). Additional examples of reducing agents may include (3-mercaptoethanol, (2S)-2-amino-1,4-dimercaptobutane (dithiobutylamine or DTBA), tris(2-carboxyethyl) phosphine (TCEP), or combinations thereof. A reducing agent may degrade the disulfide bonds formed between gel precursors forming the bead, and thus, degrade the bead. In other cases, a change in pH of a solution, such as an increase in pH, may trigger degradation of a bead. In other cases, exposure to an aqueous solution, such as water, may trigger hydrolytic degradation, and thus degradation of the bead. In some cases, any combination of stimuli may trigger degradation of a bead. For example, a change in pH may enable a chemical agent (e.g., DTT) to become an effective reducing agent.

Beads may also be induced to release their contents upon the application of a thermal stimulus. A change in temperature can cause a variety of changes to a bead. For example, heat can cause a solid bead to liquefy. A change in heat may cause melting of a bead such that a portion of the bead degrades. In other cases, heat may increase the internal pressure of the bead components such that the bead ruptures or explodes. Heat may also act upon heat-sensitive polymers used as materials to construct beads.

Any suitable agent may degrade beads. In some embodiments, changes in temperature or pH may be used to degrade thermo-sensitive or pH-sensitive bonds within beads. In some embodiments, chemical degrading agents may be used to degrade chemical bonds within beads by oxidation, reduction or other chemical changes. For example, a chemical degrading agent may be a reducing agent, such as DTT, wherein DTT may degrade the disulfide bonds formed between a crosslinker and gel precursors, thus degrading the bead. In some embodiments, a reducing agent may be added to degrade the bead, which may or may not cause the bead to release its contents. Examples of reducing agents may include dithiothreitol (DTT), (3-mercaptoethanol, (2S)-2-amino-1,4-dimercaptobutane (dithiobutylamine or DTBA), tris(2-carboxyethyl) phosphine (TCEP), or combinations thereof. The reducing agent may be present at a concentration of about 0.1 mM, 0.5 mM, 1 mM, 5 mM, 10 mM. The reducing agent may be present at a concentration of at least about 0.1 mM, 0.5 mM, 1 mM, 5 mM, 10 mM, or greater than 10 mM. The reducing agent may be present at concentration of at most about 10 mM, 5 mM, 1 mM, 0.5 mM, 0.1 mM, or less.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing oligonucleotide bearing beads.

Although FIG. 1 and FIG. 2 have been described in terms of providing substantially singly occupied partitions, above, in certain cases, it may be desirable to provide multiply occupied partitions, e.g., containing two, three, four or more cells and/or microcapsules (e.g., beads) comprising barcoded nucleic acid molecules (e.g., oligonucleotides) within a single partition. Accordingly, as noted above, the flow characteristics of the biological particle and/or bead containing fluids and partitioning fluids may be controlled to provide for such multiply occupied partitions. In particular, the flow parameters may be controlled to provide a given occupancy rate at greater than about 50% of the partitions, greater than about 75%, and in some cases greater than about 80%, 90%, 95%, or higher.

In some cases, additional microcapsules can be used to deliver additional reagents to a partition. In such cases, it may be advantageous to introduce different beads into a common channel or droplet generation junction, from different bead sources (e.g., containing different associated reagents) through different channel inlets into such common channel or droplet generation junction (e.g., junction 210). In such cases, the flow and frequency of the different beads into the channel or junction may be controlled to provide for a certain ratio of microcapsules from each source, while ensuring a given pairing or combination of such beads into a partition with a given number of biological particles (e.g., one biological particle and one bead per partition).

The partitions described herein may comprise small volumes, for example, less than about 10 microliters (µL), 5 µL, 900 picoliters (pL), 800 pL, 700 pL, 600 pL, 500 pL, 400 pL, 300 pL, 200 pL, 100 pL, 50 pL, 20 pL, 10 pL, 1 pL, 500 nanoliters (nL), 100 nL, 50 nL, or less.

For example, in the case of droplet based partitions, the droplets may have overall volumes that are less than about 1000 pL, 900 pL, 800 pL, 700 pL, 600 pL, 500 pL, 400 pL, 300 pL, 200 pL, 100 pL, 50 pL, 20 pL, 10 pL, 1 pL, or less. Where co-partitioned with microcapsules, it will be appreciated that the sample fluid volume, e.g., including co-partitioned biological particles and/or beads, within the partitions may be less than about 90% of the above described volumes, less than about 80%, less than about 70%, less than about 60%, less than about 50%, less than about 40%, less than about 30%, less than about 20%, or less than about 10% of the above described volumes.

As is described elsewhere herein, partitioning species may generate a population or plurality of partitions. In such cases, any suitable number of partitions can be generated or otherwise provided. For example, at least about 1,000 partitions, at least about 5,000 partitions, at least about 10,000 partitions, at least about 50,000 partitions, at least about 100,000 partitions, at least about 500,000 partitions, at least about 1,000,000 partitions, at least about 5,000,000 partitions at least about 10,000,000 partitions, at least about 50,000,000 partitions, at least about 100,000,000 partitions, at least about 500,000,000 partitions, at least about 1,000,000,000 partitions, or more partitions can be generated or otherwise provided. Moreover, the plurality of partitions may comprise both unoccupied partitions (e.g., empty partitions) and occupied partitions.

Reagents

In accordance with certain aspects, biological particles may be partitioned along with lysis reagents in order to release the contents of the biological particles within the partition. In such cases, the lysis agents can be contacted with the biological particle suspension concurrently with, or immediately prior to, the introduction of the biological particles into the partitioning junction/droplet generation zone (e.g., junction 210), such as through an additional channel or channels upstream of the channel junction. In accordance with other aspects, additionally or alternatively, biological particles may be partitioned along with other reagents, as will be described further below.

Figure 3:
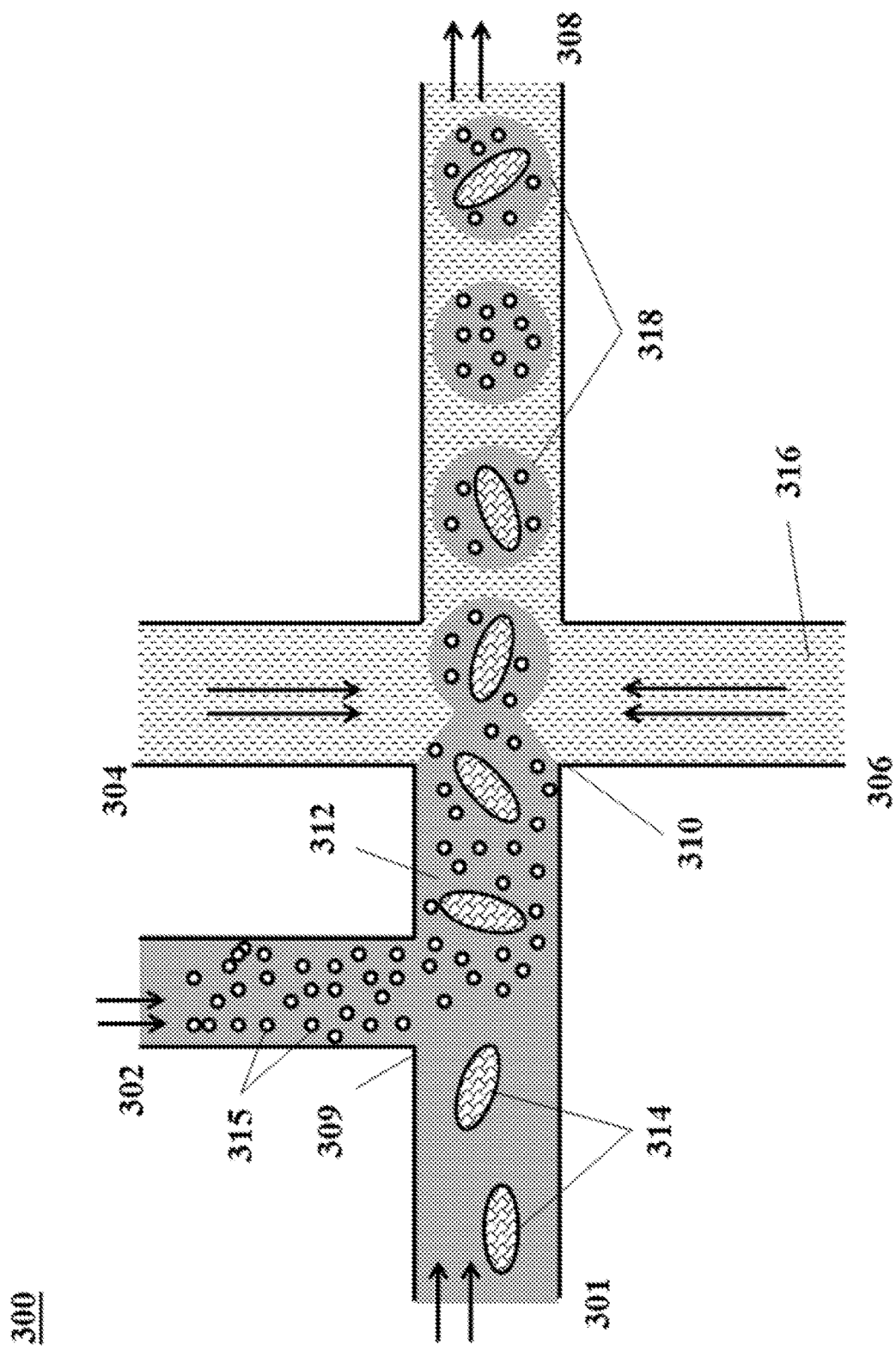
FIG. 3 shows an example of a microfluidic channel structure for co-partitioning biological particles and reagents.

FIG. 3 shows an example of a microfluidic channel structure 300 for co-partitioning biological particles and reagents. The channel structure 300 can include channel segments 301, 302, 304, 306 and 308. Channel segments 301 and 302 communicate at a first channel junction 309. Channel segments 302, 304, 306, and 308 communicate at a second channel junction 310.

In an example operation, the channel segment 301 may transport an aqueous fluid 312 that includes a plurality of biological particles 314 along the channel segment 301 into the second junction 310. As an alternative or in addition to, channel segment 301 may transport beads (e.g., gel beads). The beads may comprise barcode molecules.

For example, the channel segment 301 may be connected to a reservoir comprising an aqueous suspension of biological particles 314. Upstream of, and immediately prior to reaching, the second junction 310, the channel segment 301 may meet the channel segment 302 at the first junction 309. The channel segment 302 may transport a plurality of reagents 315 (e.g., lysis agents) suspended in the aqueous fluid 312 along the channel segment 302 into the first junction 309. For example, the channel segment 302 may be connected to a reservoir comprising the reagents 315. After the first junction 309, the aqueous fluid 312 in the channel segment 301 can carry both the biological particles 314 and the reagents 315 towards the second junction 310. In some instances, the aqueous fluid 312 in the channel segment 301 can include one or more reagents, which can be the same or different reagents as the reagents 315. A second fluid 316 that is immiscible with the aqueous fluid 312 (e.g., oil) can be delivered to the second junction 310 from each of channel segments 304 and 306. Upon meeting of the aqueous fluid 312 from the channel segment 301 and the second fluid 316 from each of channel segments 304 and 306 at the second channel junction 310, the aqueous fluid 312 can be partitioned as discrete droplets 318 in the second fluid 316 and flow away from the second junction 310 along channel segment 308. The channel segment 308 may deliver the discrete droplets 318 to an outlet reservoir fluidly coupled to the channel segment 308, where they may be harvested.

The second fluid 316 can comprise an oil, such as a fluorinated oil, that includes a fluorosurfactant for stabilizing the resulting droplets, for example, inhibiting subsequent coalescence of the resulting droplets 318.

A discrete droplet generated may include an individual biological particle 314 and/or one or more reagents 315. In some instances, a discrete droplet generated may include a barcode carrying bead (not shown), such as via other microfluidics structures described elsewhere herein. In some instances, a discrete droplet may be unoccupied (e.g., no reagents, no biological particles).

Beneficially, when lysis reagents and biological particles are co-partitioned, the lysis reagents can facilitate the release of the contents of the biological particles within the partition. The contents released in a partition may remain discrete from the contents of other partitions.

As will be appreciated, the channel segments described herein may be coupled to any of a variety of different fluid sources or receiving components, including reservoirs, tubing, manifolds, or fluidic components of other systems. As will be appreciated, the microfluidic channel structure 300 may have other geometries. For example, a microfluidic channel structure can have more than two channel junctions. For example, a microfluidic channel structure can have 2, 3, 4, 5 channel segments or more each carrying the same or different types of beads, reagents, and/or biological particles that meet at a channel junction. Fluid flow in each channel segment may be controlled to control the partitioning of the different elements into droplets. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St Louis, MO), as well as other commercially available lysis enzymes. Other lysis agents may additionally or alternatively be co-partitioned with the biological particles to cause the release of the biological particle's contents into the partitions. For example, in some cases, surfactant-based lysis solutions may be used to lyse cells, although these may be less desirable for emulsion based systems where the surfactants can interfere with stable emulsions. In some cases, lysis solutions may include non-ionic surfactants such as, for example, TritonX-100 and Tween 20. In some cases, lysis solutions may include ionic surfactants such as, for example, sarcosyl and sodium dodecyl sulfate (SDS). Electroporation, thermal, acoustic or mechanical cellular disruption may also be used in certain cases, e.g., non-emulsion based partitioning such as encapsulation of biological particles that may be in addition to or in place of droplet partitioning, where any pore size of the encapsulate is sufficiently small to retain nucleic acid fragments of a given size, following cellular disruption.

Alternatively or in addition to the lysis agents co-partitioned with the biological particles described above, other reagents can also be co-partitioned with the biological particles, including, for example, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. In addition, in the case of encapsulated biological particles, the biological particles may be exposed to an appropriate stimulus to release the biological particles or their contents from a co-partitioned microcapsule. For example, in some cases, a chemical stimulus may be co-partitioned along with an encapsulated biological particle to allow for the degradation of the microcapsule and release of the cell or its contents into the larger partition. In some cases, this stimulus may be the same as the stimulus described elsewhere herein for release of nucleic acid molecules (e.g., oligonucleotides) from their respective microcapsule (e.g., bead). In alternative aspects, this may be a different and non-overlapping stimulus, in order to allow an encapsulated biological particle to be released into a partition at a different time from the release of nucleic acid molecules into the same partition.

Additional reagents may also be co-partitioned with the biological particles, such as endonucleases to fragment a biological particle's DNA, DNA polymerase enzymes and dNTPs used to amplify the biological particle's nucleic acid fragments and to attach the barcode molecular tags to the amplified fragments. Other enzymes may be co-partitioned, including without limitation, polymerase, transposase, ligase, proteinase K, DNAse, etc. Additional reagents may also include reverse transcriptase enzymes, including enzymes with terminal transferase activity, primers and oligonucleotides, and switch oligonucleotides (also referred to herein as "switch oligos" or "template switching oligonucleotides") which can be used for template switching. In some cases, template switching can be used to increase the length of a cDNA. In some cases, template switching can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., polyC, to the cDNA in a template independent manner. Switch oligos can include sequences complementary to the additional nucleotides, e.g., polyG. The additional nucleotides (e.g., polyC) on the cDNA can hybridize to the additional nucleotides (e.g., polyG) on the switch oligo, whereby the switch oligo can be used by the reverse transcriptase as template to further extend the cDNA. Template switching oligonucleotides may comprise a hybridization region and a template region. The hybridization region can comprise any sequence capable of hybridizing to the target. In some cases, as previously described, the hybridization region comprises a series of G bases to complement the overhanging C bases at the 3' end of a cDNA molecule. The series of G bases may comprise 1 G base, 2 G bases, 3 G bases, 4 G bases, 5 G bases or more than 5 G bases. The template sequence can comprise any sequence to be incorporated into the cDNA. In some cases, the template region comprises at least 1 (e.g., at least 2, 3, 4, 5 or more) tag sequences and/or functional sequences. Switch oligos may comprise deoxyribonucleic acids; ribonucleic acids; modified nucleic acids including 2-Aminopurine, 2,6-Diaminopurine (2-Amino-dA), inverted dT, 5-Methyl dC, 2'-deoxyInosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' Fluoro bases (e.g., Fluoro C, Fluoro U, Fluoro A, and Fluoro G), or any combination.

In some cases, the length of a switch oligo may be at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides or longer.

In some cases, the length of a switch oligo may be at most about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides.

Once the contents of the cells are released into their respective partitions, the macromolecular components (e.g., macromolecular constituents of biological particles, such as RNA, DNA, or proteins) contained therein may be further processed within the partitions. In accordance with the methods and systems described herein, the macromolecular component contents of individual biological particles can be provided with unique identifiers such that, upon characterization of those macromolecular components they may be attributed as having been derived from the same biological particle or particles. The ability to attribute characteristics to individual biological particles or groups of biological particles is provided by the assignment of unique identifiers specifically to an individual biological particle or groups of biological particles. Unique identifiers, e.g., in the form of nucleic acid barcodes can be assigned or associated with individual biological particles or populations of biological particles, in order to tag or label the biological particle's macromolecular components (and as a result, its characteristics) with the unique identifiers. These unique identifiers can then be used to attribute the biological particle's components and characteristics to an individual biological particle or group of biological particles.

In some aspects, this is performed by co-partitioning the individual biological particle or groups of biological particles with the unique identifiers, such as described above (with reference to FIG. 2). In some aspects, the unique identifiers are provided in the form of nucleic acid molecules (e.g., oligonucleotides) that comprise nucleic acid barcode sequences that may be attached to or otherwise associated with the nucleic acid contents of individual biological particle, or to other components of the biological particle, and particularly to fragments of those nucleic acids. The nucleic acid molecules are partitioned such that as between nucleic acid molecules in a given partition, the nucleic acid barcode sequences contained therein are the same, but as between different partitions, the nucleic acid molecule can, and do have differing barcode sequences, or at least represent a large number of different barcode sequences across all of the partitions in a given analysis. In some aspects, only one nucleic acid barcode sequence can be associated with a given partition, although in some cases, two or more different barcode sequences may be present.

The nucleic acid barcode sequences can include from about 6 to about 20 or more nucleotides within the sequence of the nucleic acid molecules (e.g., oligonucleotides). The nucleic acid barcode sequences can include from about 6 to about 20, 30, 40, 50, 60, 70, 80, 90, 100 or more nucleotides. In some cases, the length of a barcode sequence may be about 6, 7, 8, 9, 10, 11, 12, 13, 14, 15, 16, 17, 18, 19, 20 nucleotides or longer. In some cases, the length of a barcode sequence may be at least about 6, 7, 8, 9, 10, 11, 12, 13, 14, 15, 16, 17, 18, 19, 20 nucleotides or longer. In some cases, the length of a barcode sequence may be at most about 6, 7, 8, 9, 10, 11, 12, 13, 14, 15, 16, 17, 18, 19, 20 nucleotides or shorter. These nucleotides may be completely contiguous, i.e., in a single stretch of adjacent nucleotides, or they may be separated into two or more separate subsequences that are separated by 1 or more nucleotides. In some cases, separated barcode subsequences can be from about 4 to about 16 nucleotides in length. In some cases, the barcode subsequence may be about 4, 5, 6, 7, 8, 9, 10, 11, 12, 13, 14, 15, 16 nucleotides or longer. In some cases, the barcode subsequence may be at least about 4, 5, 6, 7, 8, 9, 10, 11, 12, 13, 14, 15, 16 nucleotides or longer. In some cases, the barcode subsequence may be at most about 4, 5, 6, 7, 8, 9, 10, 11, 12, 13, 14, 15, 16 nucleotides or shorter.

The co-partitioned nucleic acid molecules can also comprise other functional sequences useful in the processing of the nucleic acids from the co-partitioned biological particles. These sequences include, e.g., targeted or random/universal amplification primer sequences for amplifying the genomic DNA from the individual biological particles within the partitions while attaching the associated barcode sequences, sequencing primers or primer recognition sites, hybridization or probing sequences, e.g., for identification of presence of the sequences or for pulling down barcoded nucleic acids, or any of a number of other potential functional sequences. Other mechanisms of co-partitioning oligonucleotides may also be employed, including, e.g., coalescence of two or more droplets, where one droplet contains oligonucleotides, or microdispensing of oligonucleotides into partitions, e.g., droplets within microfluidic systems.

In an example, microcapsules, such as beads, are provided that each include large numbers of the above described barcoded nucleic acid molecules (e.g., barcoded oligonucleotides) releasably attached to the beads, where all of the nucleic acid molecules attached to a particular bead will include the same nucleic acid barcode sequence, but where a large number of diverse barcode sequences are represented across the population of beads used. In some embodiments, hydrogel beads, e.g., comprising polyacrylamide polymer matrices, are used as a solid support and delivery vehicle for the nucleic acid molecules into the partitions, as they are capable of carrying large numbers of nucleic acid molecules, and may be configured to release those nucleic acid molecules upon exposure to a particular stimulus, as described elsewhere herein. In some cases, the population of beads provides a diverse barcode sequence library that includes at least about 1,000 different barcode sequences, at least about 5,000 different barcode sequences, at least about 10,000 different barcode sequences, at least about 50,000 different barcode sequences, at least about 100,000 different barcode sequences, at least about 1,000,000 different barcode sequences, at least about 5,000,000 different barcode sequences, or at least about 10,000,000 different barcode sequences, or more. Additionally, each bead can be provided with large numbers of nucleic acid (e.g., oligonucleotide) molecules attached. In particular, the number of molecules of nucleic acid molecules including the barcode sequence on an individual bead can be at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules, or more. Nucleic acid molecules of a given bead can include identical (or common) barcode sequences, different barcode sequences, or a combination of both. Nucleic acid molecules of a given bead can include multiple sets of nucleic acid molecules. Nucleic acid molecules of a given set can include identical barcode sequences. The identical barcode sequences can be different from barcode sequences of nucleic acid molecules of another set.

Moreover, when the population of beads is partitioned, the resulting population of partitions can also include a diverse barcode library that includes at least about 1,000 different barcode sequences, at least about 5,000 different barcode sequences, at least about 10,000 different barcode sequences, at least at least about 50,000 different barcode sequences, at least about 100,000 different barcode sequences, at least about 1,000,000 different barcode sequences, at least about 5,000,000 different barcode sequences, or at least about 10,000,000 different barcode sequences. Additionally, each partition of the population can include at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules.

In some cases, it may be desirable to incorporate multiple different barcodes within a given partition, either attached to a single or multiple beads within the partition. For example, in some cases, a mixed, but known set of barcode sequences may provide greater assurance of identification in the subsequent processing, e.g., by providing a stronger address or attribution of the barcodes to a given partition, as a duplicate or independent confirmation of the output from a given partition.

The nucleic acid molecules (e.g., oligonucleotides) are releasable from the beads upon the application of a particular stimulus to the beads. In some cases, the stimulus may be a photo-stimulus, e.g., through cleavage of a photo-labile linkage that releases the nucleic acid molecules. In other cases, a thermal stimulus may be used, where elevation of the temperature of the beads environment will result in cleavage of a linkage or other release of the nucleic acid molecules from the beads. In still other cases, a chemical stimulus can be used that cleaves a linkage of the nucleic acid molecules to the beads, or otherwise results in release of the nucleic acid molecules from the beads. In one case, such compositions include the polyacrylamide matrices described above for encapsulation of biological particles, and may be degraded for release of the attached nucleic acid molecules through exposure to a reducing agent, such as DTT.

In some aspects, provided are systems and methods for controlled partitioning. Droplet size may be controlled by adjusting certain geometric features in channel architecture (e.g., microfluidics channel architecture). For example, an expansion angle, width, and/or length of a channel may be adjusted to control droplet size.

Figure 4:
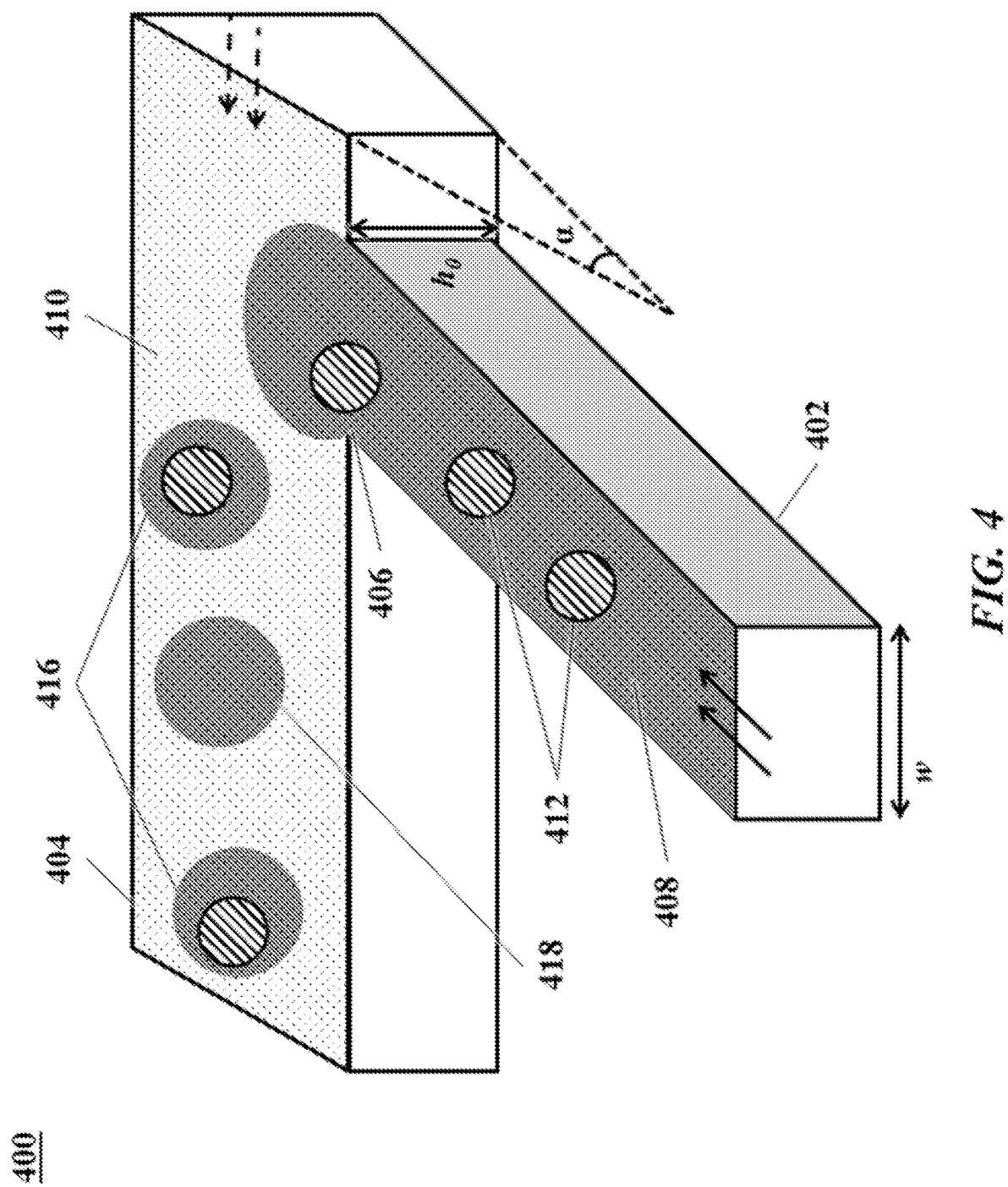
FIG. 4 shows an example of a microfluidic channel structure for the controlled partitioning of beads into discrete droplets.

FIG. 4 shows an example of a microfluidic channel structure for the controlled partitioning of beads into discrete droplets. A channel structure 400 can include a channel segment 402 communicating at a channel junction 406 (or intersection) with a reservoir 404. The reservoir 404 can be a chamber. Any reference to "reservoir," as used herein, can also refer to a "chamber." In operation, an aqueous fluid 408 that includes suspended beads 412 may be transported along the channel segment 402 into the junction 406 to meet a second fluid 410 that is immiscible with the aqueous fluid 408 in the reservoir 404 to create droplets 416, 418 of the aqueous fluid 408 flowing into the reservoir 404. At the junction 406 where the aqueous fluid 408 and the second fluid 410 meet, droplets can form based on factors such as the hydrodynamic forces at the junction 406, flow rates of the two fluids 408, 410, fluid properties, and certain geometric parameters (e.g., w, $h_0$, $\alpha$, etc.) of the channel structure 400. A plurality of droplets can be collected in the reservoir 404 by continuously injecting the aqueous fluid 408 from the channel segment 402 through the junction 406.

A discrete droplet generated may include a bead (e.g., as in occupied droplets 416). Alternatively, a discrete droplet generated may include more than one bead. Alternatively, a discrete droplet generated may not include any beads (e.g., as in unoccupied droplet 418). In some instances, a discrete droplet generated may contain one or more biological particles, as described elsewhere herein. In some instances, a discrete droplet generated may comprise one or more reagents, as described elsewhere herein.

In some instances, the aqueous fluid 408 can have a substantially uniform concentration or frequency of beads 412. The beads 412 can be introduced into the channel segment 402 from a separate channel (not shown in FIG. 4). The frequency of beads 412 in the channel segment 402 may be controlled by controlling the frequency in which the beads 412 are introduced into the channel segment 402 and/or the relative flow rates of the fluids in the channel segment 402 and the separate channel. In some instances, the beads can be introduced into the channel segment 402 from a plurality of different channels, and the frequency controlled accordingly.

In some instances, the aqueous fluid 408 in the channel segment 402 can comprise biological particles (e.g., described with reference to FIGS. 1 and 2). In some instances, the aqueous fluid 408 can have a substantially uniform concentration or frequency of biological particles. As with the beads, the biological particles can be introduced into the channel segment 402 from a separate channel. The frequency or concentration of the biological particles in the aqueous fluid 408 in the channel segment 402 may be controlled by controlling the frequency in which the biological particles are introduced into the channel segment 402 and/or the relative flow rates of the fluids in the channel segment 402 and the separate channel. In some instances, the biological particles can be introduced into the channel segment 402 from a plurality of different channels, and the frequency controlled accordingly. In some instances, a first separate channel can introduce beads and a second separate channel can introduce biological particles into the channel segment 402. The first separate channel introducing the beads may be upstream or downstream of the second separate channel introducing the biological particles.

The second fluid 410 can comprise an oil, such as a fluorinated oil, that includes a fluorosurfactant for stabilizing the resulting droplets, for example, inhibiting subsequent coalescence of the resulting droplets.

In some instances, the second fluid 410 may not be subjected to and/or directed to any flow in or out of the reservoir 404. For example, the second fluid 410 may be substantially stationary in the reservoir 404. In some instances, the second fluid 410 may be subjected to flow within the reservoir 404, but not in or out of the reservoir 404, such as via application of pressure to the reservoir 404 and/or as affected by the incoming flow of the aqueous fluid 408 at the junction 406. Alternatively, the second fluid 410 may be subjected and/or directed to flow in or out of the reservoir 404. For example, the reservoir 404 can be a channel directing the second fluid 410 from upstream to downstream, transporting the generated droplets.

The channel structure 400 at or near the junction 406 may have certain geometric features that at least partly determine the sizes of the droplets formed by the channel structure 400. The channel segment 402 can have a height, $h_0$ and width, w, at or near the junction 406. By way of example, the channel segment 402 can comprise a rectangular cross-section that leads to a reservoir 404 having a wider cross-section (such as in width or diameter). Alternatively, the cross-section of the channel segment 402 can be other shapes, such as a circular shape, trapezoidal shape, polygonal shape, or any other shapes. The top and bottom walls of the reservoir 404 at or near the junction 406 can be inclined at an expansion angle, a. The expansion angle, a, allows the tongue (portion of the aqueous fluid 408 leaving channel segment 402 at junction 406 and entering the reservoir 404 before droplet formation) to increase in depth and facilitate decrease in curvature of the intermediately formed droplet. Droplet size may decrease with increasing expansion angle. The resulting droplet radius, $R_d$, may be predicted by the following equation for the aforementioned geometric parameters of $h_0$, w, and $\alpha$:

$$R_d \approx 0.44\left(1 + 2.2\sqrt{\tan\alpha}\,\frac{w}{h_0}\right)\frac{h_0}{\sqrt{\tan\alpha}}$$

By way of example, for a channel structure with w=21 μm, h=21 μm, and $\alpha=3°$, the predicted droplet size is 121 μm. In another example, for a channel structure with w=25 μm, h=25 μm, and $\alpha=5°$, the predicted droplet size is 123 μm. In another example, for a channel structure with w=28 μm, h=28 μm, and $\alpha=7°$, the predicted droplet size is 124 μm.

In some instances, the expansion angle, $\alpha$, may be between a range of from about 0.5° to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, 0.1°, 0.01°, or less. In some instances, the width, w, can be between a range of from about 100 micrometers (μm) to about 500 μm. In some instances, the width, w, can be between a range of from about 10 μm to about 200 μm. Alternatively, the width can be less than about 10 μm. Alternatively, the width can be greater than about 500 μm. In some instances, the flow rate of the aqueous fluid 408 entering the junction 406 can be between about 0.04 microliters (μL)/minute (min) and about 40 μL/min. In some instances, the flow rate of the aqueous fluid 408 entering the junction 406 can be between about 0.01 microliters (μL)/minute (min) and about 100 μL/min. Alternatively, the flow rate of the aqueous fluid 408 entering the junction 406 can be less than about 0.01 µL/min. Alternatively, the flow rate of the aqueous fluid 408 entering the junction 406 can be greater than about 40 µL/min, such as 45 µL/min, 50 µL/min, 55 µL/min, 60 µL/min, 65 µL/min, 70 µL/min, 75 µL/min, 80 µL/min, 85 µL/min, 90 µL/min, 95 µL/min, 100 µL/min, 110 µL/min, 120 µL/min, 130 µL/min, 140 µL/min, 150 µL/min, or greater. At lower flow rates, such as flow rates of about less than or equal to 10 microliters/minute, the droplet radius may not be dependent on the flow rate of the aqueous fluid 408 entering the junction 406.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

The throughput of droplet generation can be increased by increasing the points of generation, such as increasing the number of junctions (e.g., junction 406) between aqueous fluid 408 channel segments (e.g., channel segment 402) and the reservoir 404. Alternatively or in addition, the throughput of droplet generation can be increased by increasing the flow rate of the aqueous fluid 408 in the channel segment 402.

Figure 5:
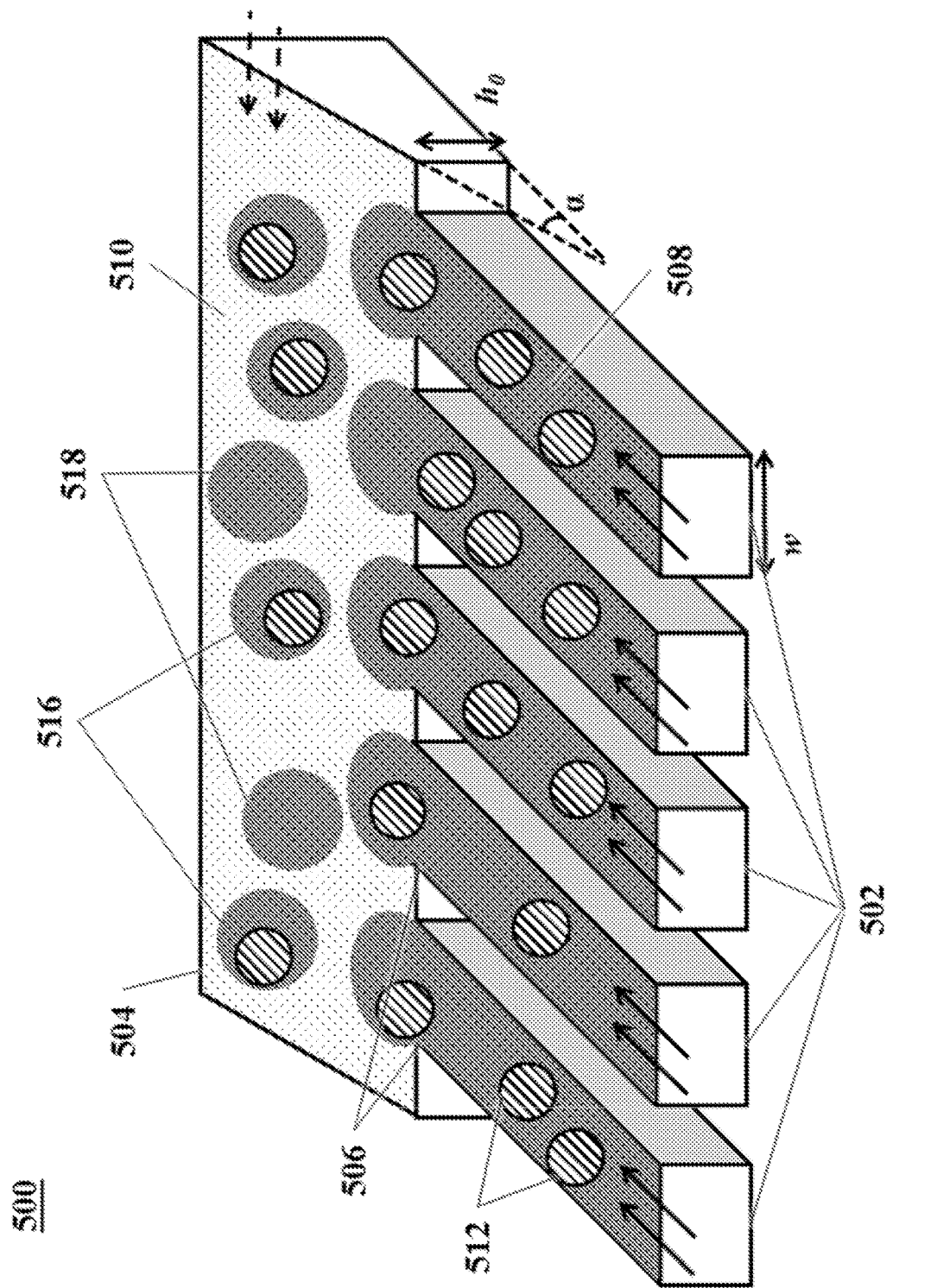
FIG. 5 shows an example of a microfluidic channel structure for increased droplet generation throughput.

FIG. 5 shows an example of a microfluidic channel structure for increased droplet generation throughput. A microfluidic channel structure 500 can comprise a plurality of channel segments 502 and a reservoir 504. Each of the plurality of channel segments 502 may be in fluid communication with the reservoir 504. The channel structure 500 can comprise a plurality of channel junctions 506 between the plurality of channel segments 502 and the reservoir 504. Each channel junction can be a point of droplet generation. The channel segment 402 from the channel structure 400 in FIG. 4 and any description to the components thereof may correspond to a given channel segment of the plurality of channel segments 502 in channel structure 500 and any description to the corresponding components thereof. The reservoir 404 from the channel structure 400 and any description to the components thereof may correspond to the reservoir 504 from the channel structure 500 and any description to the corresponding components thereof.

Each channel segment of the plurality of channel segments 502 may comprise an aqueous fluid 508 that includes suspended beads 512. The reservoir 504 may comprise a second fluid 510 that is immiscible with the aqueous fluid 508. In some instances, the second fluid 510 may not be subjected to and/or directed to any flow in or out of the reservoir 504. For example, the second fluid 510 may be substantially stationary in the reservoir 504. In some instances, the second fluid 510 may be subjected to flow within the reservoir 504, but not in or out of the reservoir 504, such as via application of pressure to the reservoir 504 and/or as affected by the incoming flow of the aqueous fluid 508 at the junctions. Alternatively, the second fluid 510 may be subjected and/or directed to flow in or out of the reservoir 504. For example, the reservoir 504 can be a channel directing the second fluid 510 from upstream to downstream, transporting the generated droplets.

In operation, the aqueous fluid 508 that includes suspended beads 512 may be transported along the plurality of channel segments 502 into the plurality of junctions 506 to meet the second fluid 510 in the reservoir 504 to create droplets 516, 518. A droplet may form from each channel segment at each corresponding junction with the reservoir 504. At the junction where the aqueous fluid 508 and the second fluid 510 meet, droplets can form based on factors such as the hydrodynamic forces at the junction, flow rates of the two fluids 508, 510, fluid properties, and certain geometric parameters (e.g., w, $h_0$, $\alpha$, etc.) of the channel structure 500, as described elsewhere herein. A plurality of droplets can be collected in the reservoir 504 by continuously injecting the aqueous fluid 508 from the plurality of channel segments 502 through the plurality of junctions 506. Throughput may significantly increase with the parallel channel configuration of channel structure 500. For example, a channel structure having five inlet channel segments comprising the aqueous fluid 508 may generate droplets five times as frequently than a channel structure having one inlet channel segment, provided that the fluid flow rate in the channel segments are substantially the same. The fluid flow rate in the different inlet channel segments may or may not be substantially the same. A channel structure may have as many parallel channel segments as is practical and allowed for the size of the reservoir. For example, the channel structure may have at least about 2, 3, 4, 5, 6, 7, 8, 9, 10, 20, 30, 40, 50, 60, 70, 80, 90, 100, 150, 500, 250, 300, 350, 400, 450, 500, 600, 700, 800, 900, 1000, 1500, 5000 or more parallel or substantially parallel channel segments.

The geometric parameters, w, $h_0$, and $\alpha$, may or may not be uniform for each of the channel segments in the plurality of channel segments 502. For example, each channel segment may have the same or different widths at or near its respective channel junction with the reservoir 504. For example, each channel segment may have the same or different height at or near its respective channel junction with the reservoir 504. In another example, the reservoir 504 may have the same or different expansion angle at the different channel junctions with the plurality of channel segments 502. When the geometric parameters are uniform, beneficially, droplet size may also be controlled to be uniform even with the increased throughput. In some instances, when it is desirable to have a different distribution of droplet sizes, the geometric parameters for the plurality of channel segments 502 may be varied accordingly.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

Figure 6:
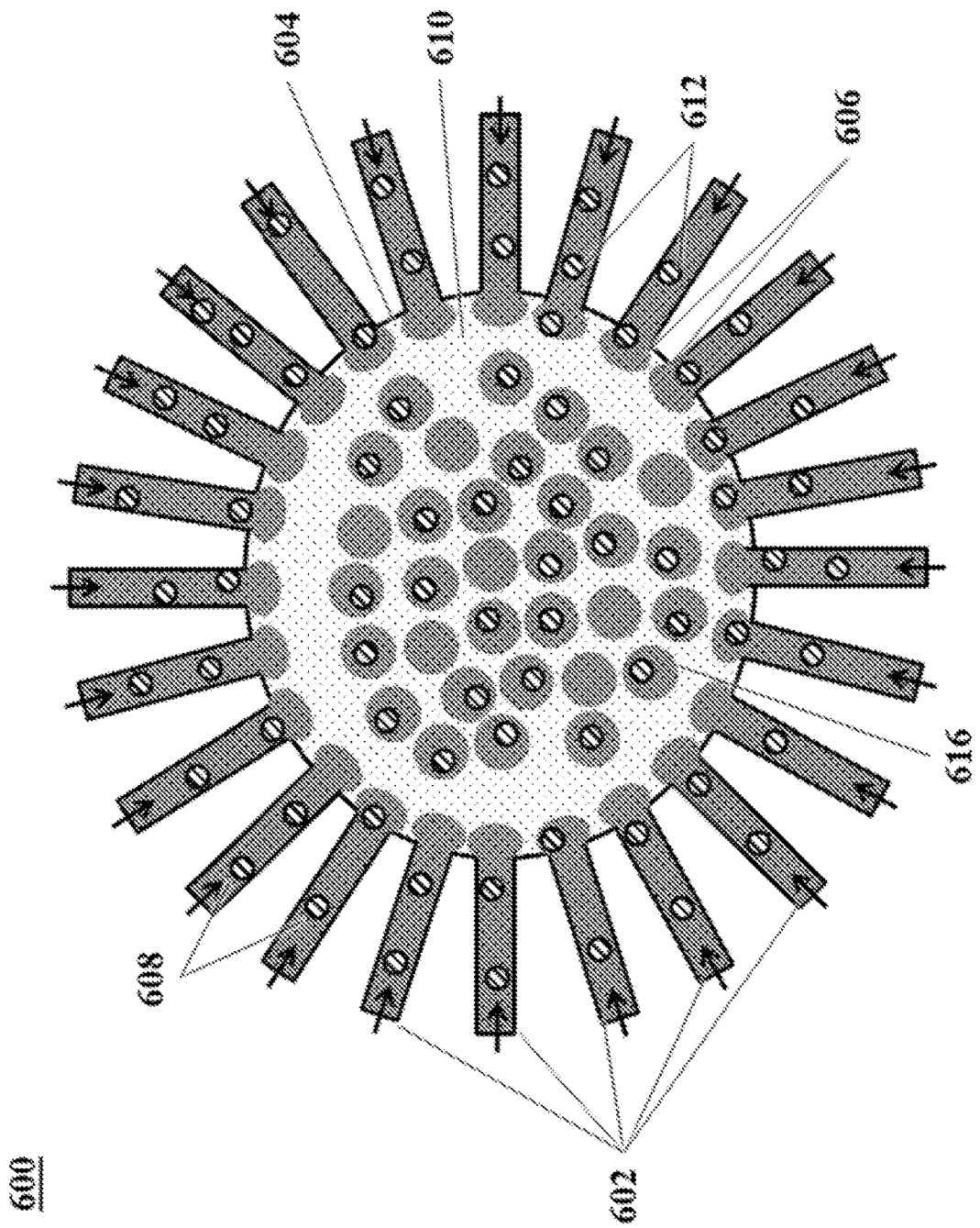
FIG. 6 shows another example of a microfluidic channel structure for increased droplet generation throughput.

FIG. 6 shows another example of a microfluidic channel structure for increased droplet generation throughput. A microfluidic channel structure 600 can comprise a plurality of channel segments 602 arranged generally circularly around the perimeter of a reservoir 604. Each of the plurality of channel segments 602 may be in fluid communication with the reservoir 604. The channel structure 600 can comprise a plurality of channel junctions 606 between the plurality of channel segments 602 and the reservoir 604. Each channel junction can be a point of droplet generation. The channel segment 402 from the channel structure 400 in FIG. 4 and any description to the components thereof may correspond to a given channel segment of the plurality of channel segments 602 in channel structure 600 and any description to the corresponding components thereof. The reservoir 404 from the channel structure 400 and any description to the components thereof may correspond to the reservoir 604 from the channel structure 600 and any description to the corresponding components thereof.

Each channel segment of the plurality of channel segments 602 may comprise an aqueous fluid 608 that includes suspended beads 612. The reservoir 604 may comprise a second fluid 610 that is immiscible with the aqueous fluid 608. In some instances, the second fluid 610 may not be subjected to and/or directed to any flow in or out of the reservoir 604. For example, the second fluid 610 may be substantially stationary in the reservoir 604. In some instances, the second fluid 610 may be subjected to flow within the reservoir 604, but not in or out of the reservoir 604, such as via application of pressure to the reservoir 604 and/or as affected by the incoming flow of the aqueous fluid 608 at the junctions. Alternatively, the second fluid 610 may be subjected and/or directed to flow in or out of the reservoir 604. For example, the reservoir 604 can be a channel directing the second fluid 610 from upstream to downstream, transporting the generated droplets.

In operation, the aqueous fluid 608 that includes suspended beads 612 may be transported along the plurality of channel segments 602 into the plurality of junctions 606 to meet the second fluid 610 in the reservoir 604 to create a plurality of droplets 616. A droplet may form from each channel segment at each corresponding junction with the reservoir 604. At the junction where the aqueous fluid 608 and the second fluid 610 meet, droplets can form based on factors such as the hydrodynamic forces at the junction, flow rates of the two fluids 608, 610, fluid properties, and certain geometric parameters (e.g., widths and heights of the channel segments 602, expansion angle of the reservoir 604, etc.) of the channel structure 600, as described elsewhere herein. A plurality of droplets can be collected in the reservoir 604 by continuously injecting the aqueous fluid 608 from the plurality of channel segments 602 through the plurality of junctions 606. Throughput may significantly increase with the substantially parallel channel configuration of the channel structure 600. A channel structure may have as many substantially parallel channel segments as is practical and allowed for by the size of the reservoir. For example, the channel structure may have at least about 2, 3, 4, 5, 6, 7, 8, 9, 10, 20, 30, 40, 50, 60, 70, 80, 90, 100, 150, 200, 250, 300, 350, 400, 450, 500, 600, 700, 800, 900, 1000, 1500, 5000 or more parallel or substantially parallel channel segments. The plurality of channel segments may be substantially evenly spaced apart, for example, around an edge or perimeter of the reservoir. Alternatively, the spacing of the plurality of channel segments may be uneven.

The reservoir 604 may have an expansion angle, a (not shown in FIG. 6) at or near each channel junction. Each channel segment of the plurality of channel segments 602 may have a width, w, and a height, $h_0$, at or near the channel junction. The geometric parameters, w, $h_0$, and α, may or may not be uniform for each of the channel segments in the plurality of channel segments 602. For example, each channel segment may have the same or different widths at or near its respective channel junction with the reservoir 604. For example, each channel segment may have the same or different height at or near its respective channel junction with the reservoir 604.

The reservoir 604 may have the same or different expansion angle at the different channel junctions with the plurality of channel segments 602. For example, a circular reservoir (as shown in FIG. 6) may have a conical, dome-like, or hemispherical ceiling (e.g., top wall) to provide the same or substantially same expansion angle for each channel segments 602 at or near the plurality of channel junctions 606. When the geometric parameters are uniform, beneficially, resulting droplet size may be controlled to be uniform even with the increased throughput. In some instances, when it is desirable to have a different distribution of droplet sizes, the geometric parameters for the plurality of channel segments 602 may be varied accordingly.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size. The beads and/or biological particle injected into the droplets may or may not have uniform size.

Figure 7A:
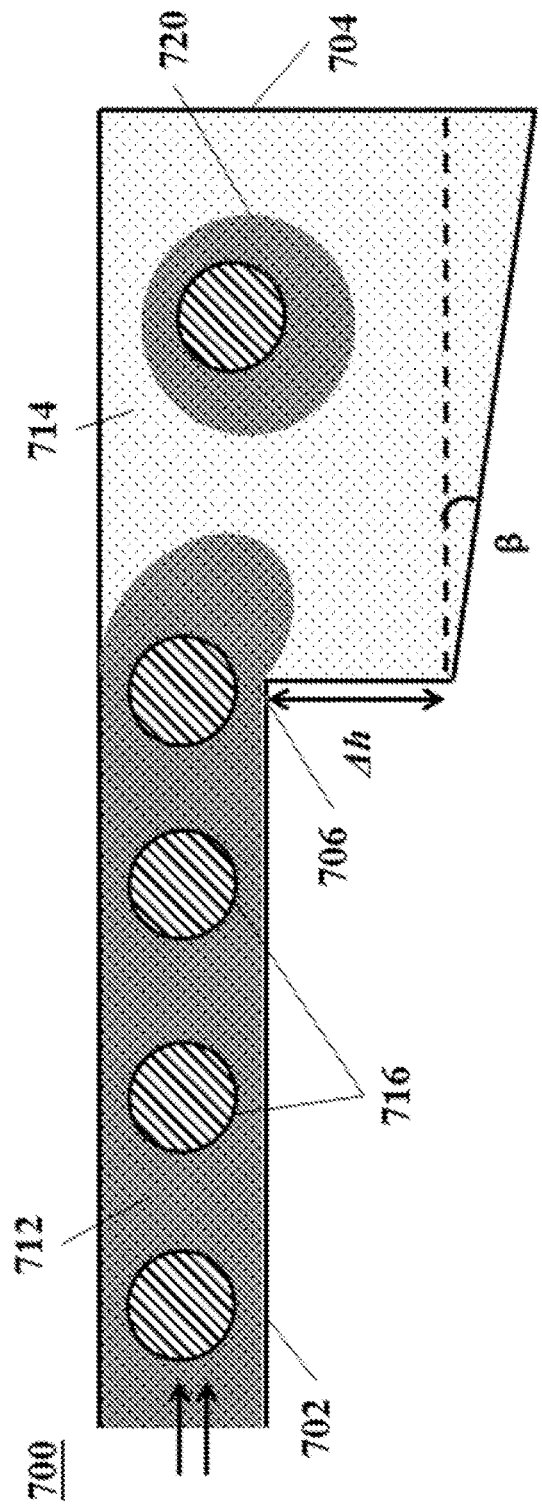
FIG. 7A shows a cross-section view of another example of a microfluidic channel structure with a geometric feature for controlled partitioning.
Figure 7B:
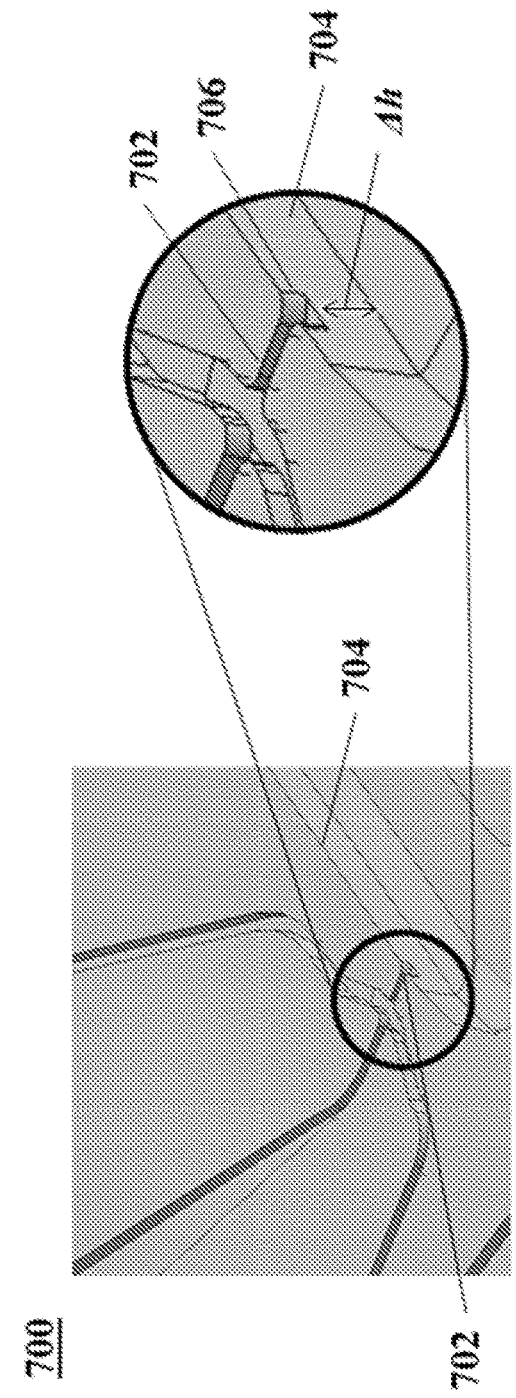
FIG. 7B shows a perspective view of the channel structure of FIG. 7A.

FIG. 7A shows a cross-section view of another example of a microfluidic channel structure with a geometric feature for controlled partitioning. A channel structure 700 can include a channel segment 702 communicating at a channel junction 706 (or intersection) with a reservoir 704. In some instances, the channel structure 700 and one or more of its components can correspond to the channel structure 100 and one or more of its components. FIG. 7B shows a perspective view of the channel structure 700 of FIG. 7A.

An aqueous fluid 712 comprising a plurality of particles 716 may be transported along the channel segment 702 into the junction 706 to meet a second fluid 714 (e.g., oil, etc.) that is immiscible with the aqueous fluid 712 in the reservoir 704 to create droplets 720 of the aqueous fluid 712 flowing into the reservoir 704. At the junction 706 where the aqueous fluid 712 and the second fluid 714 meet, droplets can form based on factors such as the hydrodynamic forces at the junction 706, relative flow rates of the two fluids 712, 714, fluid properties, and certain geometric parameters (e.g., Δh, etc.) of the channel structure 700. A plurality of droplets can be collected in the reservoir 704 by continuously injecting the aqueous fluid 712 from the channel segment 702 at the junction 706.

A discrete droplet generated may comprise one or more particles of the plurality of particles 716. As described elsewhere herein, a particle may be any particle, such as a bead, cell bead, gel bead, biological particle, macromolecular constituents of biological particle, or other particles. Alternatively, a discrete droplet generated may not include any particles.

In some instances, the aqueous fluid 712 can have a substantially uniform concentration or frequency of particles 716. As described elsewhere herein (e.g., with reference to FIG. 4), the particles 716 (e.g., beads) can be introduced into the channel segment 702 from a separate channel (not shown in FIG. 7). The frequency of particles 716 in the channel segment 702 may be controlled by controlling the frequency in which the particles 716 are introduced into the channel segment 702 and/or the relative flow rates of the fluids in the channel segment 702 and the separate channel. In some instances, the particles 716 can be introduced into the channel segment 702 from a plurality of different channels, and the frequency controlled accordingly. In some instances, different particles may be introduced via separate channels. For example, a first separate channel can introduce beads and a second separate channel can introduce biological particles into the channel segment 702. The first separate channel introducing the beads may be upstream or downstream of the second separate channel introducing the biological particles.

In some instances, the second fluid 714 may not be subjected to and/or directed to any flow in or out of the reservoir 704. For example, the second fluid 714 may be substantially stationary in the reservoir 704. In some instances, the second fluid 714 may be subjected to flow within the reservoir 704, but not in or out of the reservoir 704, such as via application of pressure to the reservoir 704 and/or as affected by the incoming flow of the aqueous fluid 712 at the junction 706. Alternatively, the second fluid 714 may be subjected and/or directed to flow in or out of the reservoir 704. For example, the reservoir 704 can be a channel directing the second fluid 714 from upstream to downstream, transporting the generated droplets.

The channel structure 700 at or near the junction 706 may have certain geometric features that at least partly determine the sizes and/or shapes of the droplets formed by the channel structure 700. The channel segment 702 can have a first cross-section height, $h_1$, and the reservoir 704 can have a second cross-section height, $h_2$. The first cross-section height, $h_1$, and the second cross-section height, $h_2$, may be different, such that at the junction 706, there is a height difference of $\Delta h$. The second cross-section height, $h_2$, may be greater than the first cross-section height, $h_1$. In some instances, the reservoir may thereafter gradually increase in cross-section height, for example, the more distant it is from the junction 706. In some instances, the cross-section height of the reservoir may increase in accordance with expansion angle, $\beta$, at or near the junction 706. The height difference, $\Delta h$, and/or expansion angle, $\beta$, can allow the tongue (portion of the aqueous fluid 712 leaving channel segment 702 at junction 706 and entering the reservoir 704 before droplet formation) to increase in depth and facilitate decrease in curvature of the intermediately formed droplet. For example, droplet size may decrease with increasing height difference and/or increasing expansion angle.

The height difference, $\Delta h$, can be at least about 1 μm. Alternatively, the height difference can be at least about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500 μm or more. Alternatively, the height difference can be at most about 500, 400, 300, 200, 100, 90, 80, 70, 60, 50, 45, 40, 35, 30, 25, 20, 19, 18, 17, 16, 15, 14, 13, 12, 11, 10, 9, 8, 7, 6, 5, 4, 3, 2, 1 μm or less. In some instances, the expansion angle, $\beta$, may be between a range of from about 0.5° to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, 0.1°, 0.01°, or less.

In some instances, the flow rate of the aqueous fluid 712 entering the junction 706 can be between about 0.04 microliters (μL)/minute (min) and about 40 μL/min. In some instances, the flow rate of the aqueous fluid 712 entering the junction 706 can be between about 0.01 microliters (μL)/minute (min) and about 100 μL/min. Alternatively, the flow rate of the aqueous fluid 712 entering the junction 706 can be less than about 0.01 μL/min. Alternatively, the flow rate of the aqueous fluid 712 entering the junction 706 can be greater than about 40 μL/min, such as 45 μL/min, 50 μL/min, 55 μL/min, 60 μL/min, 65 μL/min, 70 μL/min, 75 μL/min, 80 μL/min, 85 μL/min, 90 μL/min, 95 μL/min, 100 μL/min, 110 μL/min, 120 μL/min, 130 μL/min, 140 μL/min, 150 μL/min, or greater. At lower flow rates, such as flow rates of about less than or equal to 10 microliters/minute, the droplet radius may not be dependent on the flow rate of the aqueous fluid 712 entering the junction 706. The second fluid 714 may be stationary, or substantially stationary, in the reservoir 704. Alternatively, the second fluid 714 may be flowing, such as at the above flow rates described for the aqueous fluid 712.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

While FIGS. 7A and 7B illustrate the height difference, $\Delta h$, being abrupt at the junction 706 (e.g., a step increase), the height difference may increase gradually (e.g., from about 0 μm to a maximum height difference). Alternatively, the height difference may decrease gradually (e.g., taper) from a maximum height difference. A gradual increase or decrease in height difference, as used herein, may refer to a continuous incremental increase or decrease in height difference, wherein an angle between any one differential segment of a height profile and an immediately adjacent differential segment of the height profile is greater than 90°. For example, at the junction 706, a bottom wall of the channel and a bottom wall of the reservoir can meet at an angle greater than 90°. Alternatively or in addition, a top wall (e.g., ceiling) of the channel and a top wall (e.g., ceiling) of the reservoir can meet an angle greater than 90°. A gradual increase or decrease may be linear or non-linear (e.g., exponential, sinusoidal, etc.). Alternatively or in addition, the height difference may variably increase and/or decrease linearly or non-linearly. While FIGS. 7A and 7B illustrate the expanding reservoir cross-section height as linear (e.g., constant expansion angle, $\beta$), the cross-section height may expand non-linearly. For example, the reservoir may be defined at least partially by a dome-like (e.g., hemispherical) shape having variable expansion angles. The cross-section height may expand in any shape.

The channel networks, e.g., as described above or elsewhere herein, can be fluidly coupled to appropriate fluidic components. For example, the inlet channel segments are fluidly coupled to appropriate sources of the materials they are to deliver to a channel junction. These sources may include any of a variety of different fluidic components, from simple reservoirs defined in or connected to a body structure of a microfluidic device, to fluid conduits that deliver fluids from off-device sources, manifolds, fluid flow units (e.g., actuators, pumps, compressors) or the like. Likewise, the outlet channel segment (e.g., channel segment 208, reservoir 604, etc.) may be fluidly coupled to a receiving vessel or conduit for the partitioned cells for subsequent processing. Again, this may be a reservoir defined in the body of a microfluidic device, or it may be a fluidic conduit for delivering the partitioned cells to a subsequent process operation, instrument or component.

The methods and systems described herein may be used to greatly increase the efficiency of single cell applications and/or other applications receiving droplet-based input. For example, following the sorting of occupied cells and/or appropriately-sized cells, subsequent operations that can be performed can include generation of amplification products, purification (e.g., via solid phase reversible immobilization (SPRI)), further processing (e.g., shearing, ligation of functional sequences, and subsequent amplification (e.g., via PCR)). These operations may occur in bulk (e.g., outside the partition). In the case where a partition is a droplet in an emulsion, the emulsion can be broken and the contents of the droplet pooled for additional operations. Additional reagents that may be co-partitioned along with the barcode bearing bead may include oligonucleotides to block ribosomal RNA (rRNA) and nucleases to digest genomic DNA from cells. Alternatively, rRNA removal agents may be applied during additional processing operations. The configuration of the constructs generated by such a method can help minimize (or avoid) sequencing of the poly-T sequence during sequencing and/or sequence the 5' end of a polynucleotide sequence. The amplification products, for example, first amplification products and/or second amplification products, may be subject to sequencing for sequence analysis. In some cases, amplification may be performed using the Partial Hairpin Amplification for Sequencing (PHASE) method.

A variety of applications require the evaluation of the presence and quantification of different biological particle or organism types within a population of biological particles, including, for example, microbiome analysis and characterization, environmental testing, food safety testing, epidemiological analysis, e.g., in tracing contamination or the like.

Computer Systems

Figure 11:
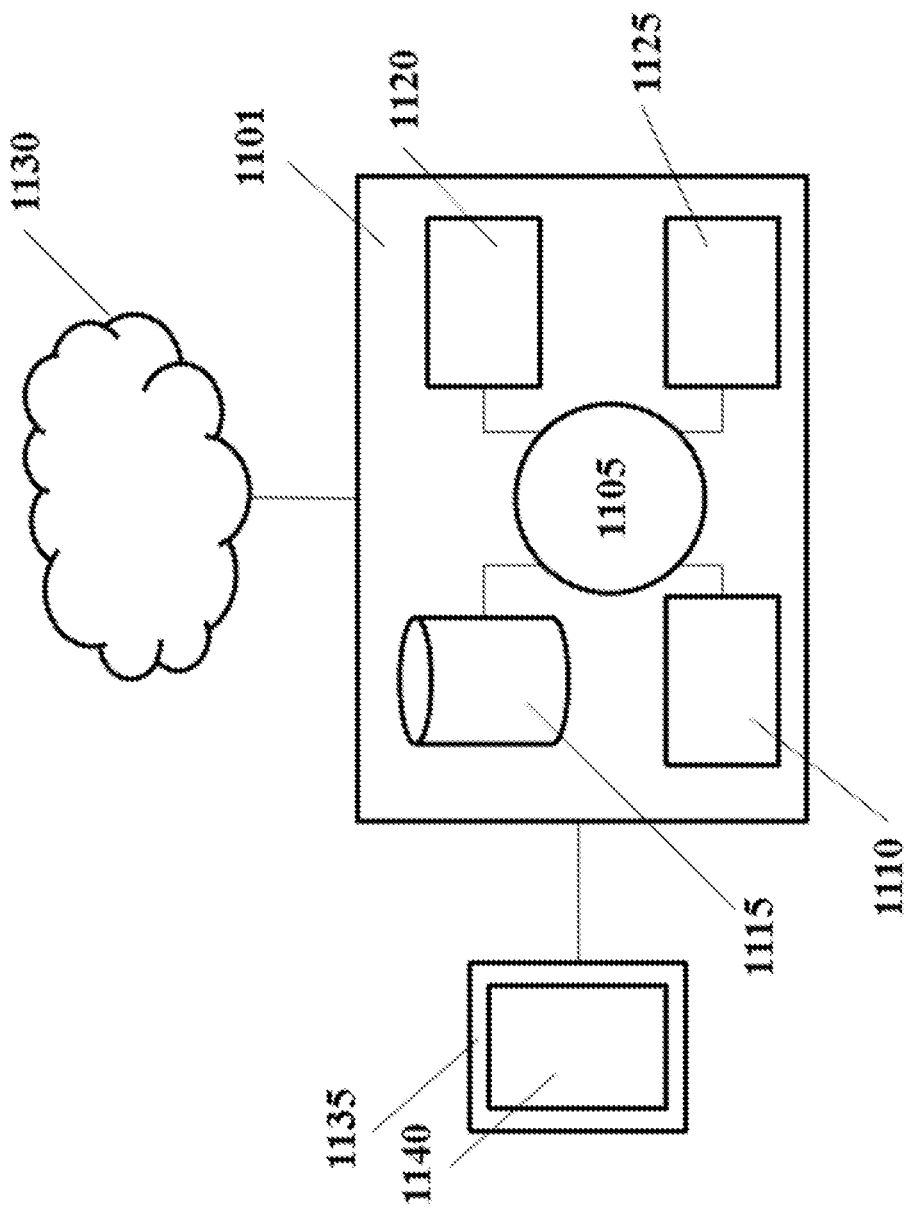
FIG. 11 shows a computer system that is programmed or otherwise configured to implement methods provided herein.

The present disclosure provides computer systems that are programmed to implement methods of the disclosure. FIG. 11 shows a computer system 1101 that is programmed or otherwise configured to (i) control a microfluidics system (e.g., fluid flow), (ii) sort occupied droplets from unoccupied droplets, (iii) polymerize droplets, (iv) perform sequencing applications, or (v) generate and maintain a library of barcode molecules. The computer system 1101 can regulate various aspects of the present disclosure, such as, for example, fluid flow rates in one or more channels in a microfluidic structure, polymerization application units, etc. The computer system 1101 can be an electronic device of a user or a computer system that is remotely located with respect to the electronic device. The electronic device can be a mobile electronic device.

The computer system 1101 includes a central processing unit (CPU, also "processor" and "computer processor" herein) 1105, which can be a single core or multi core processor, or a plurality of processors for parallel processing. The computer system 1201 also includes memory or memory location 1110 (e.g., random-access memory, read-only memory, flash memory), electronic storage unit 1115 (e.g., hard disk), communication interface 1120 (e.g., network adapter) for communicating with one or more other systems, and peripheral devices 1225, such as cache, other memory, data storage and/or electronic display adapters. The memory 1110, storage unit 1115, interface 1120 and peripheral devices 1125 are in communication with the CPU 1105 through a communication bus (solid lines), such as a motherboard. The storage unit 1115 can be a data storage unit (or data repository) for storing data. The computer system 1101 can be operatively coupled to a computer network ("network") 1130 with the aid of the communication interface 1120. The network 1130 can be the Internet, an internet and/or extranet, or an intranet and/or extranet that is in communication with the Internet. The network 1130 in some cases is a telecommunication and/or data network. The network 1130 can include one or more computer servers, which can enable distributed computing, such as cloud computing. The network 1130, in some cases with the aid of the computer system 1101, can implement a peer-to-peer network, which may enable devices coupled to the computer system 1101 to behave as a client or a server.

The CPU 1105 can execute a sequence of machine-readable instructions, which can be embodied in a program or software. The instructions may be stored in a memory location, such as the memory 1110. The instructions can be directed to the CPU 1105, which can subsequently program or otherwise configure the CPU 1105 to implement methods of the present disclosure. Examples of operations performed by the CPU 1105 can include fetch, decode, execute, and writeback.

The CPU 1105 can be part of a circuit, such as an integrated circuit. One or more other components of the system 1101 can be included in the circuit. In some cases, the circuit is an application specific integrated circuit (ASIC).

The storage unit 1115 can store files, such as drivers, libraries and saved programs. The storage unit 1115 can store user data, e.g., user preferences and user programs. The computer system 1101 in some cases can include one or more additional data storage units that are external to the computer system 1101, such as located on a remote server that is in communication with the computer system 1101 through an intranet or the Internet.

The computer system 1101 can communicate with one or more remote computer systems through the network 1130. For instance, the computer system 1101 can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1101 via the network 1130.

Methods as described herein can be implemented by way of machine (e.g., computer processor) executable code stored on an electronic storage location of the computer system 1101, such as, for example, on the memory 1110 or electronic storage unit 1115. The machine executable or machine readable code can be provided in the form of software. During use, the code can be executed by the processor 1105. In some cases, the code can be retrieved from the storage unit 1115 and stored on the memory 1110 for ready access by the processor 1105. In some situations, the electronic storage unit 1115 can be precluded, and machine-executable instructions are stored on memory 1110.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1101, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1101 can include or be in communication with an electronic display 1135 that comprises a user interface (UI) 1140 for providing, for example, results of sequencing analysis, etc. Examples of UIs include, without limitation, a graphical user interface (GUI) and web-based user interface.

Methods and systems of the present disclosure can be implemented by way of one or more algorithms. An algorithm can be implemented by way of software upon execution by the central processing unit 1105. The algorithm can, for example, perform sequencing, etc.

Devices, systems, compositions and methods of the present disclosure may be used for various applications, such as, for example, processing a single analyte (e.g., RNA, DNA, or protein) or multiple analytes (e.g., DNA and RNA, DNA and protein, RNA and protein, or RNA, DNA and protein) from a single cell. For example, a biological particle (e.g., a cell or cell bead) is partitioned in a partition (e.g., droplet), and multiple analytes from the biological particle are processed for subsequent processing. The multiple analytes may be from the single cell. This may enable, for example, simultaneous proteomic, transcriptomic and genomic analysis of the cell.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A mixture, comprising:
   a nucleic acid comprising: (i) a first moiety, (ii) a nucleic acid sequence, and (ii) a poly-thymine (poly(T)) sequence, a poly-guanine (poly(G)) sequence, or an N-mer sequence;
   a nucleic acid barcode comprising a first strand and a second strand, wherein said first strand comprises a second moiety and a barcode sequence, wherein said second strand comprises (1) a first sequence complementary to said barcode sequence and (2) an overhang comprising a second sequence complementary to said nucleic acid sequence; and
   reagents configured to non-enzymatically ligate said first moiety to said second moiety.

2. The mixture of claim 1, further comprising a nucleic acid analyte, wherein said nucleic acid analyte is selected from the group consisting of a messenger ribonucleic acid (mRNA) molecule, a deoxyribonucleic acid (DNA) molecule, and an oligonucleotide attached to a labeling agent.

3. The mixture of claim 2, wherein said nucleic acid analyte is said oligonucleotide attached to said labeling agent, and wherein said labeling agent is selected from the group consisting of a protein, antibody, and a lipid molecule.

4. The mixture of claim 2, wherein said poly(T) sequence, said poly(G) sequence, or said N-mer sequence is part of a single stranded molecule configured to hybridize to a single-stranded end of a nucleic acid molecule of said nucleic acid analyte.

5. The mixture of claim 1, wherein said first moiety and said second moiety are configured to generate a chemical bond selected from the group consisting of a triazole bond, a phosphorothioate bond, and an amide bond, when ligated together.

6. The mixture of claim 1, further comprising a support, wherein said nucleic acid barcode is coupled to said support.

7. The mixture of claim 6, wherein said support comprises a plurality of nucleic acid barcodes comprising said nucleic acid barcode.

8. The mixture of claim 6, wherein said nucleic acid barcode is releasably coupled to said support.

9. The mixture of claim 8, wherein said nucleic acid barcode is releasably coupled to said support by a labile bond, and wherein said labile bond is selected from the group consisting of a thermally labile bond, a chemically labile bond, and a photolabile bond.

10. The mixture of claim 6, wherein said support is a bead.

11. The mixture of claim 10, wherein said bead is a gel bead.

12. The mixture of claim 11, wherein said gel bead is configured to degrade upon application of a stimulus.

13. The mixture of claim 12, wherein said stimulus is selected from the group consisting of a thermal stimulus, a photo stimulus, a mechanical stimulus, a radiation stimulus, and a biological stimulus.

14. The mixture of claim 12, further comprising a chemical stimulus.

15. The mixture of claim 1, wherein said nucleic acid comprises said N-mer sequence located at a 3' end of said nucleic acid.

16. The mixture of claim 1, wherein said nucleic acid comprises said poly(G) sequence located at a 3' end of said nucleic acid.

17. The mixture of claim 1, wherein said nucleic acid is configured to be non-enzymatically ligated to a 5' region of said first strand of said nucleic acid barcode.

18. The mixture of claim 1, wherein said nucleic acid is configured to be non-enzymatically ligated to a 3' region of said first strand of said nucleic acid barcode.

19. The mixture of claim 1, wherein said nucleic acid comprises said poly(T) sequence located at a 3' end of said nucleic acid.

20. The mixture of claim 1, wherein said nucleic acid barcode further comprises one or more additional sequences selected from the group consisting of a sequence for permitting said nucleic acid barcode or a derivative thereof to couple to a flow cell of a sequencer, an adapter sequence, a unique molecular identifier sequence, a primer sequence, and a primer binding sequence.

21. The mixture of claim 1, wherein said first moiety comprises an azide group and said second moiety comprises an alkyne group.

22. The mixture of claim 1, wherein said first moiety comprises an alkyne group and said second moiety comprises an azide group.

* * * * *